(12) United States Patent
Villongco

(10) Patent No.: US 12,076,119 B2
(45) Date of Patent: *Sep. 3, 2024

(54) BOOTSTRAPPING A SIMULATION-BASED ELECTROMAGNETIC OUTPUT OF A DIFFERENT ANATOMY

(71) Applicant: Vektor Medical, Inc., Carlsbad, CA (US)

(72) Inventor: Christopher Villongco, Oakland, CA (US)

(73) Assignee: VEKTOR MEDICAL, INC., Carlsbad, CA (US)

( * ) Notice: Subject to any disclaimer, the term of this patent is extended or adjusted under 35 U.S.C. 154(b) by 1777 days.

This patent is subject to a terminal disclaimer.

(21) Appl. No.: 16/043,022

(22) Filed: Jul. 23, 2018

(65) Prior Publication Data

US 2019/0328335 A1    Oct. 31, 2019

Related U.S. Application Data

(60) Provisional application No. 62/663,049, filed on Apr. 26, 2018.

(51) Int. Cl.
*A61B 5/316*    (2021.01)
*A61B 5/00*     (2006.01)
(Continued)

(52) U.S. Cl.
CPC .......... *A61B 5/02028* (2013.01); *A61B 5/318* (2021.01); *A61B 5/319* (2021.01);
(Continued)

(58) Field of Classification Search
CPC .............................. A61B 5/7275; A61B 5/316
(Continued)

(56) References Cited

U.S. PATENT DOCUMENTS

| 4,352,163 A | 9/1982 | Schultz et al. |
| 5,458,116 A | 10/1995 | Egler |

(Continued)

FOREIGN PATENT DOCUMENTS

| CN | 102917637 A | 2/2013 |
| CN | 104680548 A | 6/2015 |

(Continued)

OTHER PUBLICATIONS

International Search Report and Written Opinion issued for PCT/US2019/069136 mailed May 11, 2020, 13 pages.

(Continued)

*Primary Examiner* — Nicole F Lavert
(74) *Attorney, Agent, or Firm* — Perkins Coie LLP

(57) ABSTRACT

Systems are provided for generating data representing electromagnetic states of a heart for medical, scientific, research, and/or engineering purposes. The systems generate the data based on source configurations such as dimensions of, and scar or fibrosis or pro-arrhythmic substrate location within, a heart and a computational model of the electromagnetic output of the heart. The systems may dynamically generate the source configurations to provide representative source configurations that may be found in a population. For each source configuration of the electromagnetic source, the systems run a simulation of the functioning of the heart to generate modeled electromagnetic output (e.g., an electromagnetic mesh for each simulation step with a voltage at each point of the electromagnetic mesh) for that source configuration. The systems may generate a cardiogram for each source configuration from the modeled electromagnetic output of that source configuration for use in predicting the source location of an arrhythmia.

25 Claims, 42 Drawing Sheets
(1 of 42 Drawing Sheet(s) Filed in Color)

(51) Int. Cl.

| | | |
|---|---|---|
| *A61B 5/02* | (2006.01) | |
| *A61B 5/318* | (2021.01) | |
| *A61B 5/319* | (2021.01) | |
| *A61B 5/339* | (2021.01) | |
| *A61B 5/341* | (2021.01) | |
| *A61B 34/10* | (2016.01) | |
| *G06V 10/00* | (2022.01) | |
| *G09B 23/30* | (2006.01) | |
| *A61B 5/107* | (2006.01) | |
| *A61B 5/25* | (2021.01) | |
| *A61B 5/349* | (2021.01) | |
| *A61B 5/361* | (2021.01) | |
| *A61B 5/363* | (2021.01) | |
| *A61B 5/364* | (2021.01) | |
| *A61B 6/03* | (2006.01) | |
| *A61B 6/50* | (2024.01) | |
| *G06F 18/22* | (2023.01) | |
| *G06F 30/20* | (2020.01) | |
| *G06N 3/045* | (2023.01) | |
| *G06N 3/08* | (2023.01) | |
| *G06N 5/04* | (2023.01) | |
| *G06N 5/046* | (2023.01) | |
| *G06N 20/00* | (2019.01) | |
| *G06T 3/4007* | (2024.01) | |
| *G06T 17/20* | (2006.01) | |
| *G06T 19/20* | (2011.01) | |
| *G06V 10/764* | (2022.01) | |
| *G09B 23/28* | (2006.01) | |
| *G16H 50/20* | (2018.01) | |
| *G16H 50/50* | (2018.01) | |

(52) U.S. Cl.
CPC .............. *A61B 5/339* (2021.01); *A61B 5/341* (2021.01); *A61B 5/7275* (2013.01); *A61B 5/743* (2013.01); *A61B 5/7435* (2013.01); *A61B 34/10* (2016.02); *G06V 10/00* (2022.01); *G09B 23/30* (2013.01); *A61B 5/1075* (2013.01); *A61B 5/25* (2021.01); *A61B 5/316* (2021.01); *A61B 5/349* (2021.01); *A61B 5/361* (2021.01); *A61B 5/363* (2021.01); *A61B 5/364* (2021.01); *A61B 5/6805* (2013.01); *A61B 5/7235* (2013.01); *A61B 5/725* (2013.01); *A61B 5/7267* (2013.01); *A61B 5/7425* (2013.01); *A61B 5/7445* (2013.01); *A61B 6/032* (2013.01); *A61B 6/503* (2013.01); *A61B 2034/105* (2016.02); *G06F 18/22* (2023.01); *G06F 30/20* (2020.01); *G06N 3/045* (2023.01); *G06N 3/08* (2013.01); *G06N 5/04* (2013.01); *G06N 5/046* (2013.01); *G06N 20/00* (2019.01); *G06T 3/4007* (2013.01); *G06T 17/205* (2013.01); *G06T 19/20* (2013.01); *G06T 2210/41* (2013.01); *G06V 10/764* (2022.01); *G06V 2201/03* (2022.01); *G09B 23/285* (2013.01); *G16H 50/20* (2018.01); *G16H 50/50* (2018.01)

(58) Field of Classification Search
USPC .......................................................... 703/11
See application file for complete search history.

(56) References Cited

U.S. PATENT DOCUMENTS

| | | |
|---|---|---|
| 5,596,634 A | 1/1997 | Fernandez et al. |
| 5,601,084 A | 2/1997 | Sheehan |
| 5,803,084 A | 9/1998 | Olson |
| 5,891,132 A | 4/1999 | Hohla |
| 6,269,336 B1 | 7/2001 | Ladd et al. |
| 6,292,783 B1 | 9/2001 | Rohler et al. |
| 6,324,513 B1 | 11/2001 | Nagai et al. |
| 6,370,412 B1 | 4/2002 | Armoundas et al. |
| 6,567,805 B1 | 5/2003 | Johnson et al. |
| 6,895,084 B1 | 5/2005 | Saylor et al. |
| 6,931,273 B2 | 8/2005 | Groenewegen et al. |
| 7,010,347 B2 | 3/2006 | Schecter |
| 7,286,866 B2 | 10/2007 | Okerlund et al. |
| 7,424,137 B2 | 9/2008 | Badilini et al. |
| 8,224,640 B2 | 7/2012 | Sharma et al. |
| 8,838,203 B2 | 9/2014 | Van Dam et al. |
| 8,849,389 B2 | 9/2014 | Anderson et al. |
| 9,014,795 B1 | 4/2015 | Yang |
| 9,129,053 B2 | 9/2015 | Mansi et al. |
| 9,277,970 B2 | 3/2016 | Mansi et al. |
| 9,320,126 B2 | 4/2016 | Valcore, Jr |
| 9,706,935 B2 | 7/2017 | Spector |
| 9,842,725 B2 | 12/2017 | Valcore, Jr |
| 9,948,642 B2 | 4/2018 | Wang |
| 10,039,454 B2 | 8/2018 | Sapp, Jr. et al. |
| 10,311,978 B2 | 6/2019 | Mansi et al. |
| 10,319,144 B2 | 6/2019 | Krummen et al. |
| 10,342,620 B2 | 7/2019 | Kiraly et al. |
| 10,363,100 B2 | 7/2019 | Trayanova et al. |
| 10,402,966 B2 | 9/2019 | Blake, III |
| 10,556,113 B2 | 2/2020 | Villongco |
| 10,617,314 B1 | 4/2020 | Villongco |
| 10,679,348 B2 | 6/2020 | Blake, III |
| 10,713,790 B2 | 7/2020 | Adler |
| 10,860,754 B2 | 12/2020 | Villongco |
| 10,861,246 B2 | 12/2020 | Voth |
| 10,925,511 B2 | 2/2021 | Blake et al. |
| 10,952,794 B2 | 3/2021 | Villongco |
| 10,998,101 B1 | 5/2021 | Tran |
| 11,065,060 B2 | 7/2021 | Villongco |
| 11,259,871 B2 | 3/2022 | Villongco |
| 2001/0049688 A1 | 12/2001 | Fratkina et al. |
| 2002/0010679 A1 | 1/2002 | Felsher |
| 2002/0154153 A1 | 10/2002 | Messinger |
| 2002/0188599 A1 | 12/2002 | McGreevy |
| 2003/0182124 A1 | 9/2003 | Khan |
| 2004/0059237 A1 | 3/2004 | Narayan |
| 2004/0083092 A1 | 4/2004 | Valles |
| 2004/0176697 A1 | 9/2004 | Kappenberger |
| 2007/0031019 A1 | 2/2007 | Lesage |
| 2007/0032733 A1 | 2/2007 | Burton |
| 2007/0060829 A1 | 3/2007 | Pappone |
| 2007/0219452 A1 | 9/2007 | Cohen et al. |
| 2007/0276270 A1 | 11/2007 | Tran |
| 2008/0077032 A1 | 3/2008 | Holmes et al. |
| 2008/0140143 A1 | 6/2008 | Ettori |
| 2008/0167567 A1 | 7/2008 | Bashour |
| 2008/0177192 A1 | 7/2008 | Chen |
| 2008/0188762 A1 | 8/2008 | John |
| 2008/0205722 A1 | 8/2008 | Schaefer |
| 2008/0234576 A1 | 9/2008 | Gavit-Houdant et al. |
| 2008/0288493 A1 | 11/2008 | Yang et al. |
| 2009/0099468 A1 | 4/2009 | Thiagalingam |
| 2009/0275850 A1 | 11/2009 | Mehendale |
| 2010/0266170 A1 | 10/2010 | Khamene |
| 2011/0028848 A1 | 2/2011 | Shaquer |
| 2011/0118590 A1 | 5/2011 | Zhang |
| 2011/0251505 A1 | 10/2011 | Narayan |
| 2011/0307231 A1 | 12/2011 | Kirchner |
| 2012/0173576 A1 | 7/2012 | Gilliam et al. |
| 2013/0006131 A1 | 1/2013 | Narayan |
| 2013/0096394 A1 | 4/2013 | Gupta |
| 2013/0131529 A1 | 5/2013 | Jia |
| 2013/0131629 A1 | 5/2013 | Jia |
| 2013/0150742 A1 | 6/2013 | Briggs |
| 2013/0197881 A1 | 8/2013 | Mansi et al. |
| 2013/0268284 A1 | 10/2013 | Heck |
| 2013/0304445 A1 | 11/2013 | Iwamura et al. |
| 2014/0005562 A1 | 1/2014 | Bunch |
| 2014/0022250 A1* | 1/2014 | Mansi ............... G06T 7/149 345/420 |
| 2014/0088943 A1 | 3/2014 | Trayanova |

(56) References Cited

U.S. PATENT DOCUMENTS

| | | |
|---|---|---|
| 2014/0107511 A1 | 4/2014 | Banet |
| 2014/0122048 A1 | 5/2014 | Vadakkumadan et al. |
| 2014/0200575 A1 | 7/2014 | Spector |
| 2014/0276152 A1 | 9/2014 | Narayan |
| 2015/0005652 A1 | 1/2015 | Banet et al. |
| 2015/0057522 A1 | 2/2015 | Nguyen |
| 2015/0216432 A1 | 8/2015 | Yang |
| 2015/0216434 A1 | 8/2015 | Ghosh |
| 2015/0216438 A1 | 8/2015 | Bokan et al. |
| 2015/0294082 A1* | 10/2015 | Passerini ............ G16H 50/50 703/11 |
| 2016/0008635 A1 | 1/2016 | Burdette |
| 2016/0038743 A1 | 2/2016 | Foster et al. |
| 2016/0113725 A1 | 4/2016 | Trayanova et al. |
| 2016/0135702 A1 | 5/2016 | Perez |
| 2016/0135706 A1 | 5/2016 | Sullivan |
| 2016/0143553 A1 | 5/2016 | Chien |
| 2016/0192868 A1 | 7/2016 | Levant et al. |
| 2016/0331337 A1 | 11/2016 | Ben-Haim |
| 2017/0027649 A1 | 2/2017 | Kiraly |
| 2017/0061617 A1 | 3/2017 | Cochet |
| 2017/0065195 A1 | 3/2017 | Nguyen |
| 2017/0068796 A1 | 3/2017 | Passerini et al. |
| 2017/0079542 A1 | 3/2017 | Spector |
| 2017/0112401 A1 | 4/2017 | Rapin |
| 2017/0150928 A1 | 6/2017 | del Alamo de Pedro |
| 2017/0156612 A1 | 6/2017 | Relan |
| 2017/0161439 A1 | 6/2017 | Raduchel et al. |
| 2017/0161896 A1 | 6/2017 | Blake, III |
| 2017/0178403 A1 | 6/2017 | Krummen |
| 2017/0185740 A1 | 6/2017 | Seegerer |
| 2017/0202421 A1 | 7/2017 | Hwang et al. |
| 2017/0202521 A1 | 7/2017 | Urman et al. |
| 2017/0209698 A1* | 7/2017 | Villongco ............ A61B 6/032 |
| 2017/0231505 A1 | 8/2017 | Mahajan |
| 2017/0273588 A1 | 9/2017 | He |
| 2017/0027465 A1 | 11/2017 | Blauer |
| 2017/0319089 A1 | 11/2017 | Lou |
| 2017/0319278 A1 | 11/2017 | Trayanova |
| 2017/0330075 A1 | 11/2017 | Tuysuzoglu |
| 2017/0367603 A1 | 12/2017 | Spector |
| 2018/0012363 A1 | 1/2018 | Seiler |
| 2018/0020916 A1 | 1/2018 | Ruppersberg |
| 2018/0032689 A1 | 2/2018 | Kiranyaz |
| 2018/0260706 A1 | 9/2018 | Galloway et al. |
| 2018/0279896 A1 | 10/2018 | Ruppersberg |
| 2018/0318606 A1 | 11/2018 | Robinson |
| 2018/0333104 A1 | 11/2018 | Sitek |
| 2019/0038363 A1 | 2/2019 | Adler |
| 2019/0060006 A1 | 2/2019 | Van Dam |
| 2019/0069795 A1 | 3/2019 | Kiranya |
| 2019/0104951 A1 | 4/2019 | Valys |
| 2019/0104958 A1 | 4/2019 | Rappel |
| 2019/0125186 A1 | 5/2019 | Ruppersberg |
| 2019/0216350 A1 | 7/2019 | Sullivan et al. |
| 2019/0223946 A1 | 7/2019 | Coates |
| 2019/0304183 A1 | 10/2019 | Krummen |
| 2019/0328254 A1 | 10/2019 | Villongco |
| 2019/0328257 A1 | 10/2019 | Villongco |
| 2019/0328457 A1 | 10/2019 | Villongco et al. |
| 2019/0328458 A1 | 10/2019 | Shmayahu |
| 2019/0332729 A1 | 10/2019 | Villongco |
| 2019/0333639 A1 | 10/2019 | Villongco |
| 2019/0333641 A1 | 10/2019 | Villongco |
| 2019/0333643 A1 | 10/2019 | Villongco |
| 2020/0324118 A1 | 10/2020 | Garner et al. |
| 2020/0405148 A1 | 12/2020 | Tran |
| 2021/0015390 A1 | 1/2021 | Zhou et al. |
| 2021/0205025 A1 | 7/2021 | Erkamp et al. |
| 2021/0219923 A1 | 7/2021 | Eun Young Yang |
| 2021/0259560 A1 | 8/2021 | Venkatraman |
| 2022/0047237 A1 | 2/2022 | Liu |

FOREIGN PATENT DOCUMENTS

| | | |
|---|---|---|
| CN | 105078440 A | 11/2015 |
| CN | 105194799 A | 12/2015 |
| CN | 105263405 A | 1/2016 |
| CN | 106725428 | 5/2017 |
| CN | 113851225 A | 12/2021 |
| CN | 114206218 A | 3/2022 |
| JP | H4174643 A | 6/1992 |
| JP | H08289877 A | 11/1996 |
| JP | 2007517633 A | 7/2007 |
| JP | 2012508079 A | 4/2012 |
| JP | 2014530074 A | 11/2014 |
| JP | 2015163199 A | 9/2015 |
| JP | 2017140381 A | 8/2017 |
| WO | 2006066324 A1 | 6/2006 |
| WO | 2015153832 A1 | 10/2015 |
| WO | 2018190715 A1 | 10/2018 |
| WO | 2019118640 A1 | 6/2019 |
| WO | 2020101864 | 5/2020 |
| WO | 2020142539 | 7/2020 |

OTHER PUBLICATIONS

Thakor and Tong (Annual Reviews in Biomedicine and Engineering (2004) vol. 6, 453-495).

International Search Report and Written Opinion issued in PCT/US2020/036754 mailed Oct. 15, 2020, 13 pages.

Siregar, P. "An Interactive Qualitative Model in Cardiology" Computers and Biomedical Research 28, pp. 443-478, May 16, 1994.

Cuculich, Phillip S. et al., "Noninvasive Cardiac Radiation for Ablation of Ventricular Tachycardia" New England Journal of Medicine, 377; 24, pp. 2325-2336, Dec. 14, 2017.

Graham, Adam J. et al., "Evaluation of ECG Imaging to Map Haemodynamically Stable and Unstable Ventricular Arrhythmias" downloaded from http://ahajournals.org on Jan. 22, 2020.

Sapp, John L. et al., "Real-Time Localization of Ventricular Tachycardia Origin From the 12-Lead Electrocardiogram" JACC: Clinical Electrophysiology by the Amercian College of Cardiology Foundation, vol. 3, 2017, pp. 687-699.

Potse, Mark et al., "Continuos Localization of Cardian Activation Sites Using a Database of Multichannel ECG Recordings" IEEE Transactions of Biomedical Engineering, vol. 47, No. 5, May 2000, pp. 682-689.

Zhou, Shijie et al. "Rapid 12-lead automoated localization method: Comparison to electrocardiogramaging (ECGI) in patient-specific geometry", Journal of Electrocardiology, vol. 51, 2018, pages S92-S97.

Zhou, Shijie et al. "Localization of ventricular activation origin using patient-specific geometry: Preliminary results" J. Carciovasc Electrophysiol, 2018; 29: pp. 979-986.

International Search Report and Written Opinion issued for PCT/US2019/058217 mailed Feb. 7, 2020, 9 pages.

Andreu et al., "Integration of 3D Electroanatomic Maps and Magnetic Resonance Scar Characterization Into the Navigation System to Guide Ventricular Tachycardia Ablation", Circ Arrhythm Electrophysiol, Oct. 2011, 4(5), pp. 674-683.

Acharya et al., A deep convolutional neural network model to classify heartbeats, Computers in Biology and Medicine (Oct. 1, 2017) vol. 89, pp. 389-396.

Acharya et al., Deep convolutional neural network for the automated detection and diagnosis of seizure using EEG signals, Computers in Biology and Medicine (Sept 1, 2018, Epub Sep. 27, 2017) 100:270-278.

Acharya Ur, Fujita H, Lih OS, Hagiwara Y, Tan JH, Adam M. Automated detection of arrhythmias using different intervals of tachycardia ECG segments with convolutional neural network. Information sciences. Sep. 1, 2017;405:81-90.

Bond et al., XML-BSPM: An XML Format for Storing Body Surface Potential Map Recordings, BMC Medical Informatics and Decision Making 2010, 10:28, http://www.biomedcentra.com/1472-6947/10/28, 27 pages.

(56) References Cited

OTHER PUBLICATIONS

Dandu Ravi Varma, "Managing DICOM images: Tips and tricks for the radiologist", Indian J Radiol Imaging., Jan.-Mar. 2012; 22(1), pp. 4-13.
Extended European Search Report issued in European Patent Application No. 19215701.4 and dated Apr. 17, 2020, 9 pages.
Extended European Search Report issued in European Patent Application No. 19792821.1 and dated Mar. 15, 2021. 10 pages.
Garg, et al., ECG Paper Records Digitization Through Image Processing Techniques, vol. 48, No. 13, Jun. 2012, 4 pages.
Goodfellow, Ian et al., Generative Adversarial Nets, Advances in Neural Information Processing Systems, pp. 2672-2680, 2014.
Halevy, A., Norvig, P., & Pereira, F. (2009). The unreasonable effectiveness of data. IEEE intelligent systems, 24(2), 8-12.
He, Zhenliang et al., Facial Attribute Editing by Only Changing What You Want, IEEE Transactions on Image Processing, 2018.
Hershey S, Chaudhuri S, Ellis DP, Gemmeke JF, Jansen A, Moore RC, Plakal M, Platt D, Saurous RA, Seybold B, Slaney M. CNN architectures for large-scale audio classification. In2017 IEEE international conference on acoustics, speech and signal processing (ICASSP) Mar. 5, 2017 (pp. 131-135). IEEE.
International Searching Authority, International Search Report and Written Opinion, PCT Patent Application PCT/US2021/057616, mailed Jan. 28, 2022, 9 pages.
Jacquemet, V., "Lessons from Computer Simulation of Ablation of Atrial Fibrillation", J Physiol. 594(9): 2417-2430, May 1, 2016.
JPO, Notice of Reasons for Refusal for Japanese Patent Application No. 2018-527085. Mail Date: Dec. 23, 2020. 14 pages with English translation.
Kiranyaz et al., Real-time patient-specific EDG classification by 1-D convolutional neural networks, IEEE Transactions on Biomedical Engineering (Mar. 2016) 63:664-675.
Kiranyaz S, Ince T, Hamila R, Gabbouj M. Convolutional neural networks for patient-specific ECG classification. In2015 37th Annual International Conference of the IEEE Engineering in Medicine and Biology Society (EMBC) Aug. 25, 2015 (pp. 2608-2611). IEEE.
Lee H, Kwon H. Going deeper with contextual CNN for hyperspectral image classification. IEEE Transactions on Image Processing, Jul. 11, 2017;26(10):4843-55.
Li D, Zhang J, Zhang Q, Wei X. Classification of ECG signals based on 1 D convolution neural network. In2017 IEEE 19th International Conference on e-Health Networking, Applications and Services (Healthcom) Oct. 12, 2017 (pp. 1-6). IEEE.
Light, D., E., et al. "Two Dimensional Arrays for Real Time Volumetric and Intracardiac Imaging with Simultaneous Electrocardiagram", 1196-2000 IEEE Ultrasonics Symposium, retrieved on Sep. 24, 2021.
Lyon, et al. J.R. Soc Interface vol. 15:1-18. (2017).
Office Action mailed Mar. 18, 2021, Canada App. 3080944.
Office Action Response filed Mar. 23, 2021, U.S. Appl. No. 17/082,892.
Pan, J., S., et al., "A Survey on Transfer Learning," IEEE Transactions On Knowledge and Data Engineering, vol. 22, No. 10, Oct. 2010, 15 pages.
Rahhal et al., Convolutional neural networks for electrocardiogram classification, Journal of Medical and Biological Engineering (Mar. 30, 2018) 38: 1014-1025.
Ravichandran et al., Novel Tool for Complete Digitization of Paper Electrocardiogramata, vol. 1, 2013, 7 pages.
Sapp et al., "Real-Time Localization of Ventricular Tachycardia Origin From the 12-Lead Electrocardiogram", JACC Clinical Electrophysiology, vol. 3, No. 7, Jul. 2017.
Sharma, et al., Digitalization of ECG Records, International Journal of Engineering Research and Applications, www.ijera.com, ISSN: 2248-9622, vol. 10, Issue 6, (Series-VIII) Jun. 2020, pp. 01-05.
Shin HC, Roth HR, Gao M, Lu L, Xu Z, Nogues I, Yao J, Mollura D, Summers RM. Deep convolutional neural networks for computer-aided detection: CNN architectures, dataset characteristics and transfer learning. IEEE transactions on medical imaging. Feb. 11, 2016;35(5): 1285-98.
Therrien R, Doyle S. Role of training data variability on classifier performance and generalizability. In Medical Imaging 2018: Digital Pathology Mar. 6, 2018 (vol. 10581, p. 1058109). International Society for Optics and Photonics.
USPTO, Final Office Action received for U.S. Appl. No. 16/444,340. Mail Date: Dec. 23, 2020. 9 pages.
USPTO, Non-Final Office Action received for U.S. Appl. No. 16/295,934. Mail Date: Dec. 23, 2020. 12 pages.
USPTO, Restriction Requirement received for U.S. Appl. No. 17/082,892. Mail Date: Feb. 2, 2021. 8 pages.
USPTO, Non-Final Office Action received for U.S. Appl. No. 17/082,892. Mail Date: Mar. 1, 2021. 33 pages.
USPTO, Non-Final Office Action received for U.S. Appl. No. 17/082,835. Mail Date: Jan. 29, 2021. 22 pages.
USPTO, Office Action mailed Apr. 5, 2021, U.S. Appl. No. 17/082,835.
USPTO, Office Action mailed Apr. 12, 2021, U.S. Appl. No. 17/082,892.
USPTO, Office Action mailed Apr. 15, 2021, U.S. Appl. No. 16/043,054.
USPTO, Office Action mailed Jul. 14, 2021, U.S. Appl. No. 16/247,463.
Xiong et al. Computing and Cardiology vol. 44: pp. 1-4. (2017).
Zentara, et al., ECG Signal Coding Methods in Digital Systems, Communication Papers of the Federated Conference on Computer Science and Information Systems,DOI: 10.15439/2018F108, ISSN 2300-5963 ACSIS, vol. 17, pp. 95-102.
Zhang, C., et al. "Patient-Specific ECG Classification Based on Recurrent Neural Networks and Clustering Technique," Proceedings of the IASTED International Conference in Biomedical Engineering (Bio Med 2017); Feb. 20-21, 2017, in Innsbruck, Austria, 5 pages.
Zhu X, Vondrick C, Fowlkes CC, Ramanan D. Do we need more training data ?. International Journal of Computer Vision.Aug. 2016;119(1):76-92.
Zubair M, Kim J, Yoon C. An automated ECG beat classification system using convolutional neural networks. In2016 6th international conference on IT convergence and security (ICITCS) Sep. 26, 2016 (pp. 1-5). IEEE.
International Search Report and Written Opinion issued for PCT/US2019/029181 mailed Sep. 16, 2019.
International Search Report and Written Opinion issued for PCT/US2019/029184 mailed Sep. 24, 2019.
Carrault, Guy, et al. "A model-based approach for learning to identify cardiac arrhythmias," Joint European Conference on Artificial Intelligence in Medicine and Medicine Decision Making. Springer, Berlin Heidelberg, 1999.
Carrualt, Guy, et al. "Temporal abstraction and inductive logic programming for arrhythmia recognition from electrocardiograms." Artificial intelligence in medicine 28.3 (2003): 231-263.
Hren, Rok, et al. "Value of simulated body surface potential maps as templates in localizing sites of ectopic activation for radiofrequency ablation" Physiol. Meas. 18 (1997) 373-400. Mar. 7, 1997.
International Search Report and Written Opinion issued for PCT/US16/68449 mailed on Mar. 29, 2017.
Cobb, Leonard A., et al. "Changing incidence of out-of-hospital ventricular fibrillation, 1980-2000." Jama 288.23 (2002) 3008-3013.
Gonzales, Matthew J., et al. "Structural contributions to fibrillatory rotors in a patient-derived computational model of the atria." EP Europace 16.suppl 4 (2014): iv3-iv10.
Krishnamurthy, Adarsh, et al. "CRT Response is Greater in Patients With Larger Fraction of the Myocardium Performing Negative Regional Work." Circulation 128.Suppl 22 (2013): A11135-A11135, Abstract only.
Krishnamurthy, Adarsh, et al. "Patient-specific models of cardiac biomechanics." Journal of computational physics 244 (2013): 4-21.
Krummen, David E., et al. "Rotor stability separates sustained ventricular fibrillation from selfterminating episodes in humans." Journal of the American College of Cardiology 63.24 (2014): 2712-2721.
Nash, Martyn P., et al. "Evidence for multiple mechanisms in human ventricular fibrillation." Circulation 114.6 (2006): 536-542.

(56) References Cited

OTHER PUBLICATIONS

Ten Tusscher, K. H. W. J., et al. "A model for human ventricular tissue." American Journal of PhysioloQy-Heart and Circulatory PhysioloQy 286.4 (2004): H1573-H1589.

Villongco, Christopher T., et al. "Patient-specific modeling of ventricular activation pattern using surface ECG derived vectorcardiogram in bundle branch block." Progress in biophysics and molecular bioloQy 115.2 (2014): 305-313.

Vadakkumpadan, Fijoy, et al. "Image-based estimation of ventricular fiber orientations for personalized modeling of cardiac electrophysiology." IEEE-TMI 31.5 (2012): 1051-1060.

Taggart, Peter, et al. "Developing a novel comprehensive framework for the investigation of cellular and whole heart electrophysiology in the in situ human heart: Historical perspectives, current progress and future prospects. " Progress in biophysics and molecular biology 115.2-3 (2014): 252-260.

Tobon, Catalina, et al. "Dominant frequency and organization index maps in a realistic three-dimensional computational model of atrial fibrillation." Europace 14.suppl_5 (2012): v25-v32.

Kors, J.A., et al., "Recontruction of the Frank vectorcardiogram from standard electrocardiogramads: diagnostic comparison of different methods," European Heart Journal, vol. 11, Issue 12, Dec. 1, 1990, pp. 1083-1092.

Tomašić, Ivan et al., "Electrocardiograms With Reduced Nos. of Leads—Synthesis of the 12-Lead ECG," IEEE Reviews in Biomedical Engineering, vol. 7, 2014, pp. 126-142.

Frank, Ernest, "An Accurate, Clinically Practical System for Spatial Vectorcardiography," American Heart Association, Inc., downloaded from http://circ.ahajournals.org/ at Cons California Dig Lib on Mar. 12, 2014.

Vozda, M et al.., "Methods for derivation of orthogonal leads from 12-lead electrocardiogram: A review," Elsevier, Biomedical Signal Processing and Control 19 (2015), 23-34.

Si, Hang, "TetGen, a Delaunay-Based Quality Tetrahedral Mesh Generator," ACM Transactions on Mathematical Software, vol. 41, No. 2, Article 11, Jan. 2015, 36 pages.

Tajbakhsh, Nima et al., "Convolutional Neural Networks for Medical Image Analysis: Full Training or Fine Tuning?" IEEE Transactions on Medical Imaging (2016) vol. 35, e-pages 1-17).

\* cited by examiner

BOOTSTRAPPING A SIMULATION-BASED ELECTROMAGNETIC OUTPUT OF A DIFFERENT ANATOMY

CROSS-REFERENCE TO RELATED APPLICATION

This application claims the benefit of U.S. Provisional Application No. 62/663,049, filed on Apr. 26, 2018, entitled "MACHINE LEARNING USING SIMULATED CARDIOGRAMS," which is hereby incorporated by reference in its entirety.

This application is related to the following applications filed concurrently: U.S. Pat. No. 16,042,984, entitled "GENERATING SIMULATED ANATOMIES OF AN ELECTROMAGNETIC SOURCE'"; U.S. Pat. No. 16,042,953, entitled "GENERATING A MODEL LIBRARY OF MODELS OF AN ELECTROMAGNETIC SOURCE"; U.S. Pat. No. 16,042,973, entitled "USER INTERFACE FOR PRESENTING SIMULATED ANATOMIES OF AN ELECTROMAGNETIC SOURCE"; U.S. Pat. No. 16,042,993, entitled "CONVERTING A POLYHEDRAL MESH REPRESENTING AN ELECTROMAGNETIC SOURCE"; U.S. Pat. No. 16,043,011, entitled "GENERATING APPROXIMATIONS OF CARDIOGRAMS FROM DIFFERENT SOURCE CONFIGURATIONS"; U.S. Pat. No. 16,043,034, entitled "IDENTIFYING AN ATTRIBUTE OF AN ELECTROMAGNETIC SOURCE CONFIGURATION BY MATCHING SIMULATED AND PATIENT DATA"; U.S. Pat. No. 16,043,041, entitled "MACHINE LEARNING USING CLINICAL AND SIMULATED DATA"; U.S. application Ser. No. 16,043,050, entitled "DISPLAY OF AN ELECTROMAGNETIC SOURCE BASED ON A PATIENT-SPECIFIC MODEL"; and U.S. Pat. No. 16,043,054, entitled "DISPLAY OF AN ELECTRICAL FORCE GENERATED BY AN ELECTRICAL SOURCE WITHIN A BODY," each is hereby incorporated by reference in its entirety.

BACKGROUND

Many heart disorders can cause symptoms, morbidity (e.g., syncope or stroke), and mortality. Common heart disorders caused by arrhythmias include inappropriate sinus tachycardia ("IST"), ectopic atrial rhythm, junctional rhythm, ventricular escape rhythm, atrial fibrillation ("AF"), ventricular fibrillation ("VF"), focal atrial tachycardia ("focal AT"), atrial microreentry, ventricular tachycardia ("VT"), atrial flutter ("AFL"), premature ventricular complexes ("PVCs"), premature atrial complexes ("PACs"), atrioventricular nodal reentrant tachycardia ("AVNRT"), atrioventricular reentrant tachycardia ("AVRT"), permanent junctional reciprocating tachycardia ("PJRT"), and junctional tachycardia ("JT"). The sources of arrhythmias may include electrical rotors (e.g., ventricular fibrillation), recurring electrical focal sources (e.g., atrial tachycardia), anatomically based reentry (e.g., ventricular tachycardia), and so on. These sources are important drivers of sustained or clinically significant episodes. Arrhythmias can be treated with ablation using different technologies, including radiofrequency energy ablation, cryoablation, ultrasound ablation, laser ablation, external radiation sources, directed gene therapy, and so on by targeting the source of the heart disorder. Since the sources of heart disorders and the locations of the source vary from patient to patient, even for common heart disorders, targeted therapies require the source of the arrhythmia to be identified.

Unfortunately, current methods for reliably identifying the source locations of the source of a heart disorder can be complex, cumbersome, and expensive. For example, one method uses an electrophysiology catheter having a multi-electrode basket catheter that is inserted into the heart (e.g., left ventricle) intravascularly to collect from within the heart measurements of the electrical activity of the heart, such as during an induced episode of VF. The measurements can then be analyzed to help identify a possible source location. Presently, electrophysiology catheters are expensive (and generally limited to a single use) and may lead to serious complications, including cardiac perforation and tamponade. Another method uses an exterior body surface vest with electrodes to collect measurements from the patient's body surface, which can be analyzed to help identify an arrhythmia source location. Such body surface vests are expensive, are complex and difficult to manufacture, and may interfere with the placement of defibrillator pads needed after inducing VF to collect measurements during the arrhythmia. In addition, the vest analysis requires a computed tomography ("CT") scan and is unable to sense the interventricular and interatrial septa where approximately 20% of arrhythmia sources may occur.

BRIEF DESCRIPTION OF THE DRAWINGS

This application contains at least one drawing executed in color. Copies of this application with color drawing(s) will be provided by the Office upon request and payment of the necessary fees.

DETAILED DESCRIPTION

Figure 1:
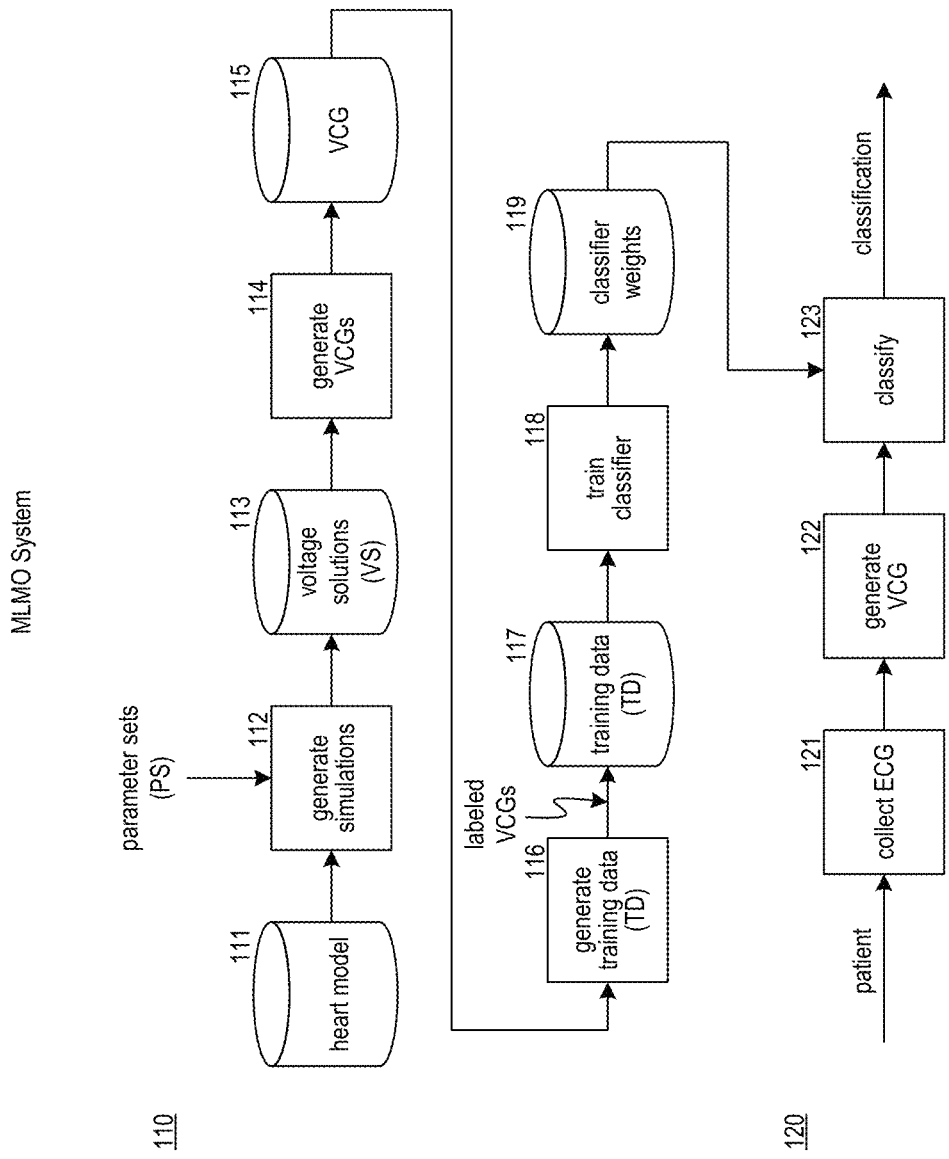
FIG. 1 is a block diagram that illustrates the overall processing of the MLMO system in some embodiments.

Methods and systems are provided for generating data representing electromagnetic states (e.g., normal sinus rhythm versus ventricular fibrillation) of an electromagnetic source (e.g., a heart) within a body for various purposes such as medical, scientific, research, and engineering purposes. The systems generate the data based on source configurations (e.g., dimensions of, and scar or fibrosis or pro-arrhythmic substrate location within, a heart) of the electromagnetic source and a computational model of the electromagnetic output of the electromagnetic source. The systems may dynamically generate the source configurations to provide representative source configurations that may be found in a population. For each source configuration of the electromagnetic source, the systems run a simulation of the functioning of the electromagnetic source to generate modeled electromagnetic output for that source configuration. The systems generate derived electromagnetic data (e.g., a vectorcardiogram) for each source configuration from the modeled electromagnetic output of that source configuration. The system may then use the modeled electromagnetic output for various purposes such as identifying locations of disorders within the electromagnetic source of a patient's body, guiding a procedure to repair (e.g., directed gene therapy) or modify (e.g., ablate) the electromagnetic source, predicting results of a procedure on the electromagnetic source, analyzing genetic defects, and so on. The systems may include a machine learning based on modeled output system and a model library generation system, which are described below.

Machine Learning Based on Modeled Output System

A method and a system are provided for generating a classifier for classifying electromagnetic data derived from an electromagnetic source within a body. A body may be, for example, a human body, and the electromagnetic source may be a heart, a brain, a liver, a lung, a kidney, or another part of the body that generates an electromagnetic field that can be measured from outside or inside the body. The electromagnetic fields can be measured by various measuring devices (e.g., electrocardiograph and electroencephalograph) using, for example, one or more (e.g., 12) leads connected to electrodes attached to or adjacent to (e.g., via a smart watch device) a patient's body, a body surface vest worn by a patient, an intra-electromagnetic source device (e.g., a basket catheter), a cap worn by a patient, and so on. The measurements can be represented via a cardiogram such as an electrocardiogram ("ECG") and a vectorcardiogram ("VCG"), an electroencephalogram ("EEG"), and so on. In some embodiments, a machine learning based on modeled output ("MLMO") system is provided to generate a classifier by modeling electromagnetic output of the electromagnetic source for a variety of source configurations and using machine learning to train a classifier using derived electromagnetic data that is derived from the modeled electromagnetic output as training data. The MLMO system is described below primarily to generate a classifier for electromagnetic data of the heart.

In some embodiments, the MLMO system employs a computational model of the electromagnetic source to generate training data for training the classifier. A computational model models electromagnetic output of the electromagnetic source over time based on a source configuration of the electromagnetic source. The electromagnetic output may represent electrical potential, a current, a magnetic field, and so on. When the electromagnetic ("EM") source is a heart, the source configuration may include any subset of the group consisting of information on geometry and muscle fibers of the heart, torso anatomy, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, other normal and pathophysiologic feature distributions, and so on, and the EM output is a collection of the electric potentials at various heart locations over time. To generate the EM output, a simulation may be performed for simulation steps of a step size (e.g., 1 ms) to generate an EM mesh for that step. The EM mesh may be a finite-element mesh that stores the value of the electric potential at each heart location for that step. For example, the left ventricle may be defined as having approximately 70,000 heart locations with the EM mesh storing an electromagnetic value for each heart location. If so, a three-second simulation with a step size of 1 ms would generate 3,000 EM meshes that each include 70,000 values. The collection of the EM meshes is the EM output for the simulation. A computational model is described in C. T. Villongco, D. E. Krummen, P. Stark, J. H. Omens, & A. D. McCulloch, "Patient-specific modeling of ventricular activation pattern using surface ECG-derived vectorcardiogram in bundle branch block," Progress in Biophysics and Molecular Biology, Volume 115, Issues 2-3, August 2014, Pages 305-313, which is hereby incorporated by reference. In some embodiments, the MLMO system may generate values for points between the vertices as the mesh, rather than just at the vertices. For example, the MLMO system may calculated the values for such points using a Gaussian quadrature technique.

In some embodiments, the MLMO system generates the training data by running many simulations, each based on a different source configuration, which is a set of different values for the configuration parameters of the computational model. For example, the configuration parameters for the heart may be cardiac geometry, rotor location, focal source location, ventricular orientation in the chest, ventricular myofiber orientation, cardiomyocyte intracellular potential electrogenesis and propagation, and so on. Each configuration parameter may have a set or range of possible values. For example, the rotor location may be 78 possible parameter sets corresponding to different locations within a ventricle. Since the MLMO system may run a simulation for each combination of possible values, the number of simulations may be in the millions.

In some embodiments, the MLMO system uses EM outputs of the simulations to train the classifier for the generation of a classification based on EM data collected from a patient. The MLMO system may generate derived EM data for each EM output of a simulation. The derived EM data correspond to EM data generated based on measurements that would be collected by an EM measuring devices that use, for example, 12 leads to generate an ECG or a VCG, a body surface vest, an intra-electromagnetic source device, and so on. The ECG and VCG are equivalent source representations of the EM output. The MLMO then generates a label (or labels) for each derived EM data to specify its corresponding classification. For example, the MLMO system may generate a label that is the value of a configuration parameter (e.g., rotor location) used when generating the EM output from which the EM data was derived. The collection of the derived EM data, which correspond to feature vectors, and their labels compose the training data for training the classifier. The MLMO system then trains the classifier. The classifier may be any of a variety or combination of classifiers including neural networks such as fully-connected, convolutional, recurrent, autoencoder, or restricted Boltzmann machine, a support vector machine, a Bayesian classifier, and so on. When the classifier is a deep neural network, the training results in a set of weights for the activation functions of the deep neural network. The classifier selected may be based on the type of disorder to be identified. For example, certain types of neural networks may be able to effectively train based on focal sources, but not rotor sources.

In some embodiments, the MLMO system may augment the training data with additional features from the configuration parameters of the source configuration used to generate the training data. For example, the MLMO system may generate additional features to represent the geometry of the heart, the orientation of the heart, scar or fibrosis or pro-arrhythmic substrate location or locations, ablation location, ablation shape, and so on. The MLMO system may input these additional features into the fully connected layer along with the output generated by the layer before the fully connected layer of a convolutional neural network ("CNN"), which is described below. The output of the layer before the fully connected layer (e.g., pooling layer) may be "flattened" into a one-dimensional array, and the MLMO system may add the additional features as further elements of the one-dimensional array. The output of the fully connected layer may provide a probability for each label used in the training data. The probabilities will thus be based on the combination of the derived EM data and the additional features. The classifier will be able to output different probabilities even when the derived EM data is the same or similar to reflect, for example, that the same or similar EM data may be generated for patients with different heart geometries and different scar or fibrosis or pro-arrhythmic substrate locations. The MLMO system may alternatively employ an additional classifier that (1) inputs the probabilities generated by the CNN based only on the derived EM data and (2) inputs the additional features and then outputs a final probability for each classification that factors in the additional features. The additional classifier may be, for example, a support vector machine. The CNN and the additional classifier may be trained in parallel.

In some embodiments, the MLMO system normalizes the VCGs of each cycle of the training data in both the voltage and time axes. A cycle may be defined as a time interval (e.g., start time to end time) defining a single unit or beat of periodic electrical activity during normal or abnormal rhythms. Cycles facilitate beat-by-beat analysis of source configuration evolution over time and enable subsequent voltage and time normalization over each cycle. Normalization preserves salient features of voltage-time dynamics and improves generalizability of the training data to variations in source configuration parameters (e.g., torso conductivities, lead placement and resistance, myocardial conduction velocity, action potential dynamics, overall heart size, etc.) anticipated in real patients. The MLMO system may normalize the voltages to a range between −1 and 1 and the time to a fixed range of 0 to 1 in increments of milliseconds or percentages. To normalize the voltages for a cycle, the MLMO system may identify the maximum magnitude of the vectors across the axes. The MLMO system divides each voltage by the maximum magnitude. To normalize the time axis, the MLMO system performs an interpolation from the number of points in the VCG, which may be more or less than 1000, to the 1000 points of the normalized cycle.

In some embodiments, after the classifier is trained, the MLMO system is ready to generate classifications based on EM and other routinely available clinical data collected from patients. For example, an ECG may be collected from a patient, and a VCG may be generated from the ECG. The VCG is input to the classifier to generate a classification indicating, for example, a rotor location for the patient. As a result, even though the geometry of the patient's heart is not known or no simulation was based on the same geometry as the patient's heart, the MLMO system can be used to generate a classification. If other patient measurements such as cardiac dimensions and orientation, scar or fibrosis or pro-arrhythmic substrate configuration, etc. are available, they may be included as input with the EM data to improve accuracy. This allows the classifier to effectively learn complex hidden features in various clinical data that are not directly represented by the training data.

In some embodiments, the MLMO system may classify source stability (i.e., the beat-to-beat consistency of a dominant arrhythmia source localized to a particular region in the heart) by generating training data that is based on sequences of consecutive cycles that have similar EM features. A technique for determining the stability of arrhythmia sources is described in Krummen, D., et al., Rotor Stability Separates Sustained Ventricular Fibrillation from Self-Terminating Episodes in Humans, Journal of American College of Cardiology, Vol. 63, No. 23, 2014, which is hereby incorporated by reference. This reference demonstrates the efficacy of targeted ablation at stable source sites for preventing recurring arrhythmic episodes. For example, given a VCG, the MLMO system may identify the cycles and then identify sequences of two consecutive cycles, three consecutive cycles, four consecutive cycles, and so on in which all the VCG cycles in the sequence are of similar morphology to each other. Each identified sequence may be labeled based on the value of a parameter of the source configuration used to generate the VCG. The MLMO system may then train a separate classifier for each sequence length (e.g., 2, 3, 4, and so on) using the training data for the sequences of that sequence length. For example, the MLMO system may train a classifier for sequences of two cycles and a separate classifier for sequences of three cycles. To generate a classification for a patient, the MLMO system may identify sequences of similar cycles of varying sequence lengths in the VCG of the patient and input those sequences into the classifier for the appropriate sequence length. The MLMO system may then combine the classifications from all the classifiers to arrive at a final classification or may simply output all the classifications.

Although a classifier could be trained using actual patient ECGs or VCGs and corresponding intracardiac basket catheter measurements of source location, the cost of collecting, preparing, and labeling a sufficient number of data would be prohibitive. Moreover, training data based on actual patients would likely be too sparse and noisy to be effective at training a classifier for a large population. In some embodiments, the MLMO system could be trained using a combination of actual patient VCGs and VCGs derived from simulations.

FIG. 1 is a block diagram that illustrates the overall processing of the MLMO system in some embodiments. The MLMO system includes classifier generation components 110 and classification components 120. The computational model for a heart is a heart model that may include data and code stored in a heart model data store 111. A generate simulations component 112 inputs the heart model and the parameter sets for the simulations. The parameter sets, also referred to as source configurations, may include a parameter set for each combination of possible values of the parameters or may specify how to generate (e.g., via a computer code) the parameter sets. For example, the computer code for the rotor location parameter may include a list of possible rotor locations and for the ventricle orientation parameter may dynamically generate the values from a base orientation axis along with code for generating possible tilt angles from that base orientation such as an x-axis and a y-axis increment. The output of the generate simulations component is stored in a voltage solutions data store 113 where a voltage solution is an EM output. A voltage solution is an example of an EM mesh. A generate VCGs component 114 generates a VCG from the voltage solutions and stores the VCG in a VCG data store 115. The generate VCGs component may generate an ECG from the voltage solutions and then generate a VCG from the ECG. The generation of a VCG from an ECG is described in J. A. Kors, G. Van Herpen, A. C. Sittig, & J. H. Van Bemmel, "Reconstruction of the Frank vectorcardiogram from standard electrocardiographic leads: diagnostic comparison of different methods," *European Heart Journal*, Volume 11, Issue 12, 1 Dec. 1990, Pages 1083-1092, which is hereby incorporated by reference. A generate training data component 116 inputs the VCGs and labels each VCG with a label or labels that may be derived from the parameter sets and stores the training data in a training data store 117. A label may be, for example, the value of a parameter of the parameter set used to generate the EM output from which the VCG is derived. A train classifier component 118 inputs the training data, trains a classifier, and stores the weights (e.g., of activation functions of a convolutional neural network) in a classifier weights data store 119. To generate a classification, a collect ECG component 121 inputs an ECG collected from a patient. A generate VCG component 122 generates a VCG from the ECG. A classify component 123 inputs the VCG and generates a classification using the classifier weights of the trained classifier.

The computing systems (e.g., network nodes or collections of network nodes) on which the MLMO system and the other described systems may be implemented may include a central processing unit, input devices, output devices (e.g., display devices and speakers), storage devices (e.g., memory and disk drives), network interfaces, graphics processing units, cellular radio link interfaces, global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, cloud-based servers, desktop computers, laptops, tablets, e-readers, personal digital assistants, smartphones, gaming devices, servers, and so on. For example, the simulations and training may be performed using a high-performance computing system, and the classifications may be performed by a tablet. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the MLMO system and the other described systems. The data transmission media are used for transmitting data via transitory, propagating signals or carrier waves (e.g., electromagnetism) via a wired or wireless connection. The computing systems may include a secure cryptoprocessor as part of a central processing unit for generating and securely storing keys and for encrypting and decrypting data using the keys.

The MLMO system and the other described systems may be described in the general context of computer-executable instructions, such as program modules and components, executed by one or more computers, processors, or other devices. Generally, program modules or components include routines, programs, objects, data structures, and so on that perform tasks or implement data types of the MLMO system and the other described systems. Typically, the functionality of the program modules may be combined or distributed as desired in various examples. Aspects of the MLMO system and the other described systems may be implemented in hardware using, for example, an application-specific integrated circuit ("ASIC") or field programmable gate array ("FPGA").

Figure 2:
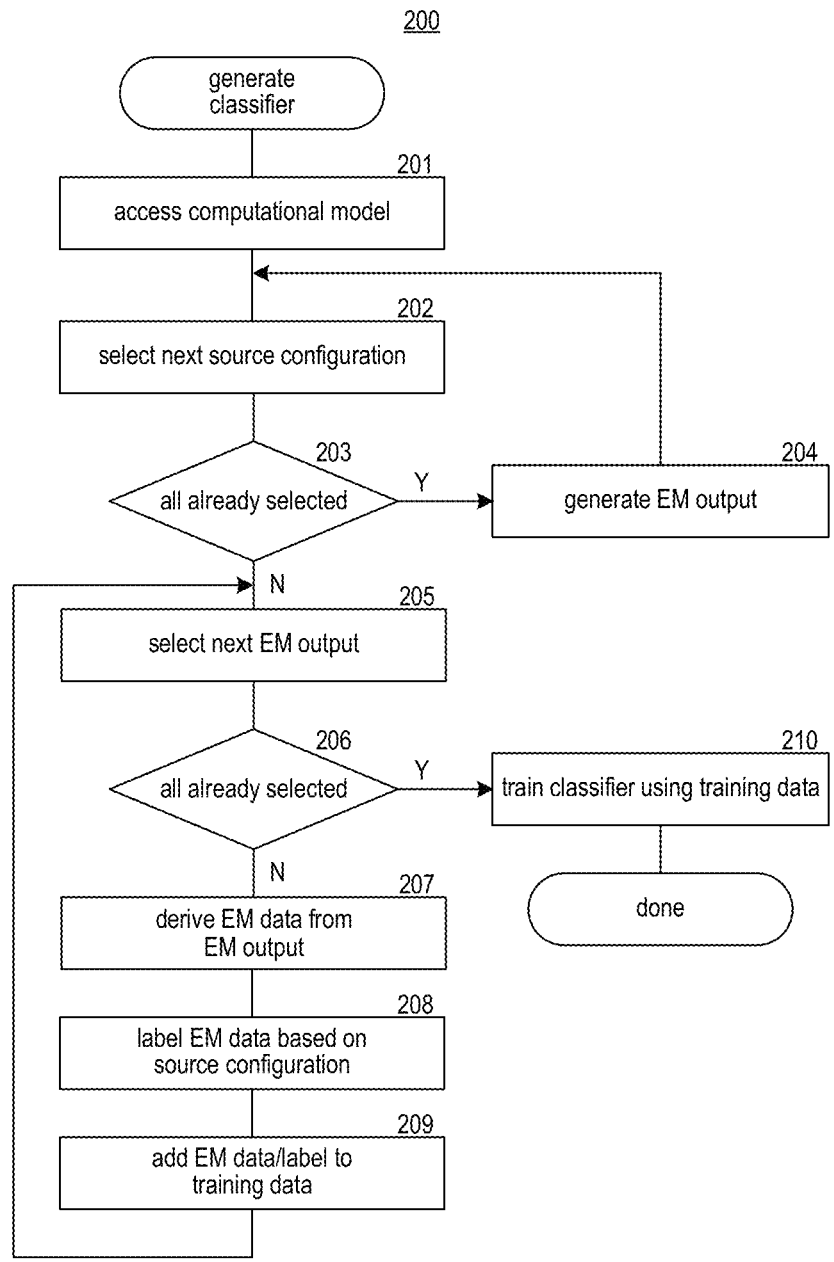
FIG. 2 is a flow diagram that illustrates the overall processing of generating a classifier by the MLMO system in some embodiments.

FIG. 2 is a flow diagram that illustrates the overall processing of generating a classifier by the MLMO system in some embodiments. A generate classifier component 200 is executed to generate a classifier. In block 201, the component accesses the computational model to be used to run the simulations. In block 202, the component selects the next source configuration (i.e., parameter set) to be used in a simulation. In decision block 203, if all the source configurations have already been selected, then the component continues at block 205, else the component continues at block 204. In block 204, the component runs the simulation using the selected source configuration to generate an EM output for the simulation and then loops to block 202 to select the next source configuration. In block 205, the component selects the next EM output that was generated by a simulation. In decision block 206, if all the EM outputs have already been selected, then the component continues at block 210, else the component continues at block 207. In block 207, the component derives the EM data from the EM output. For example, the EM output may be a collection of EM meshes, and the EM data may be an ECG or a VCG derived from the electromagnetic values of the EM mesh. In some embodiments, the component may in addition identify cycles (periodic intervals of arrhythmic activity) within the ECG or VCG. A cycle may be delimited by successive crossings from a negative voltage to a positive voltage ("positive crossings") or successive crossings from a positive voltage to a negative voltage ("negative crossings") with respect to a spatial direction or set of directions comprising a reference frame or set of reference frames. A reference frame may coincide with anatomical axes (e.g., left-to-right with x, superior-to-inferior with y, anterior-to-posterior with z), imaging axes (e.g., CT, MR, or x-ray coordinate frames), body-surface lead vectors, principal axes computed by principal component analysis of measured or simulated EM source configurations and outputs, or user-defined directions of interest. For example, a three-second VCG may have three cycles, and each cycle may be delimited by the times of the positive crossings along the x-axis. Alternatively, the cycles may be delimited by crossings along the y-axis or z-axis. In addition, cycles may be defined by negative crossings. Thus, in some embodiments, the component may generate training data from a single VCG based on various cycle definitions that are various combinations of positive crossings and negative crossings with the cycles for all the axes being defined by crossings on one of the x-axis, y-axis, and z-axis or the cycles for each defined by crossings on that axis. Moreover, the training data may include cycles identified based on all possible cycle definitions or a subset of the cycle definition. For example, the training data may include, for each axis, a cycle defined by positive crossings of the x-axis, negative crossings of the y-axis, and positive crossings of that axis itself. Cycles definitions may also be defined by the timing of electrical events derived from the values stored in the EM mesh. For example, a point or set of points in the mesh may periodically cross voltage thresholds signifying electrical activation and deactivation. Thus, a cycle may be defined by activation-deactivation, or successive activation-activation or deactivation-deactivation intervals corresponding to a point or set of points within the mesh. The resulting timings of these intervals can be co-localized to the ECG or VCG for cycles identification. In block 208, the component labels the EM data based on the source configuration (e.g., a source location). When cycles are identified, the component may label each cycle with the same label. For example, the component may label the identified cycles with the same rotor location. In block 209, the component adds the EM data along with the label to the training data and then loops to block 205 to select the next EM output. In block 210, the component trains the classifier using the training data and then completes.

Figure 3:
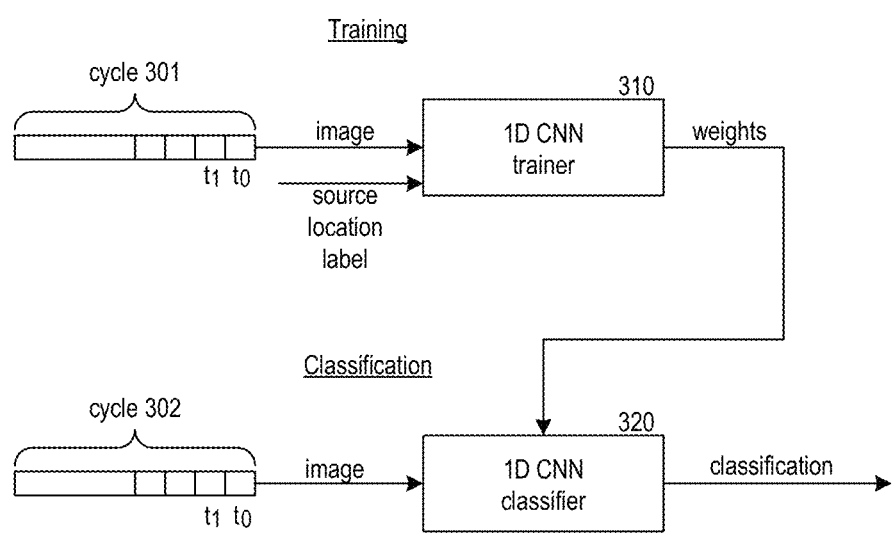
FIG. 3 is a block diagram that illustrates training and classifying using a convolutional neural network in some embodiments.

FIG. 3 is a block diagram that illustrates training and classifying using a convolutional neural network in some embodiments. The convolutional neural network may be one-dimensional in the sense that it inputs an image that is a single row of pixels with each pixel having a red, green, and blue ("RGB") value. The MLMO system sets the values of the pixels based on the voltages of a VCG of the training data. The image has the same number of pixels as vectors of a VCG of the training data. The MLMO system sets the red, green, and blue values of a pixel of the image to the x, y, and z values of the corresponding vector of the VCG. For example, if a cycle of a VCG is 1 second long, and the VCG has a vector for each millisecond, then the image is 1 by 1000 pixels. The one-dimensional convolutional neural network ("1D CNN") trainer 310 learns the weights of activation functions for the convolutional neural network using the training data 301. To generate a classification for a patient, the MLMO system provides the VCG 302 for the patient as a one-dimensional image. The 1D CNN 320 then classifies the VCG based on the weights and outputs the classification, such as rotor location.

CNNs are a type of neural network that has been developed specifically to process images. A CNN may be used to input an entire image and output a classification of the image. For example, a CNN can be used to automatically determine whether a scan of a patient indicates the presence of an anomaly (e.g., tumor). The MLMO system considers the derived EM data to be a one-dimensional image. A CNN has multiple layers such as a convolution layer, a rectified linear unit ("ReLU") layer, a pooling layer, a fully connected ("FC") layer, and so on. Some more complex CNNs may have multiple convolution layers, ReLU layers, pooling layers, and FC layers.

A convolution layer may include multiple filters (also referred to as kernels or activation functions). A filter inputs a convolution window of an image, applies weights to each pixel of the convolution window, and outputs an activation value for that convolution window. For example, if the image is 256 by 256 pixels, the convolution window may be 8 by 8 pixels. The filter may apply a different weight to each of the 64 pixels in a convolution window to generate the activation value also referred to as a feature value. The convolution layer may include, for each filter, a node (also referred to as a neuron) for each pixel of the image assuming a stride of one with appropriate padding. Each node outputs a feature value based on a set of weights for the filter that are learned during a training phase for that node. Continuing with the example, the convolution layer may have 65,536 nodes (256*256) for each filter. The feature values generated by the nodes for a filter may be considered to form a convolution feature map with a height and width of 256. If an assumption is made that the feature value calculated for a convolution window at one location to identify a feature or characteristic (e.g., edge) would be useful to identify that feature at a different location, then all the nodes for a filter can share the same set of weights. With the sharing of weights, both the training time and the storage requirements can be significantly reduced. If each pixel of an image is represented by multiple colors, then the convolution layer may include another dimension to represent each separate color. Also, if the image is a 3D image, the convolution layer may include yet another dimension for each image within the 3D image. In such a case, a filter may input a 3D convolution window.

The ReLU layer may have a node for each node of the convolution layer that generates a feature value. The generated feature values form a ReLU feature map. The ReLU layer applies a filter to each feature value of a convolution feature map to generate feature values for a ReLU feature map. For example, a filter such as max(0, activation value) may be used to ensure that the feature values of the ReLU feature map are not negative.

The pooling layer may be used to reduce the size of the ReLU feature map by downsampling the ReLU feature map to form a pooling feature map. The pooling layer includes a pooling function that inputs a group of feature values of the ReLU feature map and outputs a feature value. For example, the pooling function may generate a feature value that is an average of groups of 2 by 2 feature values of the ReLU feature map. Continuing with the example above, the pooling layer would have 128 by 128 pooling feature map for each filter.

The FC layer includes some number of nodes that are each connected to every feature value of the pooling feature maps. For example, if an image is to be classified as being a cat, dog, bird, mouse, or ferret, then the FC layer may include five nodes whose feature values provide scores indicating the likelihood that an image contains one of the animals. Each node has a filter with its own set of weights that are adapted to the type of the animal that the filter is to detect.

In the following, the MLMO system is described in reference to the following data structures. The brackets indicate an array. For example, VCG[2].V[5].x represents the voltage for the x-axis for the fifth time interval in the second VCG. The data structures are further described below when first referenced.

VCG data structures
VCG[ ]
   size
   V[ ]
      x
      y
      z
   nVCG
      V[ ]
         x
         y
         z
Cycles data structure
C
C[ ]
   start
   end
Training data structure
TD
TD[ ]
   nVCG[ ]
   label(s)

Figure 4:
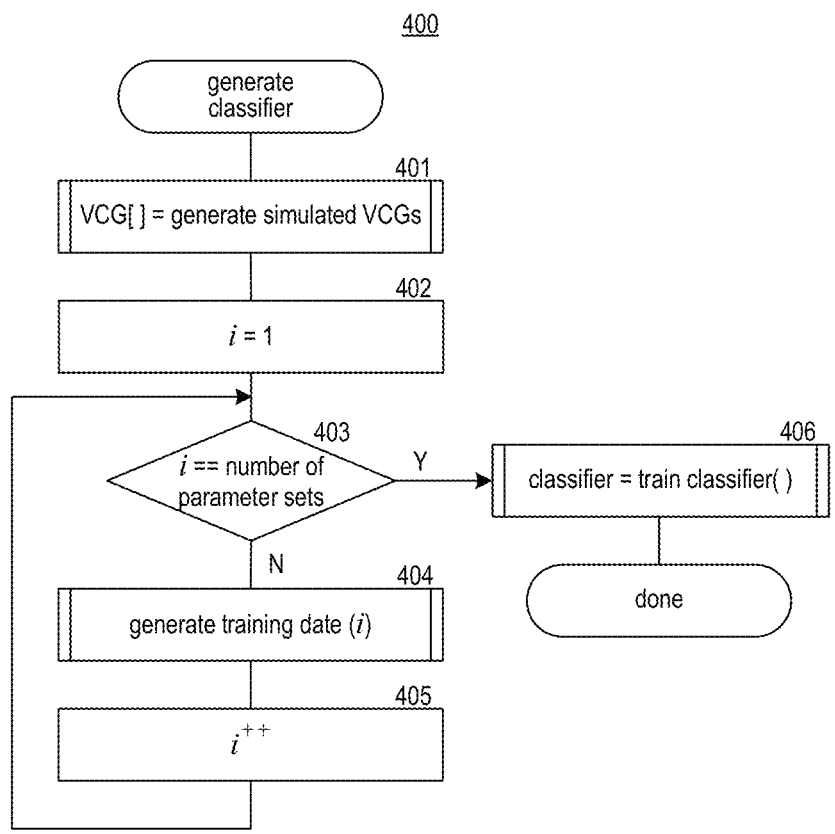
FIG. 4 is a flow diagram that illustrates processing of a generate classifier component of the MLMO system in some embodiments.

FIG. 4 is a flow diagram that illustrates detailed processing of the generate classifier component of the MLMO system in some embodiments. The generate classifier component 400 is invoked to generate a classifier. In block 401, the component invokes a generate simulated VCGs component to simulate VCGs (VCG[ ]) for a variety of parameter sets. In blocks 402-405, the component loops, generating the training data for each simulation. In block 402, the component sets an index i to 1 for indexing the parameter sets. In decision block 403, if index i is equal to the number of parameter sets, then all the training data has been generated and the component continues at block 406, else the component continues at block 404. In block 404, the component invokes a generate training data component, passing an indication of the indexed parameter set. In block 405, the component increments index i and then loops to block 403. In block 406, the component invokes a train classifier component to train the classifier based on the generated training data and then completes.

Figure 5:
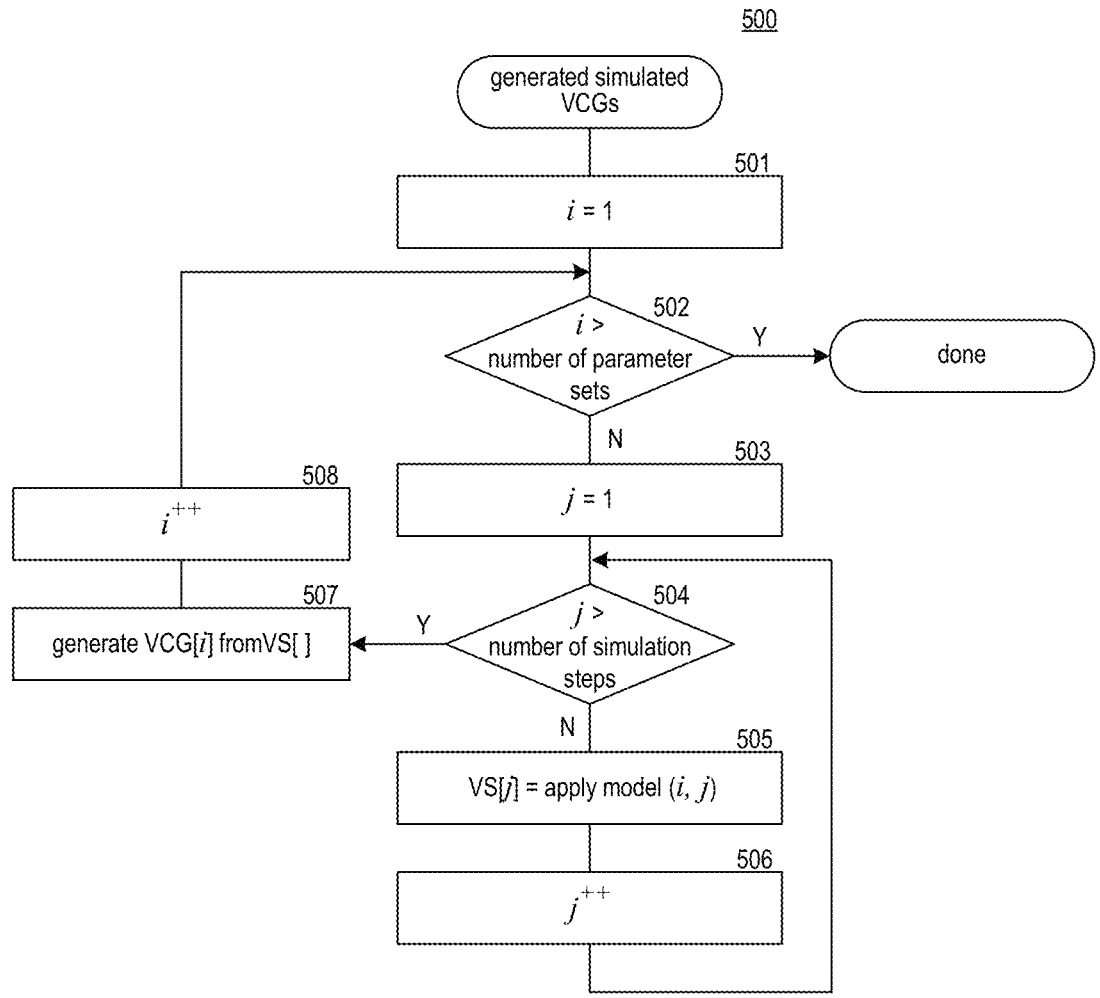
FIG. 5 is a flow diagram that illustrates the processing of a generate simulated VCGs component of the MLMO system in some embodiments.

FIG. 5 is a flow diagram that illustrates the processing of a generate simulated VCGs component of the MLMO system in some embodiments. The generate simulated VCGs component 500 is invoked to generate a simulated VCG for each parameter set. In block 501, the component sets an index i to 1 for indexing through the parameter sets. In decision block 502, if index i is greater than the number of parameter sets, then the component completes, else the component continues at block 503. In block 503, the component sets an index j to 1 for indexing through the simulation steps. In decision block 504, if index j is greater than the number of simulation steps, then the simulation for the indexed parameter set is complete and the component continues at block 507, else the component continues at block 505. In block 505, the component applies the computational model based on the indexed parameter set and the indexed simulation step to generate a voltage solution (VS[j]) for the indexed simulation step. In block 506, the component increments index j and then loops to block 504 to process the next simulation step. In block 507, the component generates a VCG (VCG[i]) for the indexed parameter set from the voltage solution (VS[ ]) that was calculated for the parameter set. In block 508, the component increments index i and then loops to block 502 to process the next parameter set.

Figure 6:
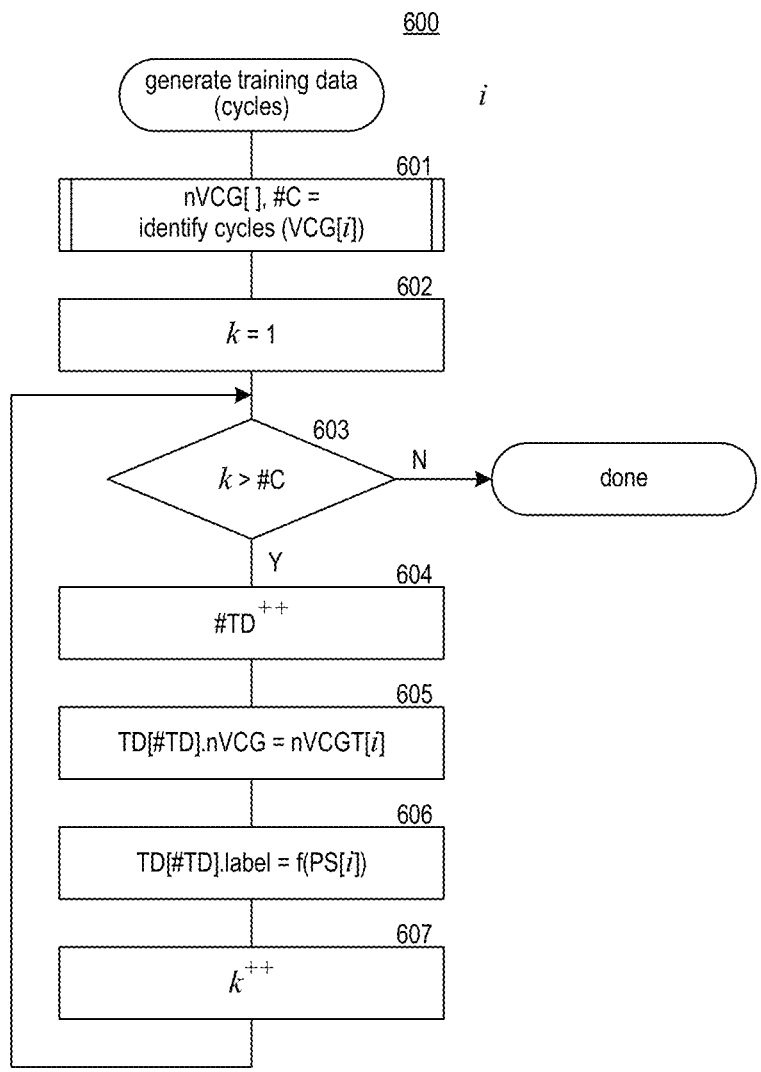
FIG. 6 is a flow diagram that illustrates the processing of a generate training data component for cycles of the MLMO system in some embodiments.

FIG. 6 is a flow diagram that illustrates the processing of a generate training data component for cycles of the MLMO system in some embodiments. The generate training data component 600 is invoked, passing an index i, that indexes a VCG generated for a parameter set and generates the training data from the VCG. In block 601, the component invokes an identify cycles component, passing an indication of the indexed VCG (VCG[i]) and receiving a normalized VCG (nVCG[ ]) for each cycle along with a count (#C) of the cycles that were identified. In block 602, the component sets an index k to 1 for indexing through the cycles. In decision block 603, if index k is greater than the count of the cycles, then the training data for all the cycles of the indexed VCG has been generated and the component completes, else the component continues at block 604. In block 604, the component increments a running count (#TD) of the training data (TD) that is used as an index into the training data. In block 605, the component sets the normalized nVCG of the indexed training data (TD[#TD].nVCG) to the portion of the VCG specified by the indexed cycle. The component extracts the portion from the x-axis, y-axis, and z-axis as defined by the start and end points of the cycle. In block 606, the component sets the label(s) of the indexed training data based on the function of the indexed parameter set (e.g., rotor location). In block 607, the component increments index k to index to the next cycle and then loops to block 603 to process the next cycle.

Figure 7:
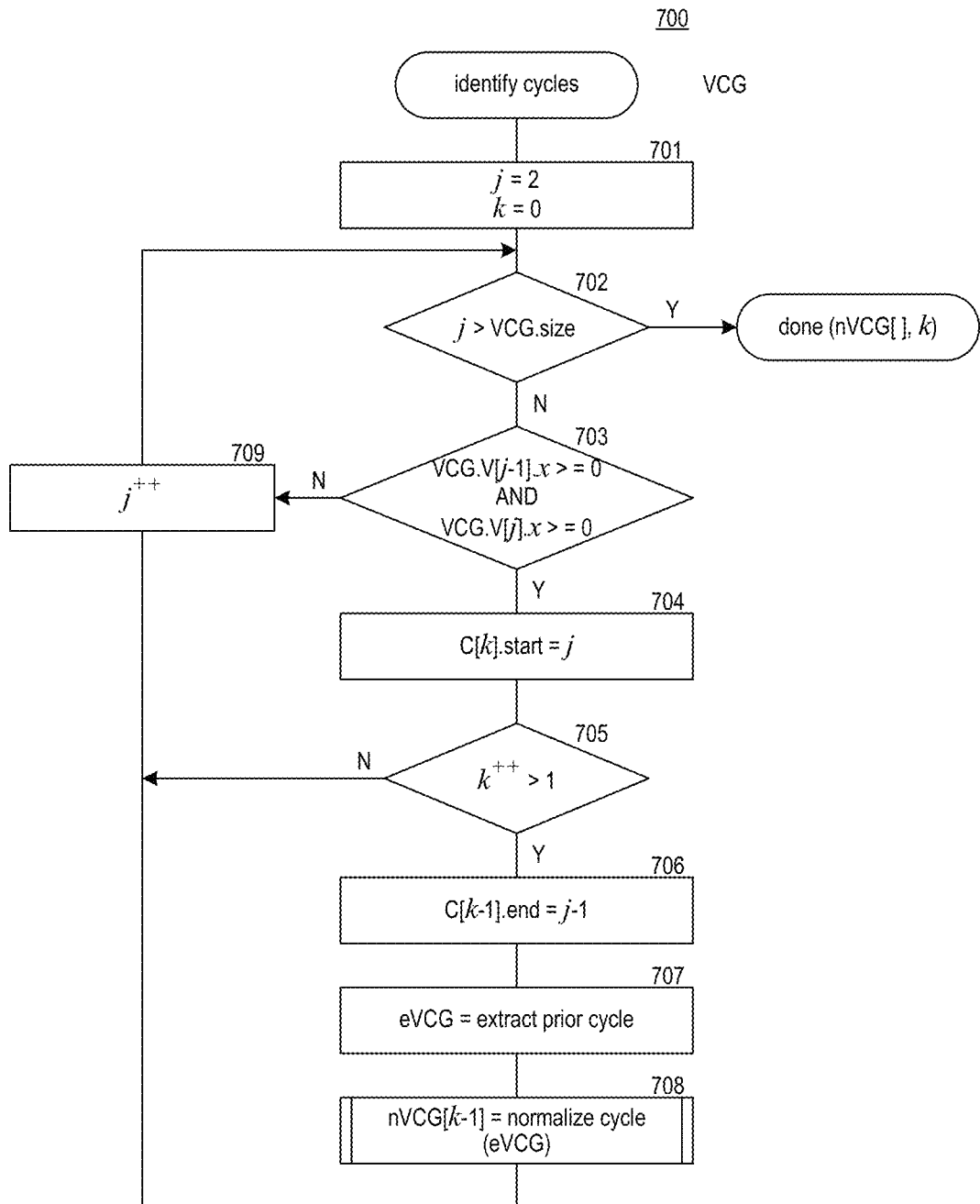
FIG. 7 is a flow diagram that illustrates the processing of an identify cycles component of the MLMO system in some embodiments.

FIG. 7 is a flow diagram that illustrates the processing of an identify cycles component of the MLMO system in some embodiments. The identify cycles component 700 is invoked to identify the cycles within a VCG and provides the normalized VCGs (nVCG[ ]) for the cycles. In block 701, the component initializes an index j to 2 for indexing through the VCG and sets an index k to 0 for indexing through the identified cycles. In decision block 702, if index j is greater than the size of the VCG, then the component has identified all the cycles and the component completes, providing the normalized nVCG, else the component continues at block 703. In block 703, if the prior voltage of the x-axis of the VCG (VCG.V[J−1].x) is greater than or equal to zero and the indexed voltage of the x-axis of the VCG (VCG.V[J].x) is less than zero (i.e., a negative crossing of the x-axis), then the start of a possible cycle has been identified and the component continues at block 704 to identify the cycle, else the component continues at block 709. In block 704, the component sets the start of the indexed cycle (C[k].start) equal to index j. In decision block 705, if at least one cycle has already been identified, then the end of the prior cycle is known and the component increments index k and continues at block 706, else the component increments index k and continues at block 709. In block 706, the component sets the end of the prior cycle to index j−1. In block 707, the component extracts the VCG (eVCG) for the prior indexed cycle delimited by the start and the end of the prior cycle. In block 708, the component invokes a normalize cycle component, passing an indication of the extracted VCG (eVCG), and receives the normalized cycle (nVCG). In block 709, the component increments the index j for indexing through the VCG and loops to block 702.

Figure 8:
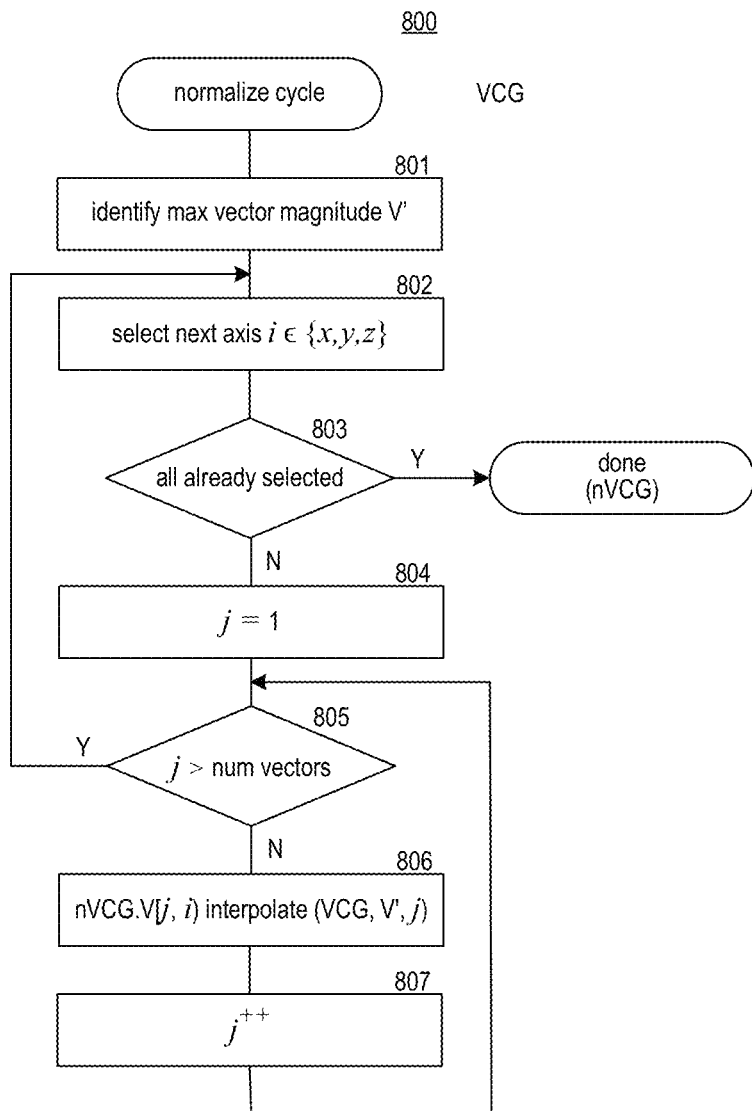
FIG. 8 is a block diagram that illustrates the processing of a normalize cycle component of the MLMO system in some embodiments.

FIG. 8 is a block diagram that illustrates the processing of a normalize cycle component of the MLMO system in some embodiments. The normalize cycle component 800 is invoked, passing an indication of the VCG of a cycle, and normalizes the cycle. In block 801, the component identifies the maximum vector magnitude V' of the vectors in the cycle. For example, a vector magnitude of a vector may be calculated by taking the square root of the sum of the squares of the x, y, and z values of the vector. In block 802, the component sets index i to index a next axis of the VCG. In decision block 803, if all the axes have already been selected, then the component completes, providing the normalized VCG, else the component continues at block 804. In block 804, the component initializes an index j to 1 for indexing through the vectors of a normalized cycle. In decision block 805, if index j is greater than the number of vectors of a normalized cycle, then the component loops to block 802 to select the next axis, else the component continues at block 806. In block 806, the component sets the normalized VCG for the indexed vector for the indexed axis to an interpolation of the passed VCG, the indexed vector, and the maximum vector magnitude V'. The interpolation effectively compresses or expands the VCG to the number of vectors in the normalized VCG and divides the x, y, and z values of the vector by the maximum vector magnitude V'. In block 807, the component increments the index j and then loops to block 805.

Figure 9:
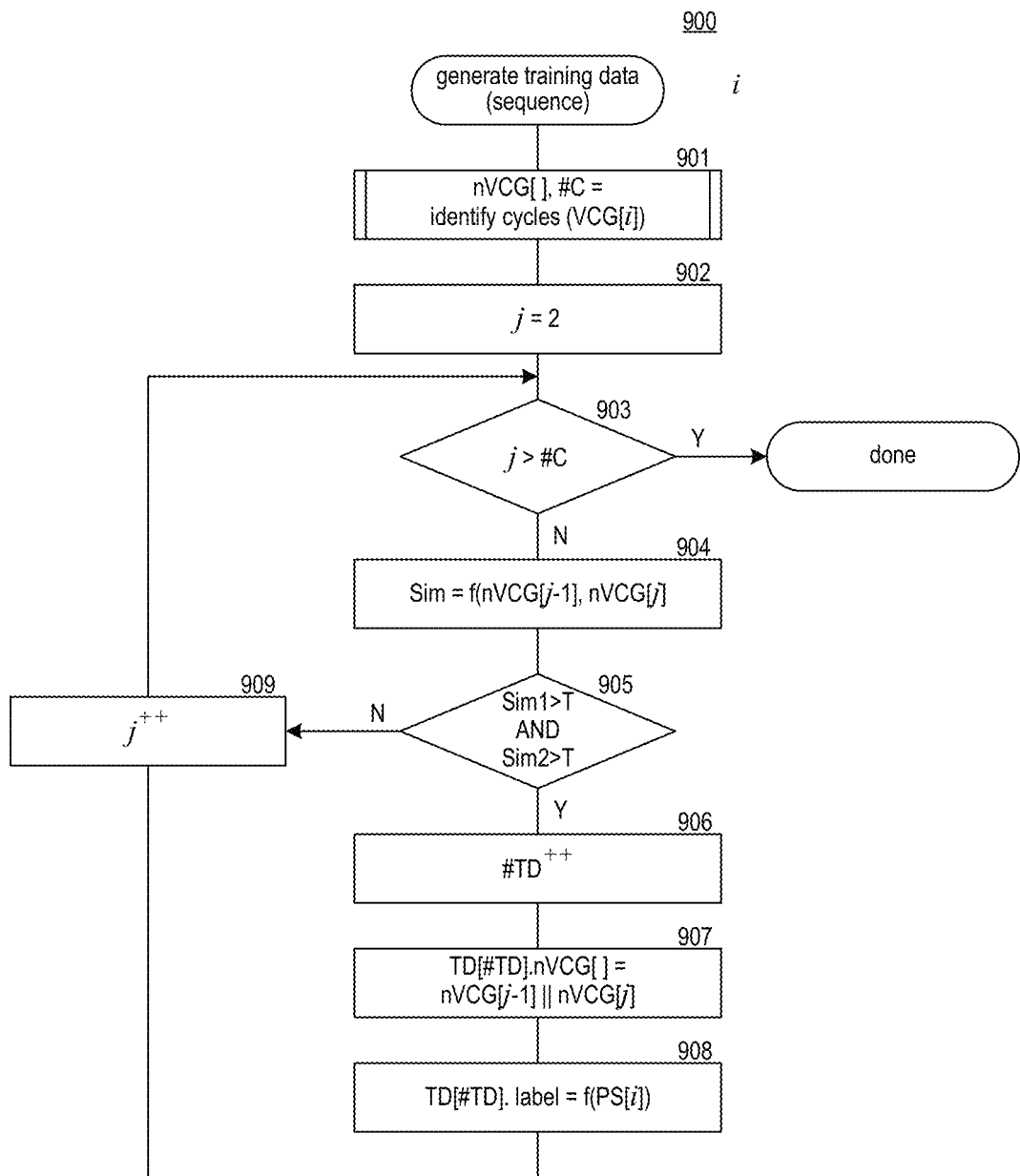
FIG. 9 is a flow diagram that illustrates processing of a generate training data for a sequence of similar cycles component of the MLMO system in some embodiments.

FIG. 9 is a flow diagram that illustrates processing of a generate training data for a sequence of similar cycles component of the MLMO system in some embodiments. The generate training data for a sequence of similar cycles component 900 is invoked to identify sequences of two consecutive cycles of the VCG indexed by the passed index i that are similar and generate training data based on the identified sequences of similar cycles. The cycles in a sequence are similar according to a similarity score that reflects the stability of the cycles. In block 901, the component invokes the identify cycles component to identify the cycles (nVCG[ ]) for the VCG. In block 902, the component sets an index j to 2 for indexing through the identified cycles. In decision block 903, if index j is greater than the number of identified cycles, then all the cycles have been indexed and then component completes, else the component continues at block 904. In block 904, the component generates a similarity score for the cycles indexed by j−1 and j. The similarity score may be based on, for example, a cosine similarity, a Pearson correlation, and so on. In decision block 905, if similarity score is above a similarity score threshold (T) indicating similar cycles, then a sequence of similar cycles has been identified and the component continues at block 906, else the component continues at block 909. In block 906, the component increments a running count (#TD) of the training data. In block 907, the component sets the training data to the sequence of similar cycles. In block 908, the component sets the label for the training data to a label derived from the parameter set (PS[i]) used to generate the VCG and then continues at block 909. In block 909, the component increments index i to select the next sequence of cycles and loops to block 903.

Figure 10:
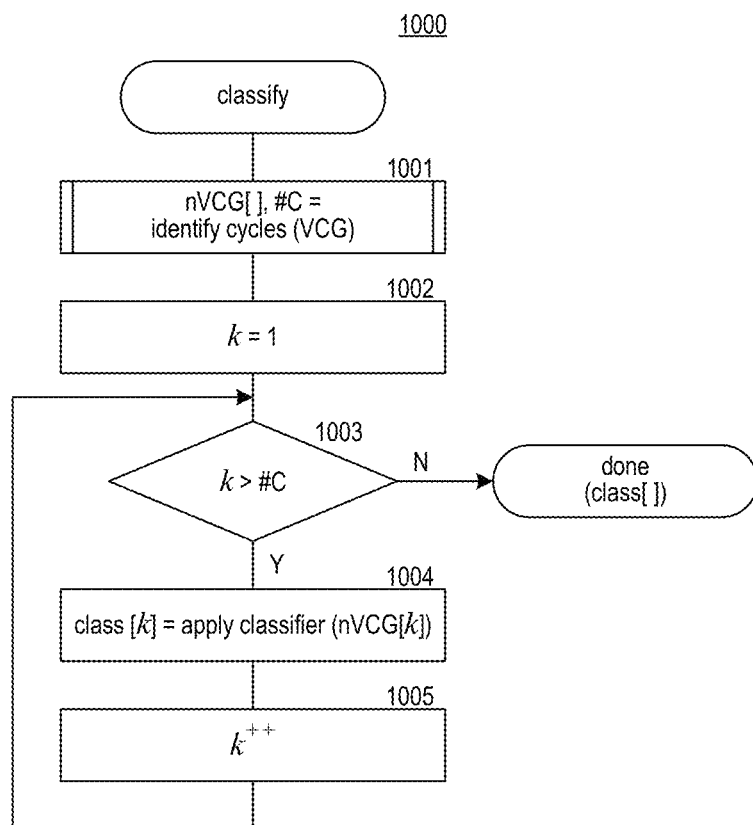
FIG. 10 is a flow diagram that illustrates the processing of a classify component of the MLMO system in some embodiments.

FIG. 10 is a flow diagram that illustrates the processing of a classify component of the MLMO system in some embodiments. The classify component 1000 is invoked, passing a VCG derived from a patient, and outputs a classification. In block 1001, the component invokes the identify cycles component, passing an indication of the VCG, and receives the normalized VCGs for the cycles and a count of cycles. In block 1002, the component sets an index k to 1 for indexing through the cycles. In decision block 1003, if index k is greater than the number of cycles, then the component completes with the classifications, else the component continues at block 1004. In block 1004, the component applies the classifier to the indexed cycle to generate the classification. In block 1005, the component increments the index and then loops to block 1003 to process the next cycle. A different classification (e.g., different rotor location) may be generated for each cycle. In such a case, the overall classification may be derived from the combination of the different classifications (e.g., average of the rotor locations).

Model Library Generation System

A method and system for generating a model library of models of an EM source within a body is provided. In some embodiments, a model library generation ("MLG") system generates models based on source configurations with configuration parameters that include anatomical parameters and electrophysiology parameters for the EM source. The anatomical parameters specify dimensions or overall geometry of the EM source. When the EM source is a heart, then the models may be arrhythmia models based on anatomical parameters that may include any subset of the group consisting of thickness of a heart wall (e.g., thickness of the endocardium, myocardium, and epicardium), dimensions of chambers, diameters, ventricular orientation in the chest, torso anatomy, fiber architecture, the location(s) of scar, fibrosis, and pro-arrhythmia substrate, scar shape and so on. The geometry of a heart may be measured when maximal chamber volume and minimal wall thickness and activation occur. With normal sinus, activation occurs at the time of the end-diastolic portion of a beat. With an arrhythmia, activation may occur at a different time during a beat. Therefore, the MLG system may allow the geometry to be specified at times other than the end-diastolic portion. The torso anatomy may be used tailor the EM output based on the size, shape, composition, and so on of the torso. The electrophysiology parameters are the non-anatomical parameters that may include any subset of the group consisting of inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, and other normal and pathophysiologic feature distributions, action potential dynamics, conductivities, arrhythmia source location, and so on. The configuration parameters that are selected for a simulation may be based on the machine learning algorithm employed. For example, the fiber architecture parameter may be selected for a convolutional neural network, but not for other types of neural networks. The MLG system generates source configurations from which the arrhythmia models are generated. For each source configuration, the MLG system generates an arrhythmia model that includes a mesh and model parameter such as variable weights for the arrhythmia model. The MLG system generates the mesh based on the anatomical parameters. After the computational mesh is generated, the MLG generates model parameters of the arrhythmia model at point within the mesh based on the electrophysiology parameters of that source configuration. The electrophysiology parameters control the modeling of, for example, the electromagnetic propagation at that point based on the electrophysiology parameters. The collection of arrhythmia models forms an arrhythmia model library. The MLMO system can then generate a modeled EM output for each arrhythmia model and use the modeled EM outputs to train a classifier. The arrhythmia model library may be used for other purposes such as studying the efficacy of different types of ablations.

In some embodiments, the MLG system generates sets of anatomical parameters for the heart, with each set having a value (e.g., scalar, vector, or tensor) for each anatomical parameter. A set of anatomical parameters specifies an anatomy of a heart. The MLG system generates simulated anatomies that are based on a set of seed anatomies (specifying values for the dimensions of the EM source) and sets of weights that include a weight for each seed anatomy. The seed anatomies may also include values for features derived from the specified values such as the mass, the volume, ratios of length and width, the sphericity, and so on of a chamber. The seed anatomies may represent extreme anatomies found in patients. For example, the seed anatomies may be generated from ultrasound, computed tomography, and magnetic resonance imaging scans of patients who have extreme heart conditions such as an enlarged right ventricle, a very thick or thin endocardium, and so on. The MLG system generates a simulated anatomy for each set of weights. Each weight in a set of weights indicates the contribution of the anatomical parameters of a seed anatomy to a simulated anatomy. For example, if four seed anatomies are specified, then the weights may be 0.4, 0.3, 0.2, and 0.1. The MLG system sets the value of each anatomical parameter for a simulated anatomy for a set of weights to a weighted average of the values of each anatomical parameter of the seed anatomies. The MLG system may use various techniques for generating the sets of weights, such as defining a fixed interval (e.g., 0.001), randomly selecting weights that add to 1.0, using a design-of-experiments technique, and so on. The MLG system may also validate the simulated anatomies based on comparison of the anatomical parameters to actual anatomical parameters of actual patients. For example, if the combination of a height, width, and depth of a heart chamber results in a volume that has not been seen in an actual patient (e.g., not found in a patient population), then the MLG system may discard that simulated anatomy as it is unlikely to appear in an actual patient.

In some embodiments, the MLG system may employ a bootstrapping technique to speed up the generating of the modeled EM output based on the arrhythmia models. Since a mesh for a left ventricle may have 70,000 vertices, a simulation to generate the modeled EM output for an arrhythmia model for the left ventricle would require the calculation of 70,000 values per EM mesh. If the simulation is for three seconds with a step size of 1 ms, then $70 \times 10^6$ values for the vertices would need to be calculated. If the arrhythmia model library includes a million arrhythmia models, then the number of values that need to be calculated would be $70 \times 10^{12}$. In addition, the calculation of a single value may involve many mathematical operations, and multiple values may be calculated for each vertex. To help reduce the number of values that need to be calculated, the MLG system effectively shares some of the values for the EM meshes generated for one simulation based on one arrhythmia model with another simulation that is based on another arrhythmia model. For example, when a simulation is started, it may take approximately one second before some of the values of the EM mesh have an appreciable effect on the values. For example, at the one-second point in simulations, the EM meshes for simulations based on arrhythmia models with the same source configuration except for scar or fibrosis or pro-arrhythmic substrate location may have very similar values. To reduce the number of values that need to be calculated, the MLG system groups together arrhythmia models with source configurations that are the same or nearly the same except for their scar or fibrosis or pro-arrhythmic substrate locations. The groupings may also not factor in conduction velocity and action potential parameters. The MLG system then runs the simulation for a representative arrhythmia model of the group (e.g., one without a scar or fibrosis or pro-arrhythmic substrate location). To run the simulations for the other arrhythmia models, the MLG system sets the values of the initial EM meshes to the values of the EM mesh at the one-second point in the simulation for the representative arrhythmia model. The MLG system then runs the other simulations for two seconds starting with the values of the initial EM mesh. The modeled EM output for each other arrhythmia model includes the EM meshes for the first second of the representative arrhythmia model and the EM meshes for the two seconds of that other arrhythmia model. In this way, the MLG system can significantly reduce the number of values (e.g., approximately by one-third) that need to be calculated during some of the simulations, which can significantly speed up the generating of the model EM output or voltage solutions for an arrhythmia model library.

In some embodiments, the MLG system may employ other bootstrapping techniques to speed up the generating of modeled EM output. One bootstrapping technique may allow for rapid generation for different configuration parameters such as different geometries, different action potentials, and different conductivity parameters. For example, for a given focal or rotor source location and a set of set of other configuration parameters, a simulation may be run for two seconds. The EM mesh from that simulation is then modified based on a different geometry, or the model parameters are adjusted based on different action potentials or conductivity parameters. The simulation is then continued. It may take a second or so for the activation potentials to stabilize based on the different configuration parameters. Another bootstrapping technique speeds up the generation for a rotor anchored to a different scar location. For example, for a given anchoring scar location, the simulation may be run for two seconds. After the first second, the rotor may stabilize anchored to the scar location. During the second second, sufficient modeled EM output is simulated to generate a cardiogram. The EM mesh from that simulation is then modified to have the anchoring scar location moved nearby and possibly modified based on a different geometry. The simulation is then continued. The simulation will allow the rotor to detach from the prior anchoring scar location and attach to the new anchoring scar location. Once attached, the modeled EM output for the next second or so can be used to generate ECGs or VCGs. Also, rather than modifying the anchoring scar location, an ablation shape and pattern can be added to the EM mesh to simulate the effect of that ablation, or the configuration of the anchoring scar may be modified to rapidly simulate the effect of that configuration.

In some embodiments, the MLG system may speed up the generating of derived EM data that is derived from the modeled EM outputs generated for the arrhythmia models of the arrhythmia model libraries. The derived EM data may be a VCG (or other cardiogram) generated from a modeled EM output (e.g., 3,000 EM meshes). The MLG system may group together arrhythmia models with source configurations that have similar anatomical parameters. Each arrhythmia model in a group will thus have similar electrophysiology parameters and different anatomical parameters. The MLG system then runs the simulation for a representative arrhythmia model of the group. The MLG system, however, does not need to run the simulations for the other arrhythmia models in the group. To generate the VCG for one of the other arrhythmia models, the MLG system inputs the modeled EM output of the representative arrhythmia model and the anatomical parameters of the other arrhythmia model. The MLG system then calculates the VCG values for the other arrhythmia model based on the values of the modeled EM output with adjustments based on differences in the anatomical parameters of the representative arrhythmia model and the other source configuration. In this way, the MLG system avoids running any simulations except for the representative arrhythmia model of each group of arrhythmia models.

In some embodiments, the MLG system converts the arrhythmia models based on one polyhedral model to arrhythmia models based on another polyhedral model. Different finite-mesh problem solvers may be based on different polyhedral models. For example, one polyhedral model may be a hexahedral model, and another polyhedral model may be a tetrahedral model. With a hexahedral model, a mesh is filled with hexahedrons. With a tetrahedral model, a mesh is filled with tetrahedrons. If an arrhythmia model library is generated based on a hexahedral model, that arrhythmia library cannot be input to a tetrahedral problem solver. A separate arrhythmia model library based on a tetrahedral model could be generated based on the source configurations, but it would be computationally expensive to do so. To reduce this computational expense of generating a tetrahedral arrhythmia model library, the MLG system converts hexahedral arrhythmia models to tetrahedral arrhythmia models. To convert a tetrahedral arrhythmia model, the MLG system generates a surface representation of the tetrahedral arrhythmia model, for example, based on the surface faces of the mesh of the hexahedral arrhythmia model. The MLG system then populates the volume formed by the surface representation with tetrahedrons to generate a tetrahedral mesh. The MLG system then generates a value for each vertex of the tetrahedral mesh by interpolating the values of the vertices of the hexahedral mesh that are proximate to that vertex of the tetrahedral mesh. In this way, the MLG system can use an arrhythmia model library for one type of polyhedron to generate an arrhythmia model library for another type of polyhedron and avoid the computational expense of generating the arrhythmia model library for the other type of polyhedron from source configurations. The MLG system may also convert an arrhythmia model from one polyhedral model to another polyhedral model for display of the electromagnetic source. For example, the MLG system may run a simulation using a hexahedral ventricular mesh and then, for display, convert to a surface-triangle ventricular mesh to provide a more realistic looking display of the ventricle.

Figure 11:
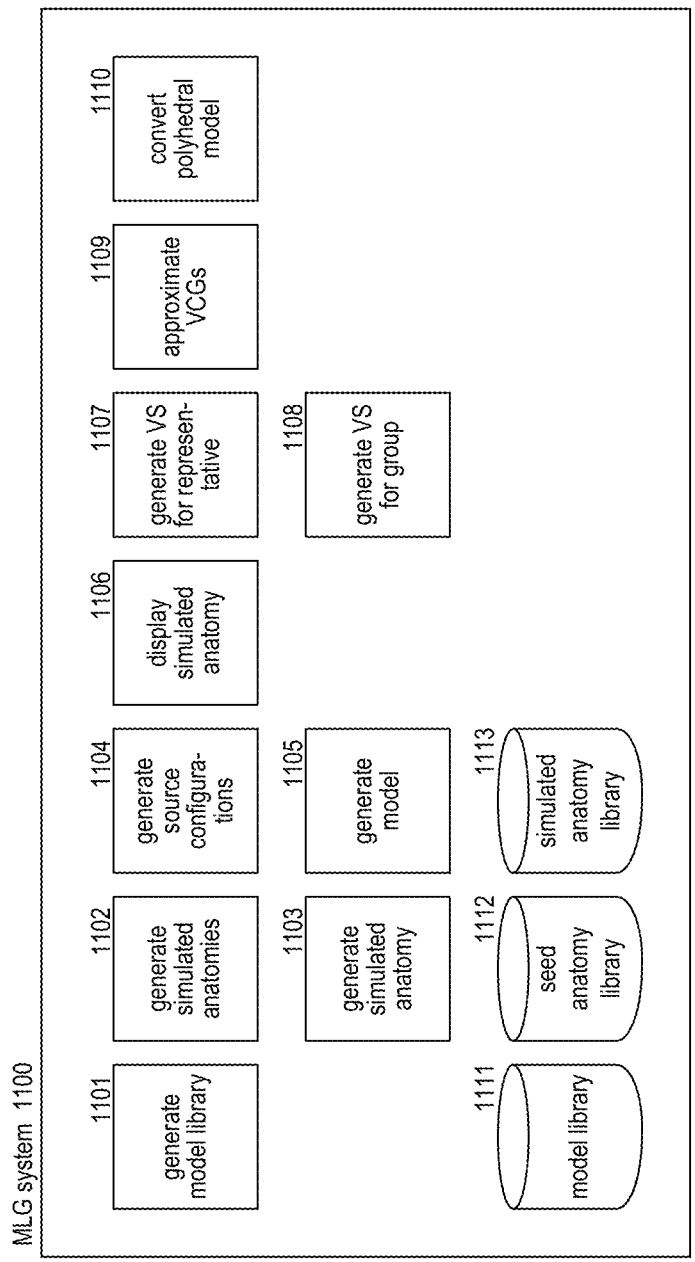
FIG. 11 is a block diagram illustrating components of the MLG system in some embodiments.

FIG. 11 is a block diagram illustrating components of the MLG system in some embodiments. The MLG system 1100 includes a generate model library component 1101, a generate simulated anatomies component 1102, a generate simulated anatomy component 1103, a generate source configurations component 1104, a generate model component 1105, a display simulated anatomy component 1106, a generate voltage solution for representative component 1107, a generate voltage solution for group component 1108, an approximate VCGs component 1109, and a convert polyhedral model component 1110. The MLG system also includes a model library 1111 that stores arrhythmia models, a seed anatomy library 1112, which stores seed anatomies (for example, of a heart), and a simulated anatomy library 1113, which stores simulated anatomies (for example, of a heart). The generate model library component controls the overall generation of the model library. The generate simulated anatomies component generates the simulated anatomies for various sets of weights by invoking the generate simulated anatomy component for each set of weights. The generate source configurations component generates various source configurations based on the simulated anatomies and possible values for electrophysiology parameters. The generate model component generates a model based on a source configuration. The display simulated anatomy component may provide an application programming interface or a user experience for specifying the sets of weights and viewing seed and simulated anatomies. The generate voltage solution for representative component generates a voltage solution for a representative source configuration of a group. The generate voltage solution for group component generates voltage solutions for source configurations in a group based on bootstrapping using the voltage solution for a representative source configuration. The approximate VCGs component generates an approximate VCG based on a voltage solution for similar source configuration but with different anatomical parameters. The convert polyhedral model component converts a hexahedral model to a tetrahedral model.

Figure 12:
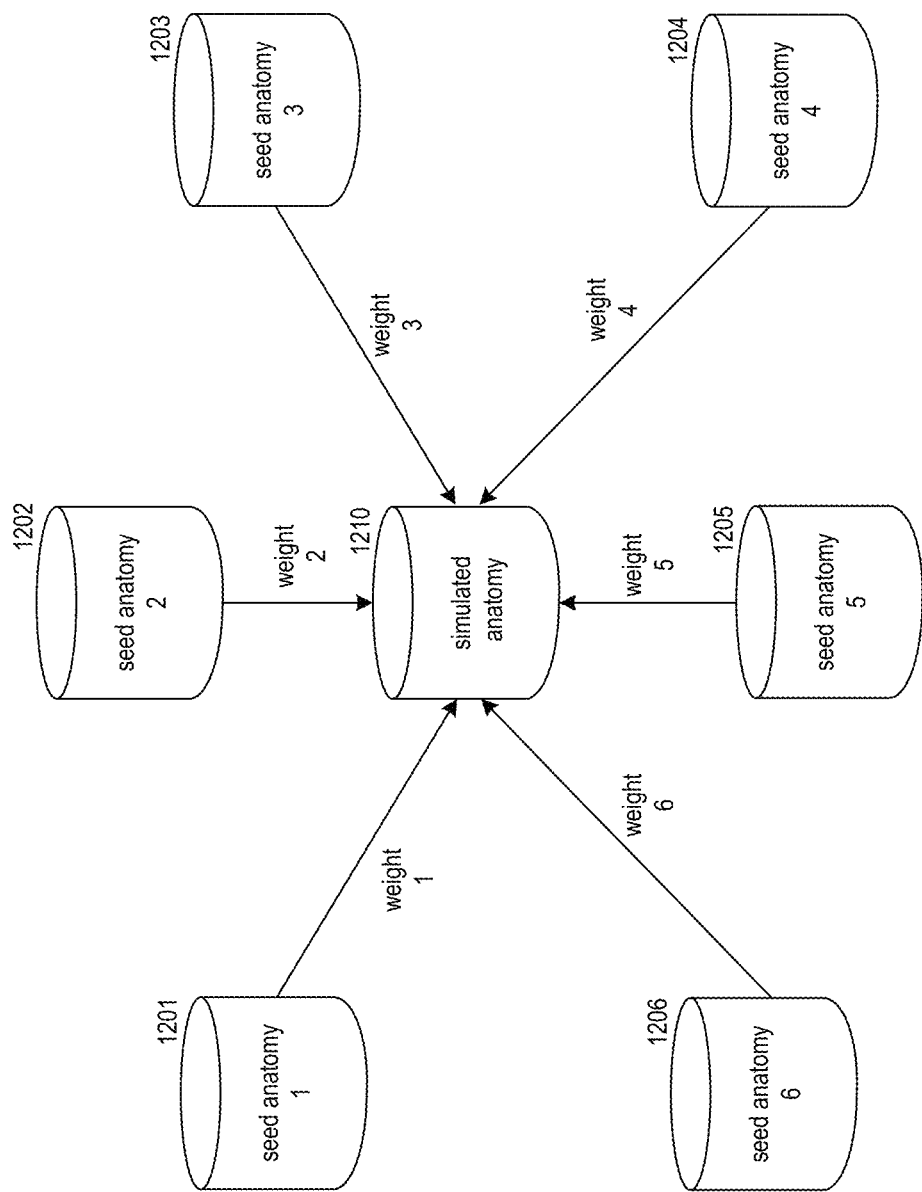
FIG. 12 is a block diagram that illustrates the generating of a simulated anatomy from seed anatomies.

FIG. 12 is a block diagram that illustrates the generating of a simulated anatomy from seed anatomies. In this example, seed anatomies 1201-1206 are used to generate a simulated anatomy 1210. Each seed anatomy has an associated weight that specifies the contribution of the seed anatomy to the simulated anatomy. The weights may sum to 1.0. In some embodiments, rather than a single weight for each seed anatomy, the MLG system may employ a weight for each anatomy parameter of the seed geometry. For example, the weights may include a weight for dimensions of a heart chamber, a weight for the thickness of a heart wall, and so on. The weights for an anatomy parameter of the seed anatomies may sum to 1.0. For example, the weights of seed anatomies 1201-1206 may be 0.1, 0.1, 0.1, 0.1, 0.3, and 0.3, respectively, for the dimensions of the left ventricle and 0.2, 0.2, 0.2, 0.2, 0.1, and 0.1, respectively, for the thickness of an endocardium, myocardium, and epicardium. Alternatively, the weights for the seed anatomies or an anatomical parameter of the seed anatomies need not sum to 1.0.

Figure 13:
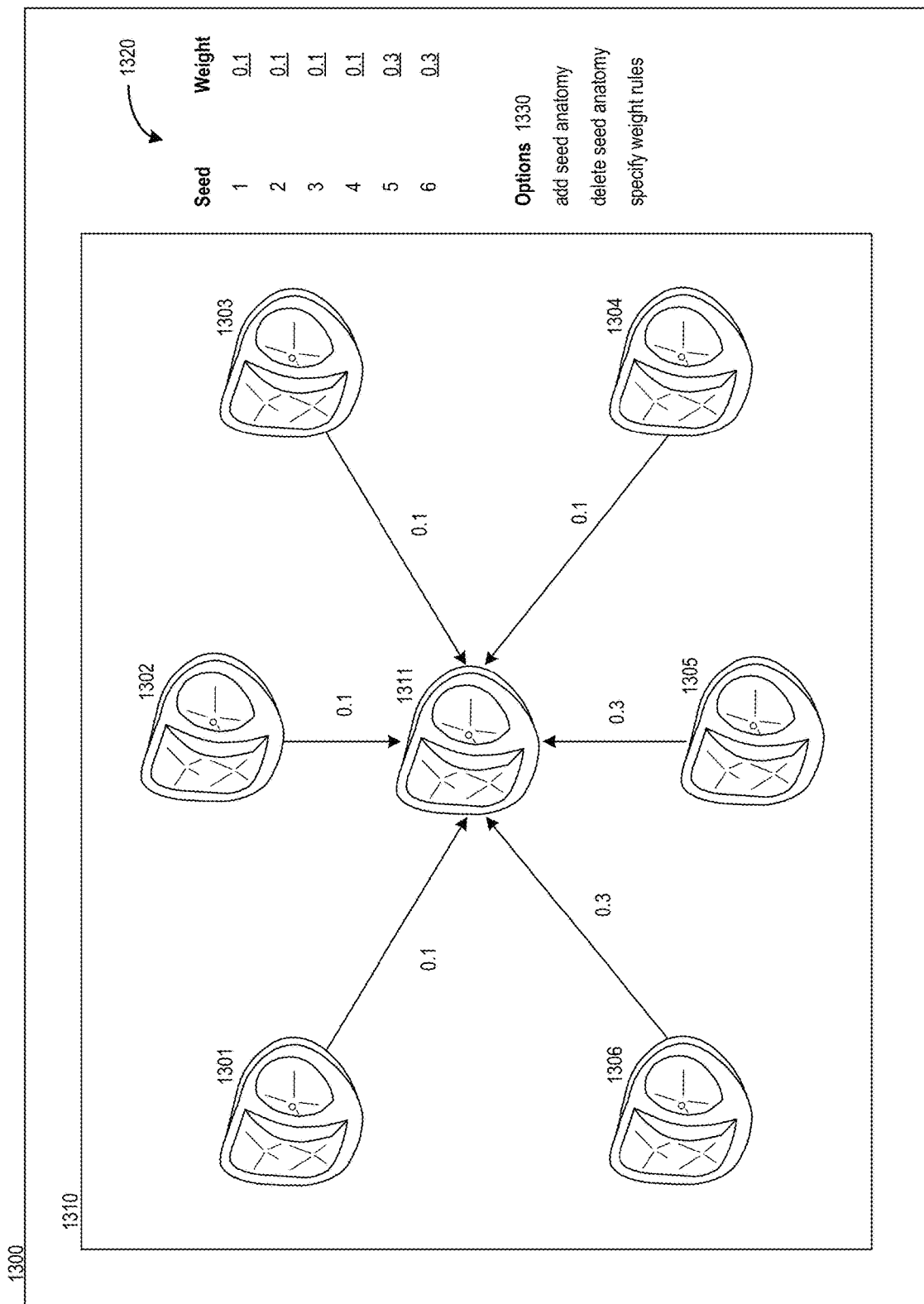
FIG. 13 is a display page that illustrates a user experience for viewing simulated anatomies in some embodiments.

FIG. 13 is a display page that illustrates a user experience for viewing simulated anatomies in some embodiments. A display page 1300 includes a graphics area 1310, a weights area 1320, and an options area 1330. The graphics area displays a graphic of each seed anatomy of a heart and the weights along with a graphic of the simulated anatomy of the heart based on those weights. A user can use the weights area to specify the weight of each seed anatomy. The user may use the options area to add additional seed anatomies, delete a seed anatomy, and specify weight rules based on a user interface (not illustrated) for each option. The MLG system may specify a data structure for storing the anatomical parameters of a seed anatomy. A user can upload the data structure when adding a new seed anatomy. The MLG system may also allow a user to create a library of seed anatomies that can be used to generate simulated anatomies. A weight rule specifies how to generate sets of weights for a library of simulated anatomies. For example, a weight rule may specify to generate every combination of sets of unnormalized weights that range between 0.0 and 1.0 in increments of 0.2 and then normalize the weights so that the weights in each set of weights sums to 1.0. Given this weight rule and six seed anatomies, $5 \times 10^6$ sets of weights are specified. The graphics may be generated using a 3D computer graphics software toolset such as Blender.

Figure 14:
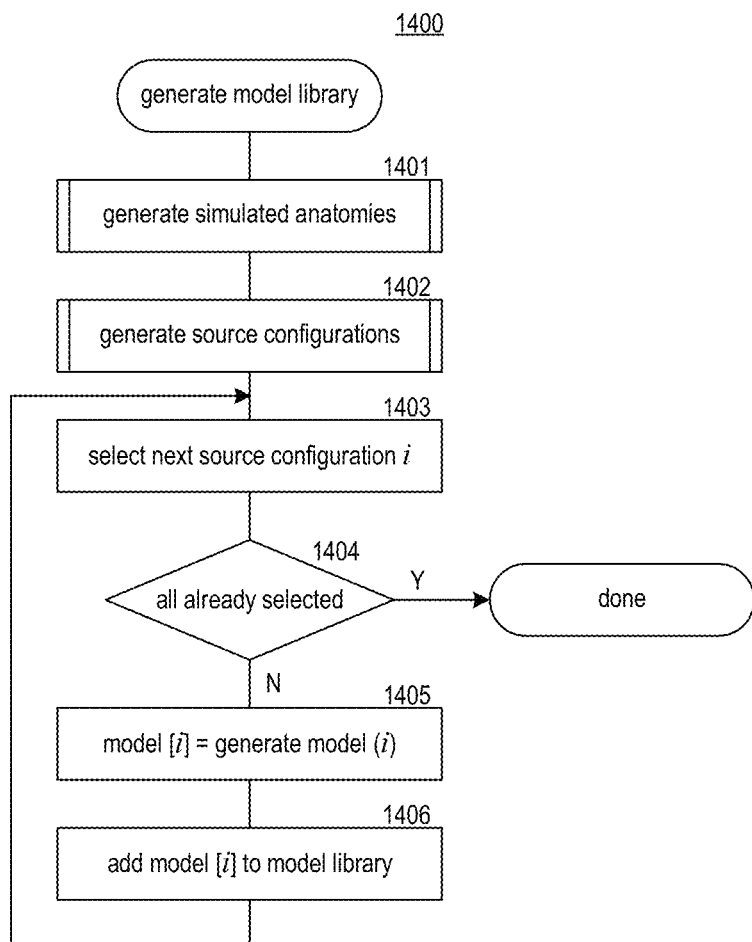
FIG. 14 is a flow diagram that illustrates the processing of a generate model library component of the MLG system in some embodiments.

FIG. 14 is a flow diagram that illustrates the processing of a generate model library component of the MLG system in some embodiments. The generate model library component 1400 is invoked to generate a model library, such as an arrhythmia model library, based on seed anatomies and, for each model, a set of weights for the seed anatomies for generating the anatomical parameters along with electrophysiology parameter specifications that specify the range of values for each electrophysiology parameter. The component generates source configurations from combinations of the anatomical parameters and electrophysiology parameters. In block 1401, the component invokes a generate simulated anatomies component to generate the simulated anatomies from the seed anatomies. In block 1402, the component invokes a generate source configurations component to generate the source configurations based on the anatomical parameters of the simulated anatomies and the electrophysiology parameter specifications. In blocks 1403-1406, the component loops, generating a model for each source configuration. In block 1403, the component selects the next source configuration i. In decision block 1404, if all the source configurations have already been selected, then the component completes, else the component continues at block 1405. In block 1405, the component invokes a generate model component, passing an indication of the source configuration i, to generate a model (model[i]) for that source configuration. In block 1406, the component adds the generated model to the model library and then loops to block 1403 to select the next source configuration.

Figure 15:
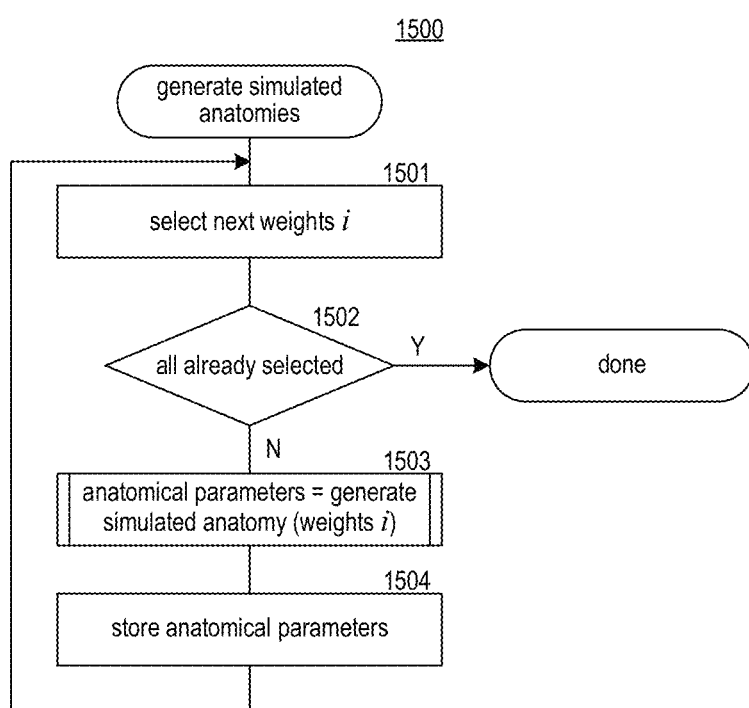
FIG. 15 is a flow diagram that illustrates the processing of a generate simulated anatomies component of the MLG system in some embodiments.

FIG. 15 is a flow diagram that illustrates the processing of a generate simulated anatomies component of the MLG system in some embodiments. The generate simulated anatomies component 1500 is invoked to generate simulated anatomies based on seed anatomies and associated sets of weights. In block 1501, the component selects the next set of weights i. In decision block 1502, if all the sets of weights have already been selected, then the component completes, else the component continues at block 1503. In block 1503, the component invokes the generate simulated anatomy component, passing an indication of the selected set of weights i and receiving an indication of the anatomical parameters for the simulated anatomy. In block 1504, the component stores the anatomical parameters and then loops to block 1501 to select the next set of weights.

Figure 16:
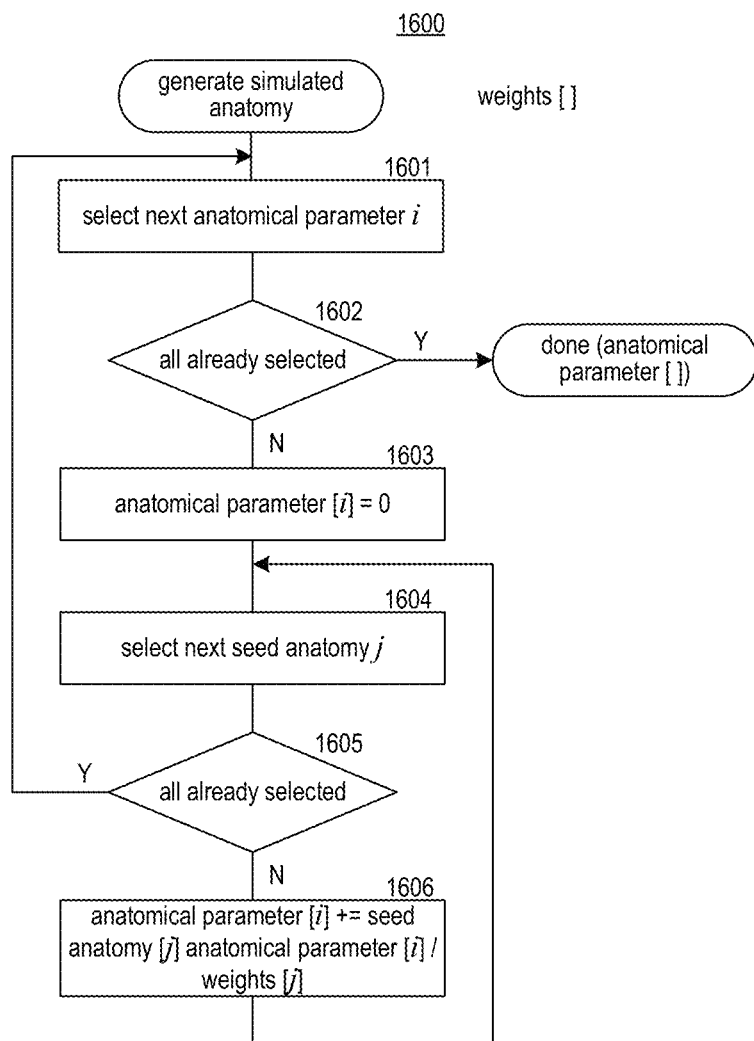
FIG. 16 is a flow diagram that illustrates the processing of a generate simulated anatomy component of the MLG system in some embodiments.

FIG. 16 is a flow diagram that illustrates the processing of a generate simulated anatomy component of the MLG system in some embodiments. The generate simulated anatomy component 1600 is invoked, passing an indication of a set of weights, and generates a simulated anatomy based on that set of weights. In block 1601, the component selects the next anatomical parameter i. In decision block 1602, if all the anatomical parameters have already been selected, then the component returns an indication of the anatomical parameters for the simulated anatomy, else the component continues at block 1603. In block 1603, the component initializes the selected anatomical parameter i. In blocks 1604-1606, the component loops, adjusting the selected anatomical parameter based on the weights and the value for that anatomical parameter for each seed anatomy. In block 1604, the component selects the next seed anatomy j. In decision block 1605, if all the seed anatomies have already been selected, then the component loops to block 1601 to select the next anatomical parameter, else the component continues at block 1606. In block 1606, the component sets the selected anatomical parameter i to the sum of the selected anatomical parameter i and that anatomical parameter i for the selected seed anatomy j divided by the weight for the selected seed anatomy. The component then loops to block 1604 to select the next seed anatomy.

Figure 17:
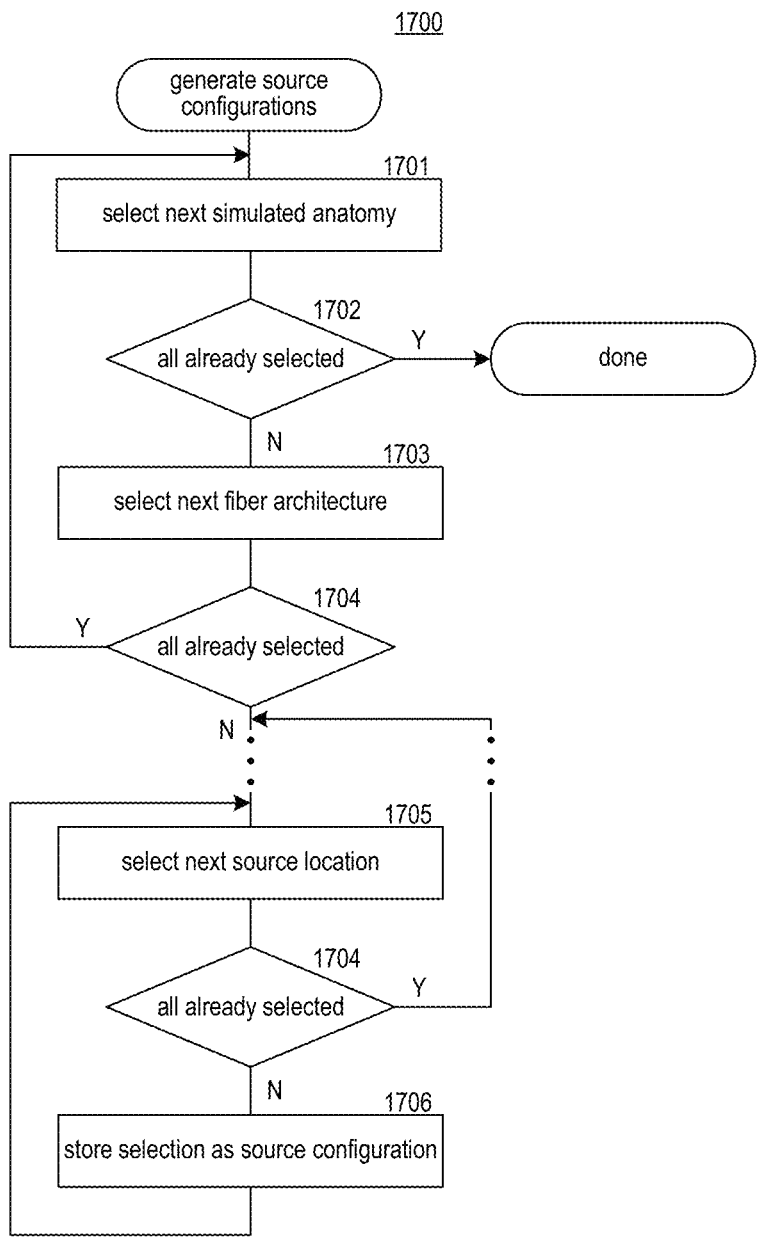
FIG. 17 is a flow diagram that illustrates the processing of a generate source configurations component of the MLG system in some embodiments.

FIG. 17 is a flow diagram that illustrates the processing of a generate source configurations component of the MLG system in some embodiments. The generate source configurations component 1700 is invoked to generate source configurations for use in generating a model library. A source configuration is specified by a simulated anatomy and a combination of values of anatomical parameters. In block 1701, the component selects a next simulated anatomy. In decision block 1702, if all the simulated anatomies have already been selected, then the component completes, else the component continues at block 1703. In blocks 1703-1707, the component loops, selecting sets of anatomical parameters for the selected simulated anatomy. In block 1703, the component selects the next value for the fiber architecture anatomical parameter. In decision block 1704, if all the values for the fiber architecture anatomical parameter have already been selected for the selected simulated anatomy, then all the source configurations for the selected simulated anatomy have been generated and the component loops to block 1701 to select the next simulated anatomy, else the component continues to select a value for each of the other anatomical parameters, as illustrated by the ellipsis. In block 1705, the component selects the next source location for the selected simulated anatomy and set of values for the other anatomical parameters. In decision block 1706, if all the source locations have already been selected for the selected simulated anatomy and set of values for the other anatomical parameters, then the component loops to block 1705 to select a new set of values. In block 1707, the component stores an indication of the selected simulated anatomy and the set of selected values for the anatomical parameters as a source configuration and then loops to block 1705 to select the next source location.

Figure 18:
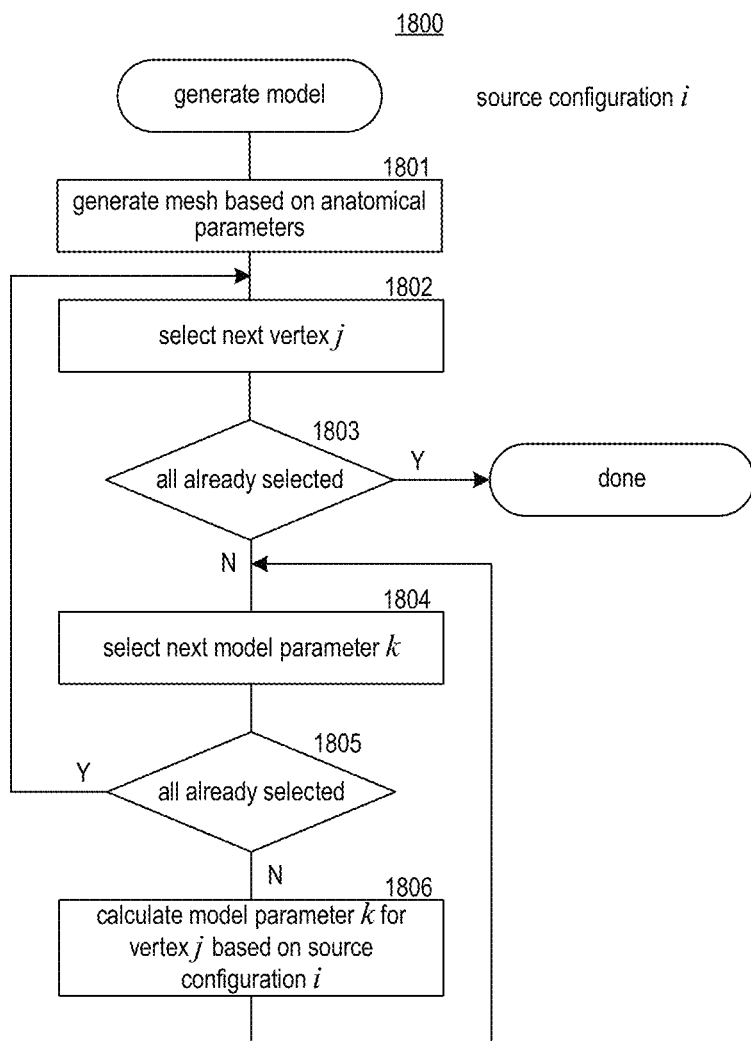
FIG. 18 is a flow diagram that illustrates the processing of a generate model component of the MLG system in some embodiments.

FIG. 18 is a flow diagram that illustrates the processing of a generate model component of the MLG system in some embodiments. The generate model component 1800 is invoked, passing an indication of a source configuration i, and generates a model. The model includes one or more model parameters for each vertex of a mesh representing the simulated anatomy of the source configuration. In block 1801, the component generates the mesh based on the anatomical parameters. The mesh may be represented by a data structure that includes, for each vertex, a reference to its adjacent vertices explicitly or implicitly along with a value for one or more model parameters for use in generating, for example, a voltage for that vertex. In block 1802, the component selects the next vertex j. In decision block 1803, if all the vertices have already been selected, then the component completes, else the component continues at block 1804. In block 1804, the component selects the next model parameter k of the computational model for the selected vertex. In decision block 1805, if all the model parameters have already been selected, then the component loops to block 1802 to select the next vertex, else the component continues at block 1806. In block 1806, the component calculates the selected model parameter k for the selected vertex j based on the source configuration i and then loops to block 1804 to select the next model parameter.

Figure 19:
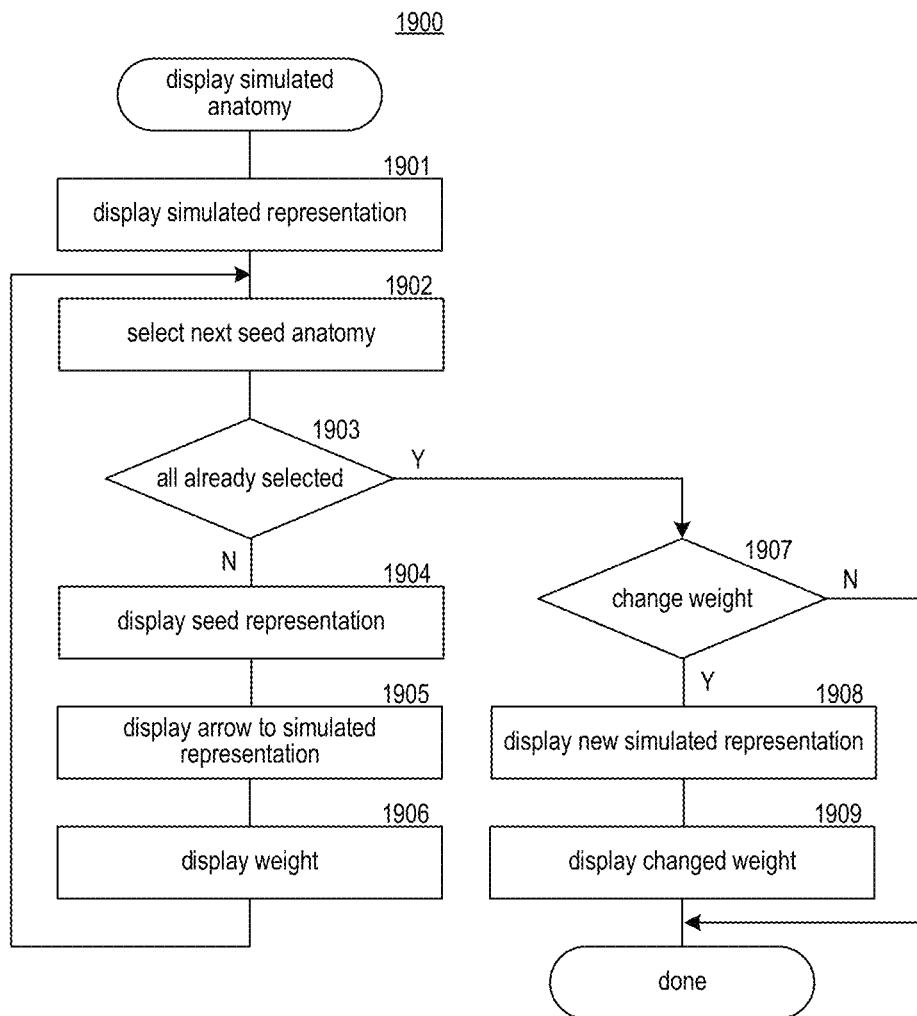
FIG. 19 is a flow diagram that illustrates the processing of a display simulated anatomy component of the MLG system in some embodiments.

FIG. 19 is a flow diagram that illustrates the processing of a display simulated anatomy component of the MLG system in some embodiments. The display simulated anatomy component 1900 is invoked to display a simulated anatomy that has been generated based on seed anatomies. In block 1901, the component displays a simulated representation of a simulated anatomy, such as graphic 1311. In blocks 1902-1906, the component loops, displaying a seed representation of each seed anatomy. In block 1902, the component selects the next seed anatomy that was used to generate the simulated anatomy. In decision block 1903, if all the seed anatomies have already been selected, then the component continues at block 1907, else the component continues at block 1904. In block 1904, the component displays a seed representation of the selected seed anatomy, such as graphics 1301-1306. In block 1905, the component displays an arrow from the seed representation to the simulated representation. In block 1906, the component displays the weight associated with the seed anatomy adjacent to the arrow and then loops to block 1902 to select the next seed anatomy. In decision block 1907, if a user indicates to change the weight, then the component continues at block 1908, else the component completes. In block 1908, the component displays a new simulated representation of a simulated anatomy that is based on the changed weight. The component may invoke the generate simulated anatomy component to generate the simulated anatomy and a component to generate the graphic for the simulated anatomy. In block 1909, the component displays the changed weight near the arrow from the seed representation of the seed anatomy whose weight has been changed and then completes.

Figure 20:
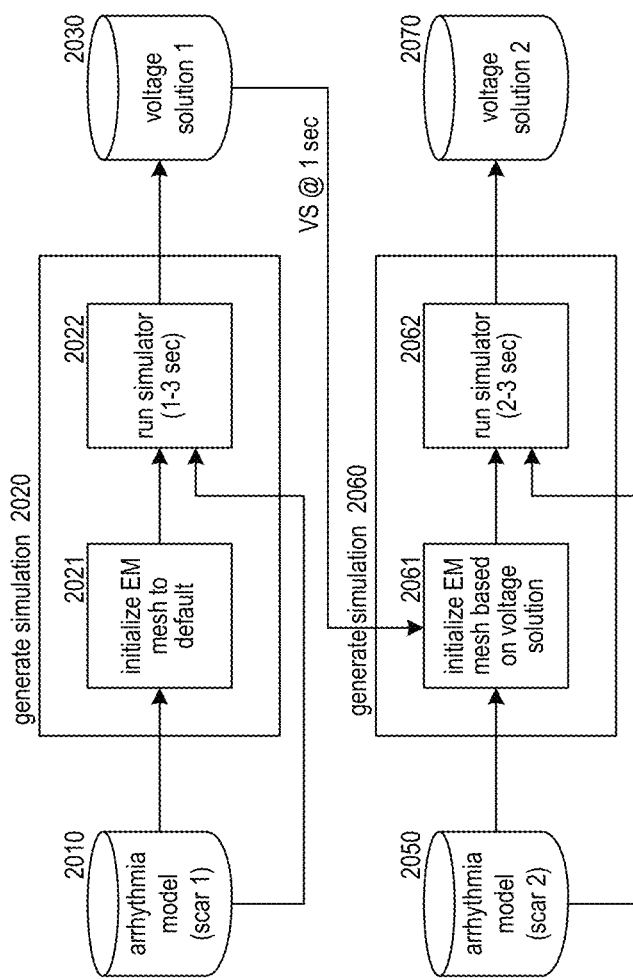
FIG. 20 is a block diagram that illustrates the process of bootstrapping a simulation based on an EM mesh of a prior simulation with similar anatomical parameters.

FIG. 20 is a block diagram that illustrates the process of bootstrapping a simulation based on an EM mesh of a prior simulation with similar anatomical parameters. The simulation may be bootstrapped based on a prior simulation that in turn is based on an arrhythmia model for the same source configuration except for different scar or fibrosis or pro-arrhythmic substrate locations. To generate the initial EM mesh, a generate simulation component 2020 inputs an arrhythmia model 2010 with a first scar or fibrosis or pro-arrhythmic substrate location and outputs a voltage solution 2030. The generate simulation component 2020 includes an initialize mesh to default component 2021 and a run simulation component 2022. The initialize EM mesh component initializes an EM mesh with default values for the voltages of the vertices. The run simulation component 2022 runs a simulation (e.g., for 3 seconds) based on the initialized EM mesh and the arrhythmia model 2010 to generate a voltage solution (e.g., 3,000 EM meshes) and outputs the voltage solution 2030. To bootstrap a simulation, a generate simulation component 2060 inputs an arrhythmia model 2050 with a second scar or fibrosis or pro-arrhythmic substrate location and outputs a voltage solution 2070. The generate simulation component 2060 includes an initialize EM mesh based on voltage solution component 2061 and a run simulation component 2062. The initialize EM mesh based on voltage solution component 2061 inputs the voltage solution 2030 and initializes the EM mesh to, for example, the EM mesh corresponding to the one-second point of the voltage solution 2030. The run simulation component 2062 runs a simulation based on the initialized EM mesh. For example, if the simulations are three seconds and the initialized EM mesh is based on an EM mesh at the one-second point, then the run simulation component 2062 runs a simulation for two additional seconds. The run simulation component 2062 stores the voltage solution in a voltage solution store 2070.

Figure 21:
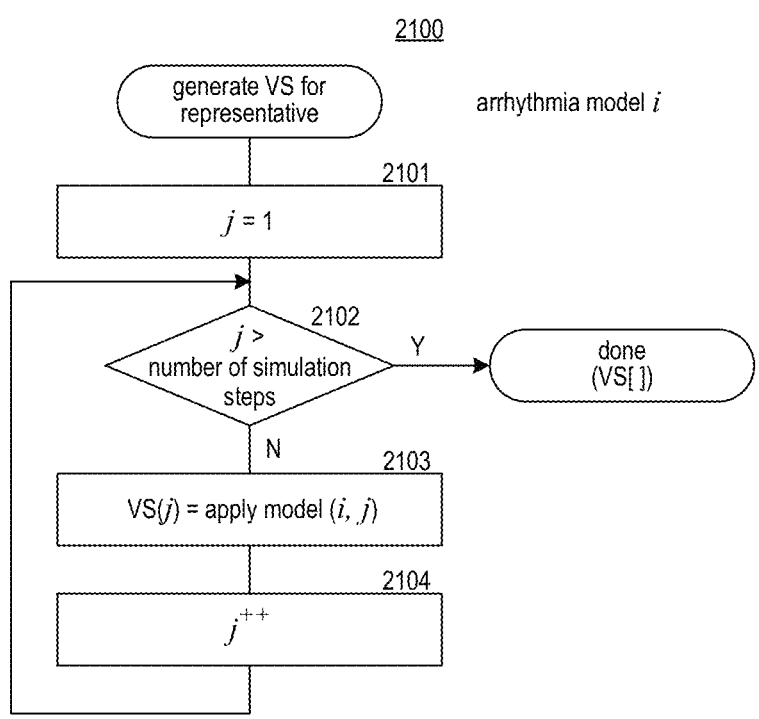
FIG. 21 is a flow diagram that illustrates the processing of a component to generate a voltage solution for a representative arrhythmia model of a group of the MLG system in some embodiments.

FIG. 21 is a flow diagram that illustrates the processing of a component to generate a voltage solution for a representative arrhythmia model of a group of the MLG system in some embodiments. The generate voltage solution for representative component 2100 generates a voltage solution for an arrhythmia model i. In block 2101, the component initializes an index j to track the number of simulation steps. In decision block 2102, if the index j is greater than the number of simulation steps, then the component completes, indicating the voltage solution, else the component continues at block 2103. In block 2103, the component applies the computational model based on the arrhythmia model and the selected simulation step to generate a voltage solution for the selected simulation step. In block 2104, the component increments to the next simulation step and loops to block 2102.

Figure 22:
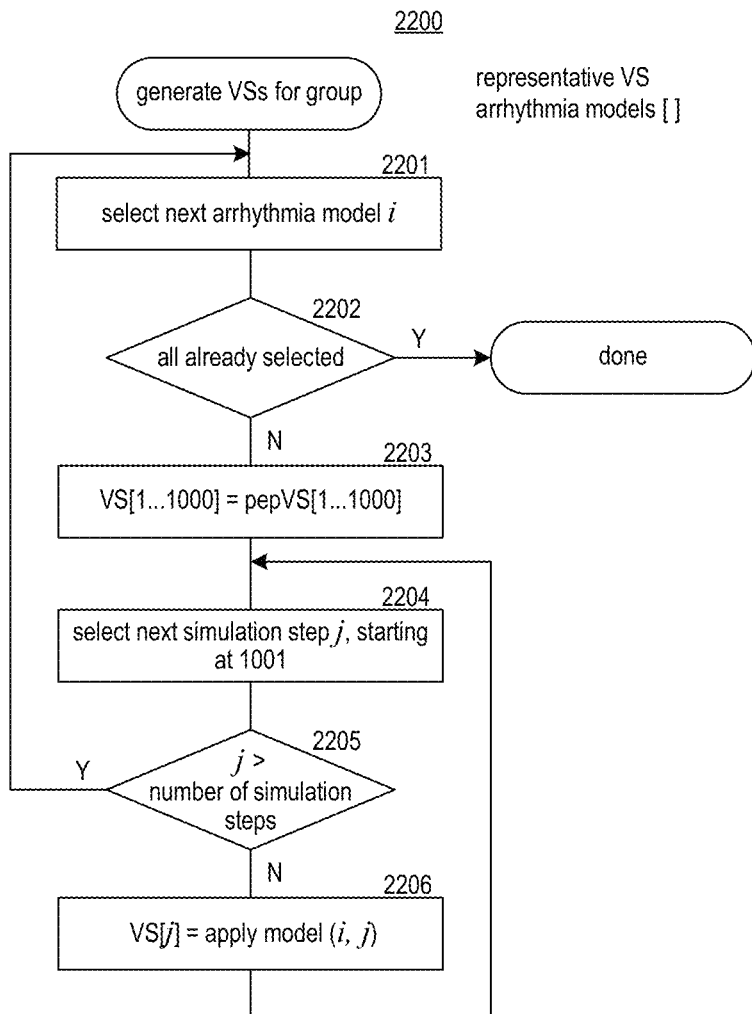
FIG. 22 is a flow diagram that illustrates the processing of a generate voltage solution component for a group of arrhythmia models based on a representative voltage solution of the MLG system in some embodiments.

FIG. 22 is a flow diagram that illustrates the processing of a generate voltage solution component for a group of arrhythmia models based on a representative voltage solution of the MLG system in some embodiments. The generate voltage solution for group component 2200 is passed an indication of a representative voltage solution and a set of arrhythmia models. In block 2201, the component selects the next arrhythmia model i. In decision block 2202, if all the arrhythmia models have already been selected, then the component completes, else the component continues at block 2203. In block 2203, the component initializes the voltage solution for the selected arrhythmia model to the representative voltage solution for the first 1000 simulation steps. In blocks 2204-2206, the component loops, running the simulation starting at simulation step 1001 and continuing to the end of the simulation. In block 2204, the component selects the next simulation step j, starting at simulation step 1001. In decision block 2205, if the current simulation step is greater than the number of simulation steps, then the component loops to block 2201 to select the next arrhythmia model, else the component continues at block 2206. In block 2206, the component applies the arrhythmia model based on the simulation step to generate a voltage solution for the simulation step and then loops to block 2204 to select the next simulation step.

Figure 23:
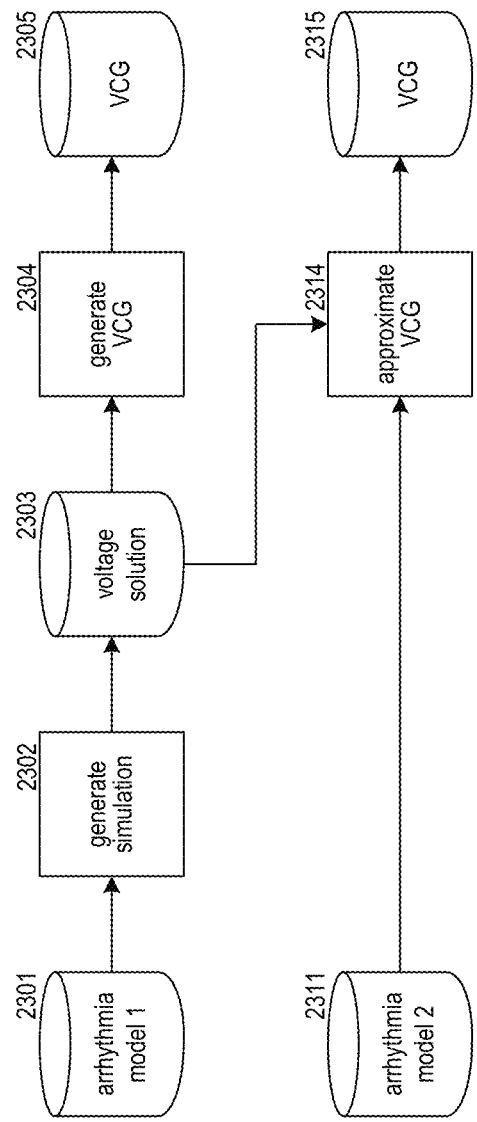
FIG. 23 is a block diagram that illustrates the process of approximating a cardiogram based on a voltage solution for an arrhythmia model with different anatomical parameters.

FIG. 23 is a block diagram that illustrates the process of approximating a vectorcardiogram based on a voltage solution for an arrhythmia model with different anatomical parameters. To generate the voltage solution for an arrhythmia model 2301 based on a first set of anatomical parameters, a generate simulation component 2302 inputs the arrhythmia model and outputs a voltage solution 2303. A generate VCG component 2304 then generates a VCG from the voltage solution and stores it in a VCG store 2305. To approximate a VCG for an arrhythmia model based on a similar source configuration but with different anatomical parameters, an approximate VCG component 2314 inputs an arrhythmia model 2311, generates an approximate VCG, and outputs the VCG 2315.

Figure 24:
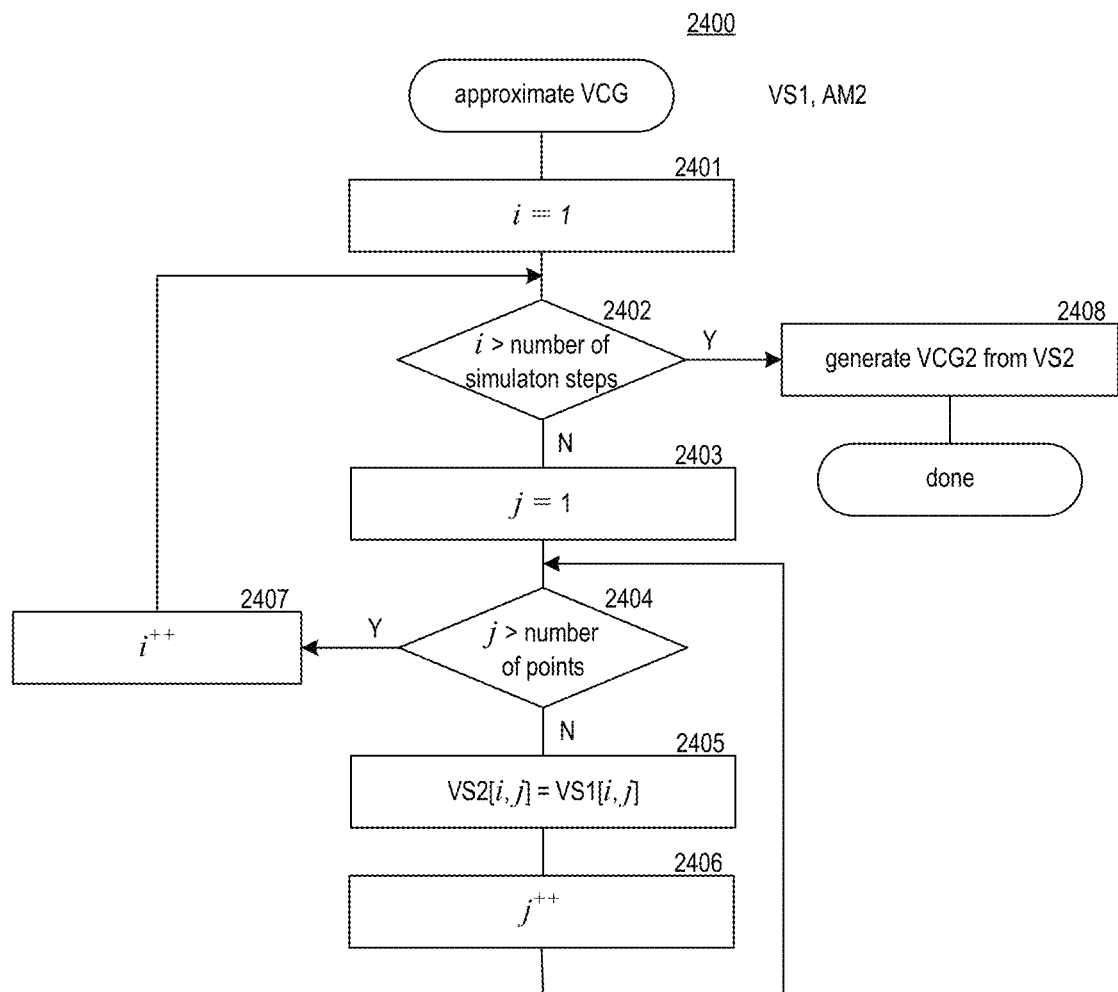
FIG. 24 is a flow diagram that illustrates the processing of an approximate VCG component of the MLG system in some embodiments.

FIG. 24 is a flow diagram that illustrates the processing of an approximate VCG component of the MLG system in some embodiments. The approximate VCG component 2400 inputs a voltage solution ("VS1") generated based on a first arrhythmia model with first anatomical parameters and approximates a VCG for a second arrhythmia model with second anatomical parameters. In block 2401, the component sets an index i for indexing through the simulation steps. In decision block 2402, if index i is greater than the number of simulations steps, then the component continues at block 2408, else the component continues at block 2403. In block 2403, the component sets an index j for indexing through the points (e.g., vertices or Gaussian points) of the mesh of an arrhythmia model. In decision block 2404, if index j is greater than the number of points, then the component continues at block 2407, else the component continues at block 2405. In block 2405, the component sets the value for the voltage solution ("VS2") for the second arrhythmia model at the index simulation step and point to the corresponding value for the voltage solution of the first arrhythmia model. In block 2405, the component increments index j and loops to block 2404. In block 2407, the component increments index i and loops to block 2402. In block 2408, the component generates the VCG for the second arrhythmia model based on the generated voltage solution VS2 and then completes.

Figure 25:
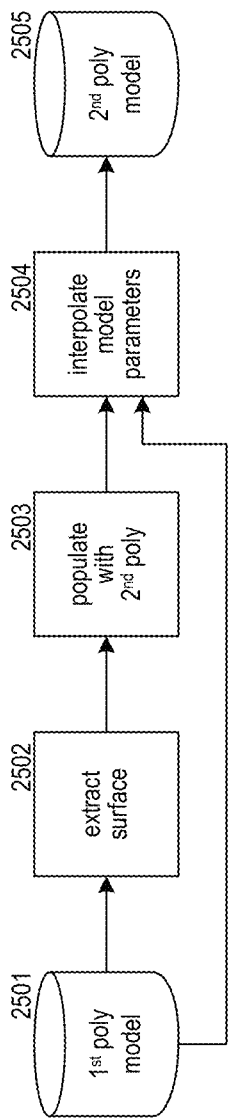
FIG. 25 is a block diagram that illustrates the process of converting an arrhythmia model based on a first polyhedron to an arrhythmia model based on a second polyhedron in some embodiments.

FIG. 25 is a block diagram that illustrates the process of converting an arrhythmia model based on a first polyhedron to an arrhythmia model based on a second polyhedron in some embodiments. A first polyhedron arrhythmia model of a first polyhedron arrhythmia model 2501 is input to an extract surface component 2502. The extract surface component extracts the surface of the mesh of the arrhythmia model. A populate with second polyhedrons component 2303 inputs the surface and populates the volume within the surface with the second type of polyhedrons. An interpolate model parameters component 2504 inputs the second polyhedron mesh and the first polyhedral model and generates model parameters of the second polyhedral model and outputs the second polyhedral model 2505.

Figure 26:
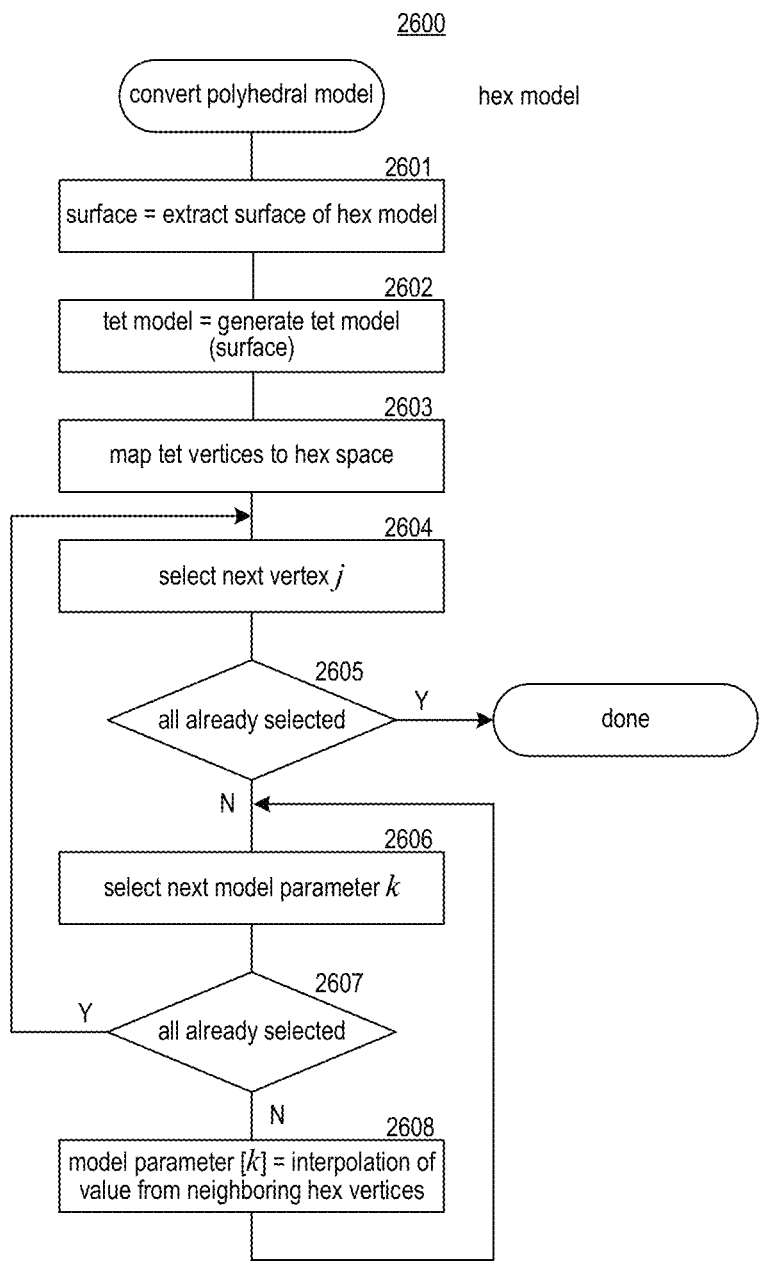
FIG. 26 is a flow diagram that illustrates the processing of a convert polyhedral model component of the MLG system in some embodiments.

FIG. 26 is a flow diagram that illustrates the processing of a convert polyhedral model component of the MLG system in some embodiments. A convert polyhedral model component 2600 is invoked to convert a hexahedral model to a tetrahedral model. In block 2601, the component extracts the surface from the hexahedral model. In block 2602, the component generates a tetrahedral mesh based on the surface of the hexahedral model. In block 2603, the component maps the vertices of the tetrahedral mesh to the space of the hexahedral mesh of the hexahedral model, for example, setting the locations of the vertices relative to the same origin. In block 2604, the component selects the next vertex j of the tetrahedral mesh. In decision block 2605, if all such vertices have already been selected, then the component completes, else the component continues at 2606. In block 2606, the component selects the next model parameter k. In decision block 2607, if all the model parameters have already been selected for the selected vertex, then the component loops to block 2604 to select the next vertex, else the component continues to block 2608. In block 2608, the component sets the selected model parameter based on interpolation of the values of the selected model parameter of neighboring vertices in the hexahedral model. The component then loops to block 2606 to select the next model parameter.

Patient Matching System

Methods and systems for identifying attributes or classification of an EM source within a body based on patient matching that is matching a patient source configuration to model source configurations of the EM source are provided. In some embodiments, a patent matching ("PM") system uses the matching model source configurations to speed up the process of identifying the attributes for the patient or to provide a more accurate classification for the patient using a classifier. To identify an attribute (e.g., arrhythmia source location) for a patient, the PM system generates a mapping of each model source configuration used to generate simulated (or modeled) EM output to the derived EM data that is derived from the simulated EM output generated based on that model source configuration. Each derived (or modeled) EM data is also mapped to an attribute associated with the EM source having the model source configuration. For example, when the EM source is a heart, the model source configurations include configuration parameters such as anatomical parameters and electrophysiology parameters. The configuration parameters may include the source location of an arrhythmia, a rotor type, type of disorder or condition, and so on. One of the configuration parameters, such as arrhythmia source location, may be designated as an attribute parameter, which represents the attribute to be identified for a patient. The PM system generates the mappings of model source configurations to modeled VCGs and generates the mappings of modeled VCGs to their corresponding source location of the arrhythmia. The mappings of modeled VCGs to source locations may be generated in a manner similar to how the training data is generated by the MLMO system with the attribute corresponding to the label.

In some embodiments, the PM system uses the mappings to identify the attribute for a patient based on a combination of the patient source configuration of the patient and a patient VCG of the patient. The attribute can be identified by comparing the patient VCG to each modeled VCG to identify the most similar modeled VCG and by identifying the attribute of that most similar modeled VCG as the patient attribute of the patient. It can, however, be computationally very expensive to compare the patient VCG to each modeled VCG because the number of modeled VCGs may be in the millions. The PM system may employ various techniques to reduce the computational expense. With one technique, the PM system uses the patient source configuration to reduce the number of modeled VCGs to which the patient VCG needs to be compared. The PM system may allow a user to provide the patient source configuration for a patient. It would be preferable if a value for each configuration parameter of the patient source configuration could be provided. In practice, however, it may be that the values of only certain configuration parameters are known for a patient. In such cases, the PM system performs the comparison based on the known values of the configuration parameters, rather than all the configuration parameters. The anatomical parameters for a patient may be calculated based on imaging scans. The action potentials may be calculated based on output of a basket catheter inserted into the patient's heart or the patient's history of anti-arrhythmic drug or gene therapy, and the conductivity may be calculated based on analysis of the patient's ECG. The configuration parameters may also include electrophysiology parameters to indicate whether the action potential and/or conductivity represents a diseased state. In such a case, if the action potential or conductivity of a patient is not available, the configuration parameters indicate whether the action potential or conductivity represent a disease state. The PM system may use various techniques to assess the similarity between a patient source configuration and a model source configuration such as one based on least squares, cosine similarity, and so on. The PM system may generate a similarity score for each model source configuration and identify as matching model source configurations those with a similar score that is above a matching threshold.

In some embodiments, after the matching model source configurations are identified, the PM system compares the patient VCG to the modeled VCGs to which the matching model source configurations are mapped. The PM system may generate a similar score for each modeled VCG (e.g., using a Pearson correlation technique) and identify as matching modeled VCGs those with a similarity score above a threshold similarity. The PM system then identifies the attribute(s) for the patient based on the attributes of the matching modeled VCGs. For example, if the attribute is source location of an arrhythmia, the PM system may generate an average of the source locations weighted based on the similar scores of the matching model VCGs. In this way, the PM system avoids the computational expense of comparing a patient VCG to every modeled VCG.

In some embodiments, the PM system may employ other techniques for reducing the computational expense of comparing the patient VCG to every modeled VCG. For example, the PM system may identify features of VCGs such as area, maximum dimensions, and so on. The PM system then may generate an index that maps values of the features to the modeled VCGs having those values. To identify modeled VCGs that match a patient VCG, the PM system identifies the features of the patient VCG and uses the index to identify matching modeled VCGs. For example, the PM system may identify for, each feature, a set of the modeled VCGs that match that feature of the patient VCG. The PM system can then identify the modeled VCGs that are common to each set (e.g., intersection of the sets) or most common to the sets as the matching modeled VCGs. The PM system can then compare those matching modeled VCGs to the patient VCG as described above to identify the attribute.

In some embodiments, the PM system may employ patient matching to improve the classification of VCGs based on a trained classifier. The PM system may generate clusters of similar model source configurations using various clustering techniques. The clustering techniques may include a centroid-based clustering technique (e.g., k-means clustering), a supervised or unsupervised learning clustering technique (e.g., using a neural network), and so on. With a centroid-based clustering technique, the PM system generates clusters by successively adding each model source configuration to the current cluster of model source configurations to which it is most similar. The PM system may combine and split clusters dynamically, for example, based on the number of model source configuration in each cluster, the similarity of the model source configurations of one cluster to another, and so on. After the clusters are identified, the PM system may employ components of the MLMO system to generate a classifier for each cluster. The PM system trains the classifier for a cluster based on the modeled VCGs for the model source configurations of that cluster as the training data for the classifier.

In some embodiments, to generate a classification for a patient, the PM system identifies the cluster with model source configurations that best matches the patent source configuration. For example, the PM system may generate a similarity score for each cluster based on similarity between a representative model source configuration (e.g., with average values of a cluster) of that cluster and the patient source configuration. The PM system then selects the classifier for the cluster with the highest similarity score and applies that classifier to the patient VCG to generate the classification for the patient. Because each classifier is trained based on a cluster of similar model source configurations, each classifier is adapted to generate classifications based only on the differences, which may be subtle, in those similar model source configurations. In contrast, a classifier trained based on all model source configurations may not be able to factor in subtle differences between similar model source configurations. As such, a classifier trained based on a cluster of similar model source configurations may provide a more accurate classification than a classifier trained based on all model source configurations.

In some embodiments, the PM system may generate the modeled EM output for the model source configurations assuming a standard orientation of a heart. If a patient, however, has a heart with a somewhat different orientation, then the matching modeled VCGs may not have attributes or classifications that would apply to the patient because of the differences in the orientations. In such a case, the PM system may perform a VCG rotation prior to comparing the patient VCG to the modeled VCGs. The PM system may rotate either each modeled VCG or the patient VCG. The PM system may generate a rotation matrix based on the difference in orientations. The PM system then performs a matrix multiplication between each point (e.g., x, y, and z values) of a VCG and the rotation matrix (e.g., a 3-by-3 matrix) to generate a rotated point for the rotated VCG. The MLMO system may also rotate VCGs based on difference in orientations.

Figure 27:
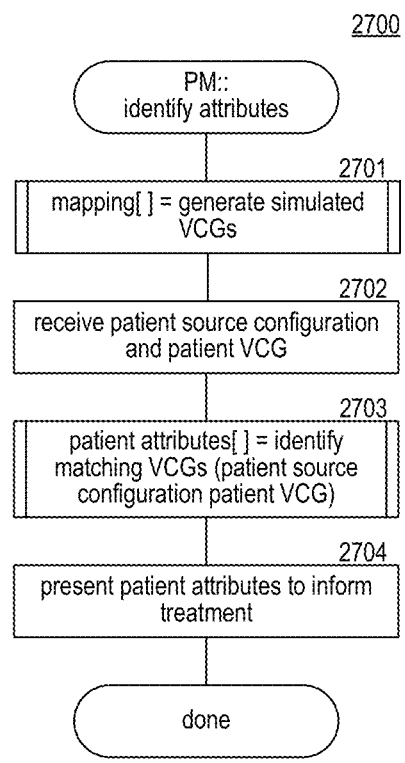
FIG. 27 is a flow diagram that illustrates the processing of an identify attributes component of the PM system in some embodiments.

FIGS. 27-30 are flow diagrams that illustrates the processing of components of the PM system in some embodiments. FIG. 27 is a flow diagram that illustrates the processing of an identify attributes component of the PM system in some embodiments. The identify attributes component 2700 identifies patient attributes of a patient based on a patient source configuration and a patient cardiogram (e.g., the VCG). In block 2701, the component invokes the generate simulated VCGs component of the MLMO system to generate the modeled VCGs and then maps them to the model source configurations from which they were generated. In block 2702, the component retrieves the patient source configuration and the patient VCG. In block 2703, the component invokes the identify matching VCGs component passing an indication of the patient source configuration and the patient VCG to identify patient attributes based on the matching VCGs. In block 2704, the component presents the patient attributes to inform treatment on the patient and then completes.

Figure 28:
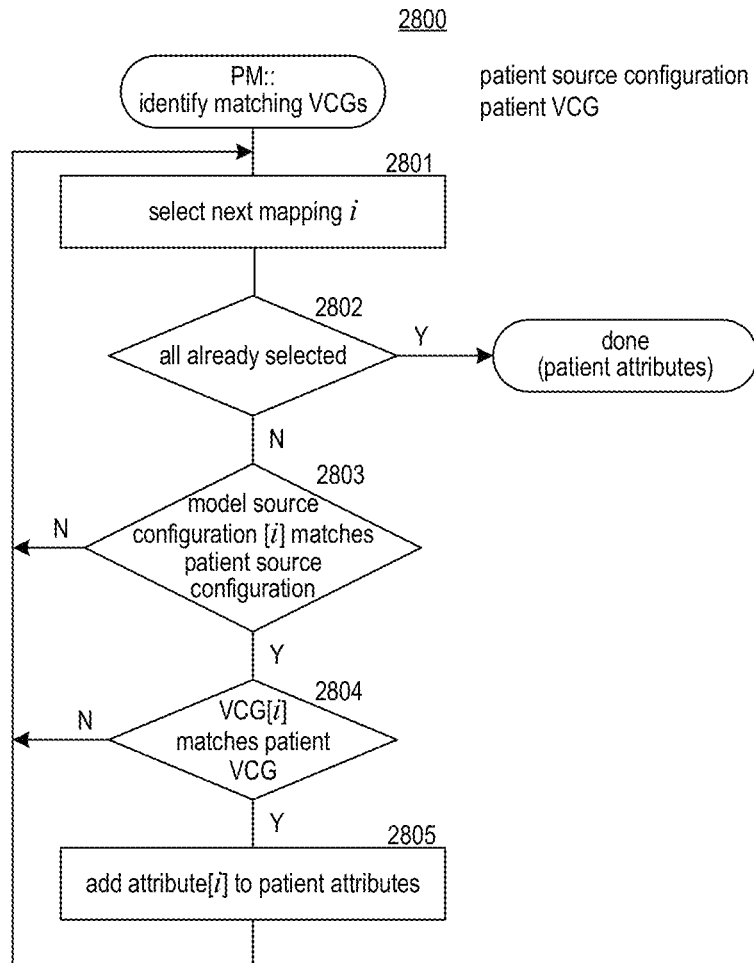
FIG. 28 is a flow diagram that illustrates the processing of an identify matching VCGs component of the PM system in some embodiments.

FIG. 28 is a flow diagram that illustrates the processing of an identify matching VCGs component of the PM system in some embodiments. The identify matching VCGs component 2700 is passed a patient source configuration and a patient VCG and identifies the patient attributes. In block 2801, the component selects the next mapping of a model source configuration to a modeled VCG. In decision block 2802, if all the mappings have already been selected, then the component completes indicating the patient attributes, else the component continues at block 2803. In decision block 2003, if the selected model source configuration matches the patient source configuration, then the component continues at block 2804, else the component loops to block 2801 to select the next mapping. In decision block 2804, if the modeled VCG for the selected mapping matches the patient VCG, then the component continues at block 2805, else the component loops to block 2801 to select the next mapping. In block 2805, the component adds the attribute for the selected modeled VCG to the patient attributes and then loops to block 2801 to select the next mapping. In some embodiments, the PM system may include components to identify other types of matching measurements such as an EEG and measurements corresponding to those collected by a body surface vest, a basket catheter, a cap worn by a patient, and so on.

Figure 29:
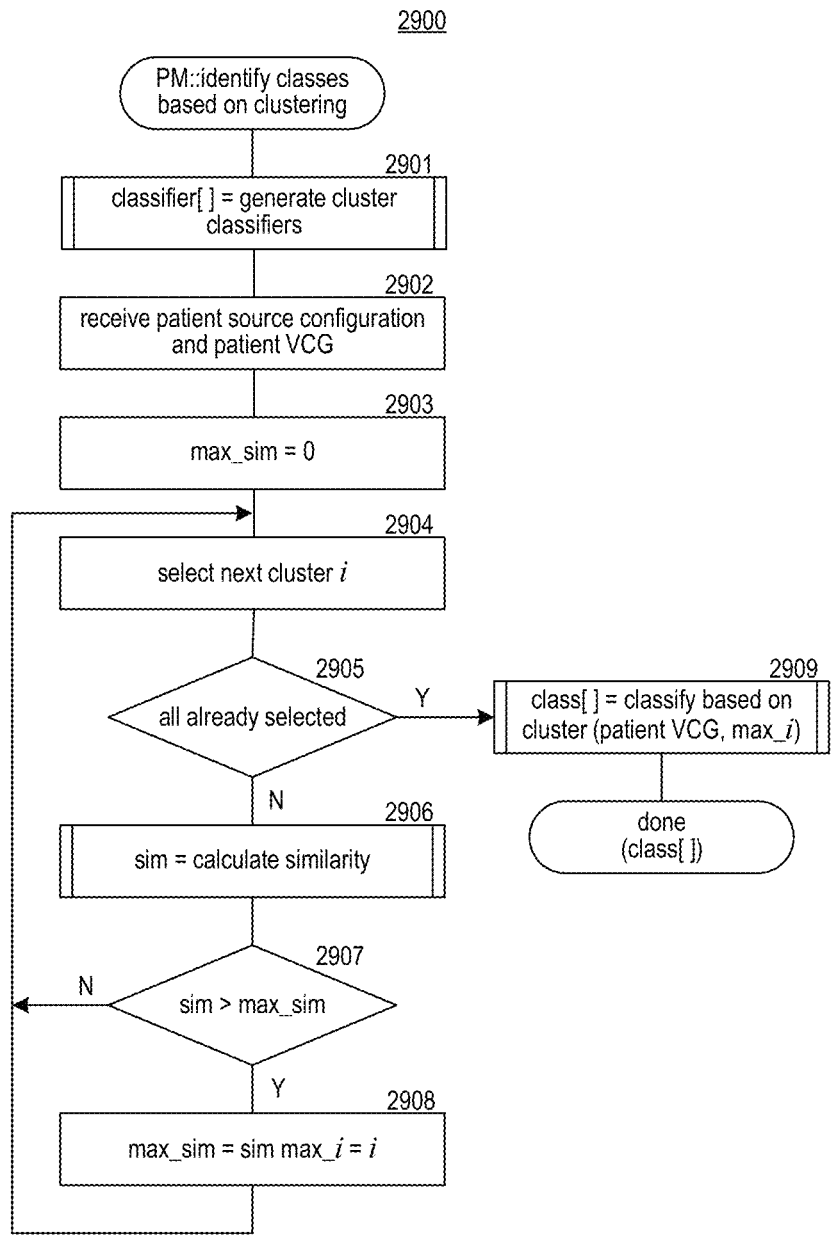
FIG. 29 is a flow diagram that illustrates the processing of an identify classes based on clustering component of the PM system in some embodiments.

FIG. 29 is a flow diagram that illustrates the processing of an identify classes based on clustering component of the PM system in some embodiments. The identify classes based on clustering component 2900 identifies the classes for a patient based on classifiers trained using clusters of similar model source configurations. In block 2901, the component invokes a generate cluster classifiers component to generate classifiers for clusters of similar model source configurations. In block 2902, the component receives a patient source configuration and a patient VCG. In blocks 2903-2908, the component loops selecting clusters to identify the cluster with model source configurations that are most similar to the patient source configuration. In block 2903, the component initializes the variable to track the maximum similarity calculated so far. In block 2904, the component selects the next cluster. In decision block 2905, if all the clusters have already been selected, then the component continues at block 2909, else the component continues at block 2906. In block 2906, the component invokes a calculate similarity component to calculate the similarity between the model source configurations of the selected cluster and the patient source configuration. In decision block 2907, if the similarity is greater than the maximum similarity calculated so far, then the component continues at block 2908, else the component loops to block 2904 to select the next cluster. In block 2908, the component sets the maximum similarity to the similarity calculated for the selected cluster and sets a variable to indicate the index of the cluster with the maximum similarity calculated so far. The component then loops to block 2904 to select the next cluster. In block 2909, the component invokes a classify based on cluster component to identify the classes for the patient VCG based on the cluster with the maximum similarity. The classify based on cluster component may correspond to the classify component of the MLMO system that has been adapted to input the classifier to use. The component then completes indicating the classes.

Figure 30:
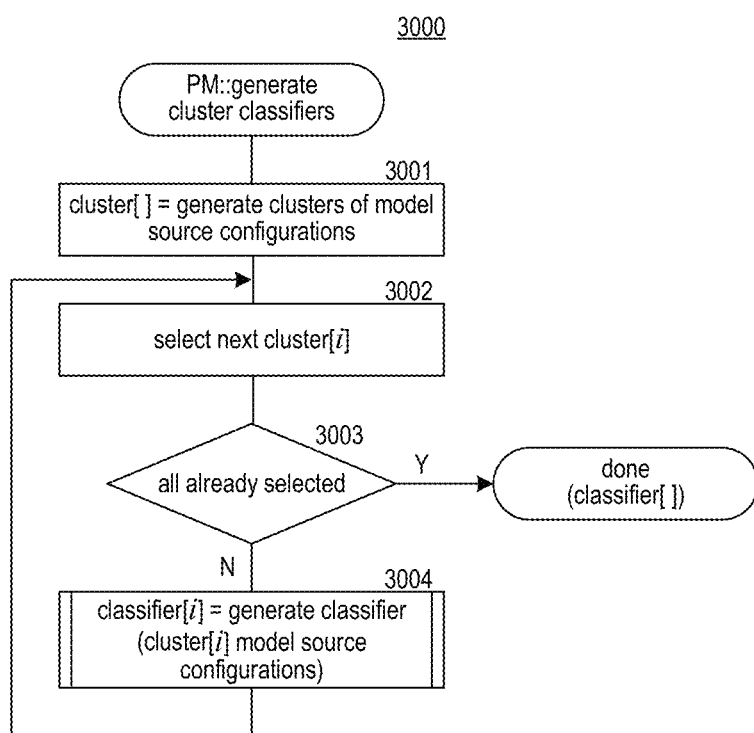
FIG. 30 is a flow diagram that illustrates the processing of a generate cluster classifiers component of the PM system in some embodiments.

FIG. 30 is a flow diagram that illustrates the processing of a generate cluster classifiers component of the PM system in some embodiments. The generate cluster classifiers component 3000 is invoked to cluster the model source configurations and generate a classifier based on each cluster. In block 2001, the component generates the clusters of the model source configurations. In block 3002, the component selects the next cluster. In decision block 3003, if all the clusters have already been selected, then the component completes indicating the classifiers, else the component continues at block 3004. In block 3004, the component invokes a generate classifier component of the MLMO system passing an indication of the model source configurations of the selected cluster to generate a classifier for that cluster. The component then loops to block 3002 to select the next cluster.

Machine Learning Based on Clinical Data

Methods and systems are provided to adapt the MLMO system to generate classifiers based on actual patient data. In some embodiments, a machine learning based on clinical data ("MLCD") system is provided that generates (1) a patient classifier based on patient training data associated with actual patients using transference of model classifier weights and (2) generates a patient-specific model classifier based on model training data that is selected based on similarity to a patient. The patient classifier is generated by a patient classifier system of the MLCD system, and patient-specific model classifier is generated by a patient-specific model classifier system. The term "patient classifier" refers to a classifier that is generated based on patient training data generated based on data of patients, and the term "model classifier" refers to a classifier that is generated based on model training data generated based on a computational model of an EM source.

Patient Classifier System

In some embodiments, the patient classifier ("PC") system generates a patient classifier for classifying derived EM data derived from EM output of an EM source within a body. For example, the patent classifier classifies VCGs derived from ECGs. The PC system accesses a model classifier such as one generated using the MLMO system. The model classifier is generated using model training data generated using a computational model of an EM source. The model classifier includes model classifier weights that are learned when the model classifier is trained such as the weights of the activation functions of a CNN. The PC system also accesses patient training data that includes, for each of a patient, patient derived EM data (e.g., VCGs) and a patient classification for that patient such as rotor location and prior ablation procedure outcome. An example prior ablation procedure outcome may be that a patient was arrhythmia free for a certain time period after being ablated at a certain location with a certain burn pattern. To train the patient classifier, the PC system initializes patient classifier weights of the patient classifier based on the model classifier weights of the model classifier and then trains the patient classifier with the patient training data and with the initialized patient classifier weights. Normally, the weights of a classifier are initialized to default values such as all to a certain value (e.g., 0.0, 0.5, or 1.0) or to random values. The learning of the weights for the classifier is thus considered to be from "scratch." The process of initializing the values of the weights based on previously learned weights is referred to as "transference" of knowledge. The knowledge gained by the previous training of a prior classifier is transferred to the training of a new classifier. The goal of transference is to both speed up the training of and increase the accuracy of the new classifier.

In some embodiments, the PC system uses the patient classifier to classify patients. For example, when the EM source is a heart, the PC system may receive a cardiogram (e.g., ECG or VCG) of a patient and apply the patient classifier to that cardiogram. Depending on the patients selected for training the patient classifier, the patient classifier may be a more accurate classifier than a model classifier trained on model training data generated using a computational model. Moreover, if the patient is similar to the patients used to train the patient classifier, then the accuracy of the classifier may be even more accurate. The PC system may also identify clusters of similar patients and train a separate patient classifier for each cluster, referred to as a cluster patient classifier. The similarity of the patients may be determined in various ways such as based on comparison of various characteristics such one or more of derived EM data (e.g., cardiograms) collected from the patients, patient source configurations of the patients (e.g., anatomical parameters, electrical dynamic properties), patient demographic information, and so on. The cluster patient classifier for each cluster may be trained based on the VCGs and corresponding labels of the patients in that cluster. When a target patient is to be classified, the PC system identifies the cluster of patients to which the target patient is most similar. The PC system then applies the cluster patient classifier of the identified cluster to VCG of the target patient.

Patient-Specific Model Classifier System

In some embodiments, a patient-specific model classifier ("PSMC") system generates a patient-specific model classifier for classifying derived EM data of an EM source within a body. The PSMC system identifies models that are similar to a patient. The PSMC system identifies similar models based on a patient-model similarity. The patient-model similarity may be based on similarity between model source configuration of a model and patient source configuration of the patient and/or similarity between modeled derived EM data (e.g., VCGs) of a model and corresponding patient derived EM data of the patient. For example, the PSMC system may base the similarity on anatomical parameters (e.g., dimensions of a right ventricle), certain electrophysiology parameters, and so on. The PSMC system then may use the MLMO system to generate a patient-specific model classifier using the model source configurations of the similar models. The PSMC system may generate the patent-specific model classifier by first applying a computational model of the EM source to generate modeled EM output of the EM source based on the model source configurations of the similar models. The PSMC system then generates model training data that includes modeled derived EM data (e.g., VCGs) from the generated modeled EM output and labels for the models. Alternatively, if the model training data has already been generated for the similar models, then the PSMC system need not regenerate the model training data. The PSMC system then trains the patient-specific model classifier based on the model training data.

In some embodiments, after a patient-specific model classifier is generated, the PSMC system applies the patient-specific model classifier to derived EM data (e.g., VCG) of the patient to generate a classification for the patient. Because the patient-specific model classifier is trained using model training data that is selected based on the patient, the patient-specific model classifier provides classification that is more accurate than a classification that would be provided by a model classifier trained based on a collection of model training data that is not specific to the patient.

In some embodiments, the PSMC system may generate a cluster-specific model classifier for a cluster of target patients. To generate a cluster-specific model classifier, the PSMC system identifies models that are overall similar to the target patients of the cluster and then trains a cluster-specific model classifier based on the similar models. The PSMC system can then apply the cluster-specific model classifier to generate a classification for the target patients of the cluster. The PSMC system may also generate clusters of target patients and generate a cluster-specific model classifier for each cluster. The PSMC system can then generate a classification for each target patient using the cluster-specific model classifier for the cluster to which that target patient is a member. The PSMC system may even use a cluster-specific model classifier to generate a classification for a new target patient. The PSMC system identifies the cluster to which a new target patient is most similar and applies the cluster-specific model classifier for that identified cluster to the patient derived EM data for the new target patient to generate the classification for the new target patient.

Figure 31:
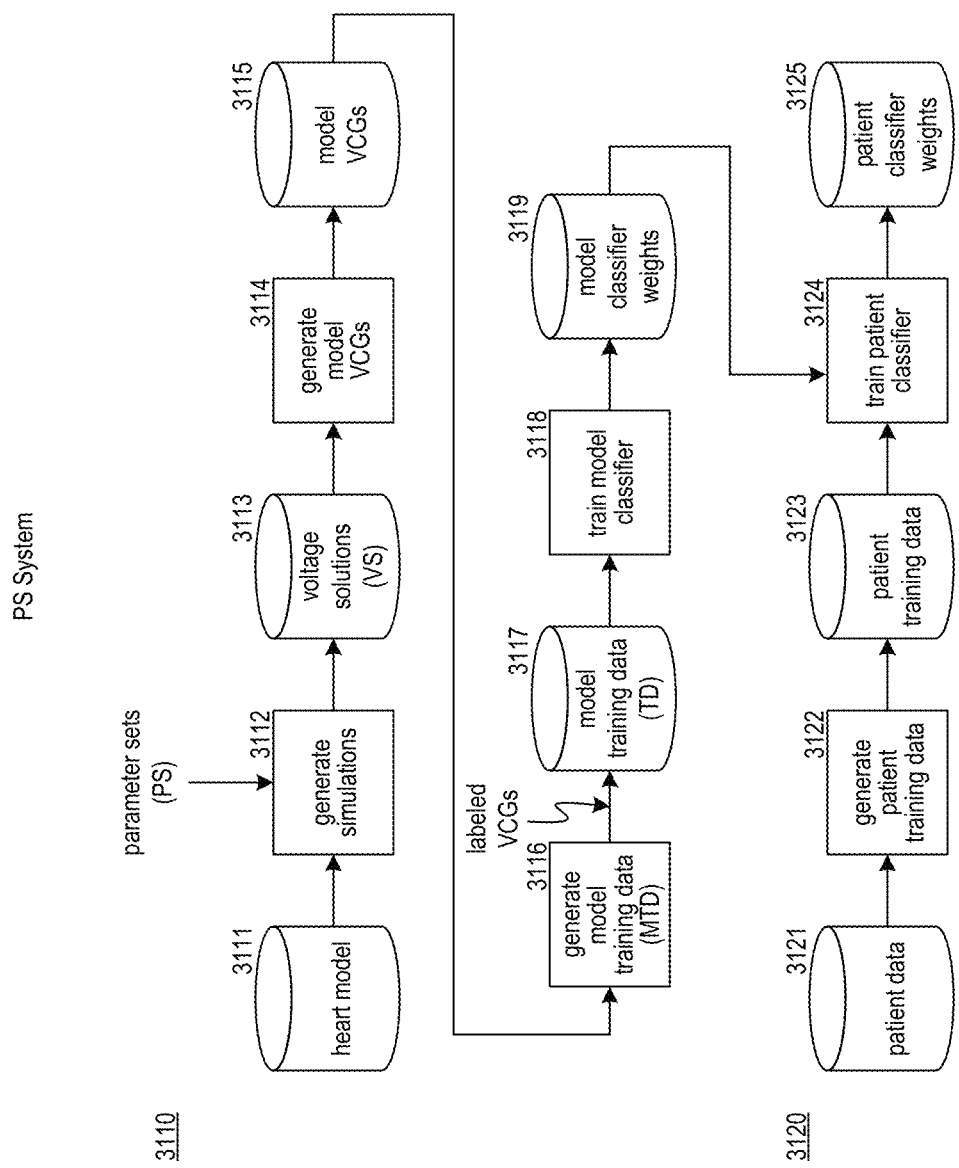
FIG. 31 is a block diagram that illustrates the overall processing of a patient classifier system of a MLCD system in some embodiments.

FIG. 31 is a block diagram that illustrates the overall processing of a patient classifier system of a MLCD system in some embodiments. Classifier components 3110 (i.e., components 3111-19) are similar to classifier components 110 of FIG. 1. The term "model" has been inserted in various components to emphasize that the components are used to generate a classifier based on models represented by simulated source configurations or parameter sets. Components

3120 include a patient data store 3121, a generate patient training data component 3122, a patient training data store 3123, a train patient classifier component 3124, and a patient classifier weights store 3125. The patient data store may include ECGs collected from patients and corresponding labels such as locations of a heart disorder. The generate patient training data component generates patient training data from the patient data, for example, by generating VCGs from the ECGs and labeling the VCGs and storing the training data in the patient training data store. The train patient classifier component inputs the model classifier weights from a model classifier weights store 3119 as transference of knowledge from the model classifier and trains the patient classifier based on the patient training data. The train patient classifier then stores the patient classifier weights in the patient classifier weights store.

Figure 32:
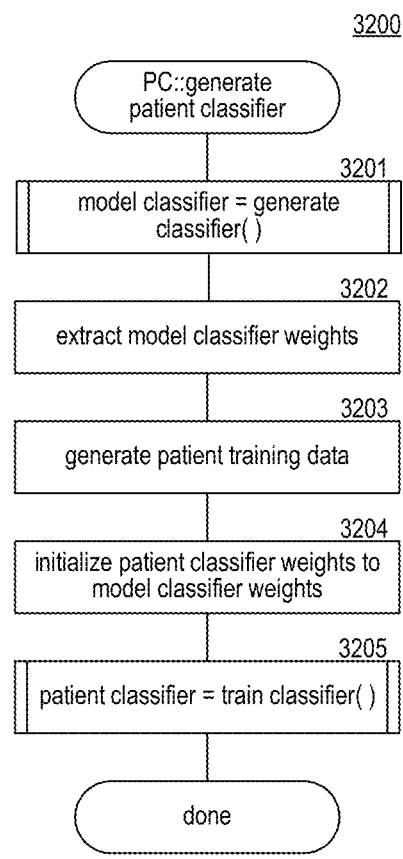
FIG. 32 is a flow diagram that illustrates the processing of a generate patient classifier component of the patient classifier system in some embodiments.

FIG. 32 is a flow diagram that illustrates the processing of a generate patient classifier component of the patient classifier system in some embodiments. The generate patient classifier component 3200 generates a patient classifier for a collection of patients using transference of knowledge from a model classifier. In block 3201, the component invokes a generate classifier component to generate a model classifier based on model training data if the model classifier has not already been generated. The generate classifier component generates model classifier weights for the model classifier. In block 3202, the component extracts the model classifier weights of the model classifier. In block 3203, the component generates the patient training data, for example, by generating VCGs and labeling the VCGs. In block 3204, the component initializes the patient classifier weights of the patient classifier to the model classifier weights. In block 3205, the component invokes a train classifier component to train a patient classifier based on the patient training data and the initialized patient classifier weights. The component then completes.

Figure 33:
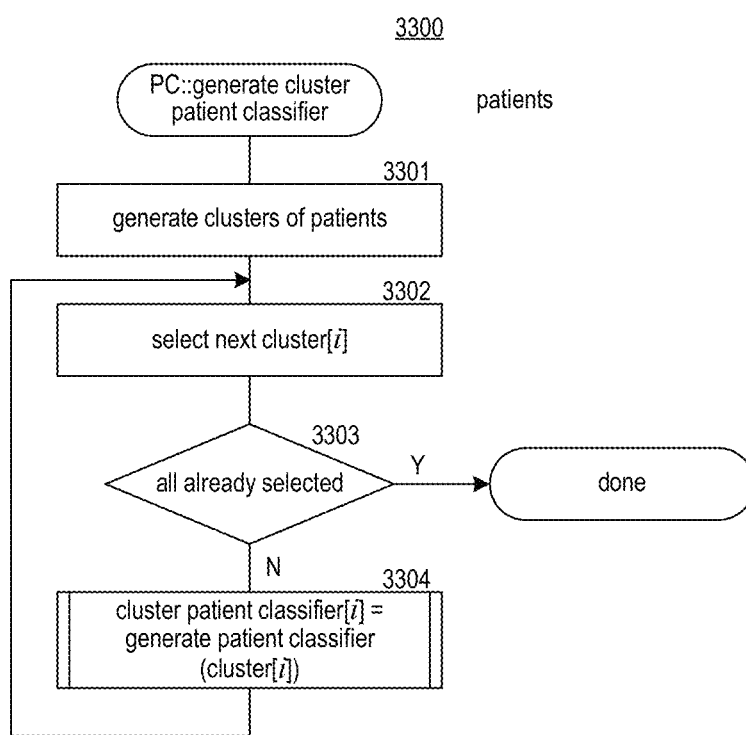
FIG. 33 is a flow diagram that illustrates the processing of a generate cluster patient classifier of the patient classifier system in some embodiments.

FIG. 33 is a flow diagram that illustrates the processing of a generate cluster patient classifier of the patient classifier system in some embodiments. The generate cluster patient classifier 3300 generates a cluster patient classifier for clusters of patients. In block 3301, the component generates clusters of patients, for example, based on similarity of their clinical features, source configurations, or VCGs. In block 3302, the component selects the next cluster. In decision block 3303, if all the clusters have already been selected, then the component completes, else the component continues at block 3304. In block 3304, the component invokes a generate patient classifier component passing an indication of the selected cluster to generate a cluster patient classifier for the patients in the selected cluster and then loops to block 3302 to select the next cluster. When the generate patient classifier component is invoked, it does not need to generate a model classifier for each invocation because it can reuse the same model classifier weights for each invocation.

Figure 34:
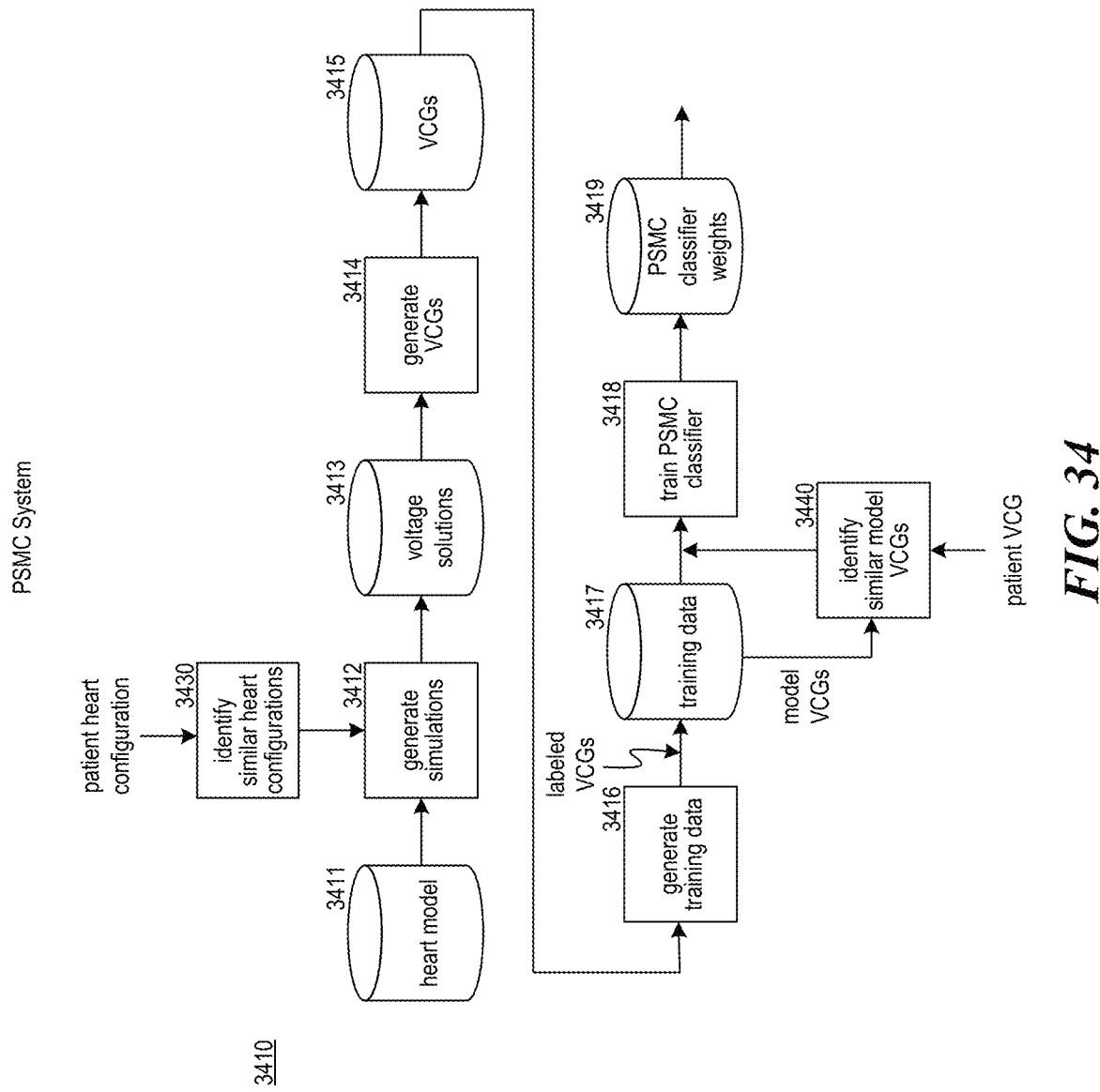
FIG. 34 is a block diagram that illustrates components of a patient-specific model classifier system of a MLCD system in some embodiments.

FIG. 34 is a block diagram that illustrates components of a patient-specific model classifier system of a MLCD system in some embodiments. The PSMC system includes components 3410 (components 3411-19) are similar to components 110 of FIG. 1. The PSMC system also includes an identify similar heart configurations component 3430 and an identify similar VCGs component 3440, which represent two different embodiments of the PSMC system. In a first embodiment, the identify similar hearts configuration component inputs a patient heart configuration and model heart configurations and identifies the model heart configurations that are similar to the patient heart configuration. The similar model heart configurations are then input to the generate simulations component to generate the voltage solutions and ultimately train the patient-specific model classifier. In a second embodiment, the identify similar VCGs component inputs a patient VCG and the training data and identifies VCGs of the training data that are similar to the patient VCG. The training data for the similar VCGs is an input to the train PSMC classifier component 3418 to train the patient-specific model classifier. Although not illustrated, the train PSMC classifier may use transference to initialize the PSMC classifier weights. Also, the first and second embodiments may be both used to generate training data based on similar heart configurations and then select similar VCGs for training.

Figure 35:
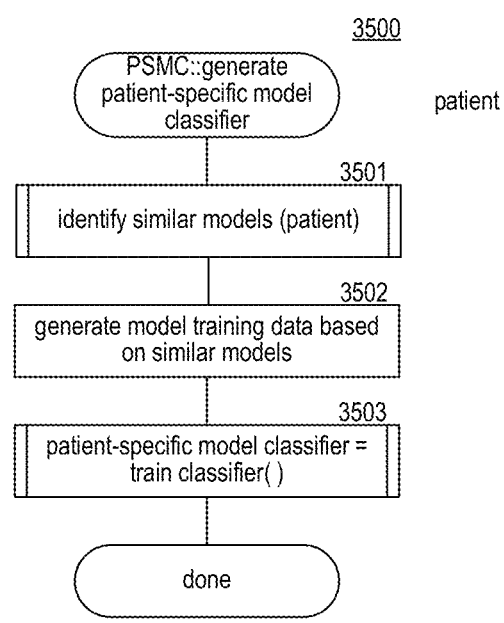
FIG. 35 is a flow diagram that illustrates processing of a generate patient-specific model classifier component of the PSMC system in some embodiments.

FIG. 35 is a flow diagram that illustrates processing of a generate patient-specific model classifier component of the PSMC system in some embodiments. The generate patient-specific model component 3500 generates a patient-specific model classifier for a target patient. In block 3501, the component invokes an identify similar models component passing an indication of the target patient to identify similar models. In block 3502, the component generates model training data based on the identified similar models. The component may employ the MLMO system to generate the training data based on the model heart configurations of the identified similar models or, if already generated, retrieve the training data based on similar VCGs. In block 3503, the component invokes the train classifier component to train the patient-specific model classifier based on the model training data for the similar models and then completes.

Figure 36:
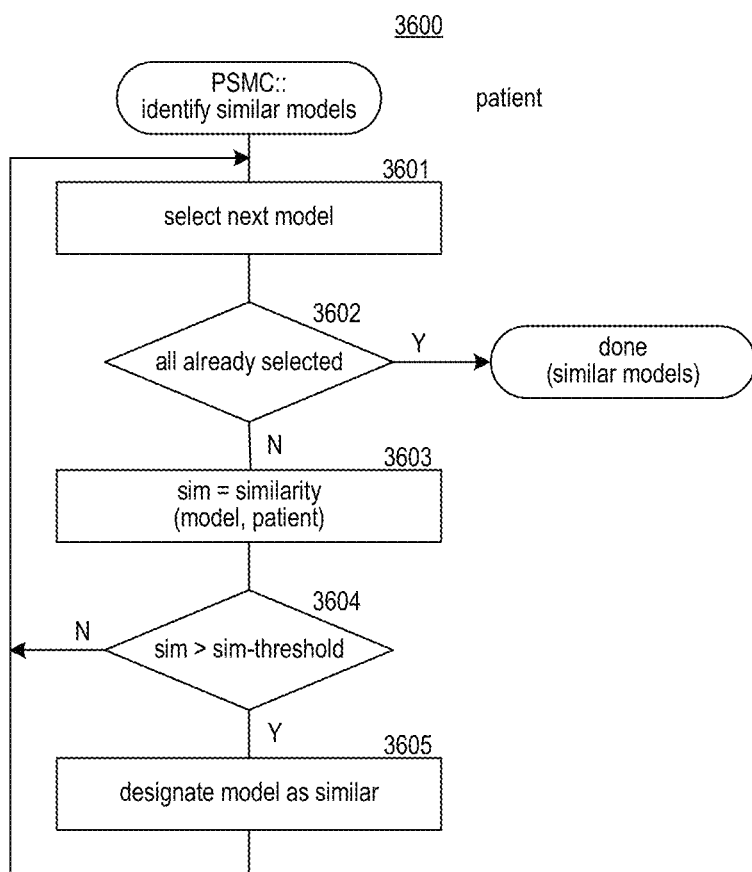
FIG. 36 is a flow diagram that illustrates the processing of an identify similar models component of the PSMC system in some embodiments.

FIG. 36 is a flow diagram that illustrates the processing of an identify similar models component of the PSMC system in some embodiments. The identify similar models component 3600 identifies models that are similar to a patient. In block 3601, the component selects the next model. In decision block 3602, if all the models have already been selected, then the component completes indicating the similar models, else the component continues at block 3603. In block 3603, the component generates a similarity score between the selected model and the patient. The patient-model similarity score may be based on heart configurations, cardiograms, or both. In decision block 3604, if the similarity score is above a similarity threshold, then the component continues at block 3605, else the component loops to block 3601 to select the next model. In block 3605, the component designates the model as similar to the patient and loops to block 3601 to select the next model.

Patient-Specific Model Display

Methods and systems are provided to adapt the MLMO system to support generating and displaying a representation of an EM source of a patient that is based on modeled EM output for a model that is similar to the patient. In some embodiments, a patient-specific model display ("PSMD") system identifies a model for the EM source that is deemed similar to the EM source of a patient. The PSMD system then generates a graphical representation of patient's EM source based on clinical parameters for the patient such as infarction and drug history. For example, if the EM source is a heart, the PSMD system may generate a map representing an anatomical model of the patient's heart. The PSMD system then populates the map with display values that are derived from the modeled EM output for the similar model. For example, the PSMD system may select an EM mesh of that modeled EM output and set each the value of each vertex of the map based on the corresponding voltage of that EM mesh. The PSMD system may also map the modeled EM output from the polyhedral mesh used in the simulation to another polyhedral mesh to produce a more realistic looking display such as a hexahedral mesh to a surface-triangle mesh. The PSMD system may set the values corresponding to high voltages to varying intensities of the color red (or grey scale shading) and the values corresponding to low voltages to varying intensities of the color green. As another example, the PSMD system may select a cycle of the model EM output and set the values based on the differences or delta between voltages of the first EM mesh in the cycle and the last EM mesh in the cycle. The PSMD system may also set the values based on an accumulation, which may be weighted, of the deltas over successive EM meshes in a cycle. The PSMD system then displays (e.g., using a rasterization technique) the map as the representation of activity of the patient's EM source. The PSMD system may also display an outlined image of a heart based on the anatomical parameters of the patient. The outlined image may illustrate boundaries of the chambers of the heart.

In some embodiments, the PSMD system may identify a model that is similar to a patient by comparing model source configurations and modeled derived EM data to the patient source configuration and the patent derived EM data. The comparison may be based on the processing represented by the processing of the identify matching VCGs component illustrated in FIG. 28. That component, however, may be adapted to generate a similarity score for each matching VCG so that the PSMD system may select the VCG, and thus the model, that is most similar to the patient. Alternatively, the PSMD system may generate values for the pixels of the map based on a weighted combination (e.g., an average) of the values of the EM mesh for all the matching models. The PSMD system may also weight the values based on the similarity scores of the matching models.

In some embodiments, the PSMD system may generate a sequence of maps for display as a video representation of activation of patient's EM source over time. For example, the PSMD may divide the cycle into 30 display intervals and generate a map for each display interval based on values of an EM mesh corresponding to that display interval. The PSMD system may then display the 30 maps in sequence over the time of the cycle to provide a video based on the actual cycle time or in sequence over a time longer than the cycle to provide a slow-motion effect. The PSMD system may also achieve a slow-motion effect by generating more maps per second of simulation time than the maximum frame rate for the display. For example, if the maximum frame rate is 60 frames-per-second, then generating 120 maps per second of simulation will result in one second of simulation time being displayed over two seconds. The slowest and smoothest slow-motion effect may be achieved by generating a map from the voltage solution for each simulation time.

Figure 37:
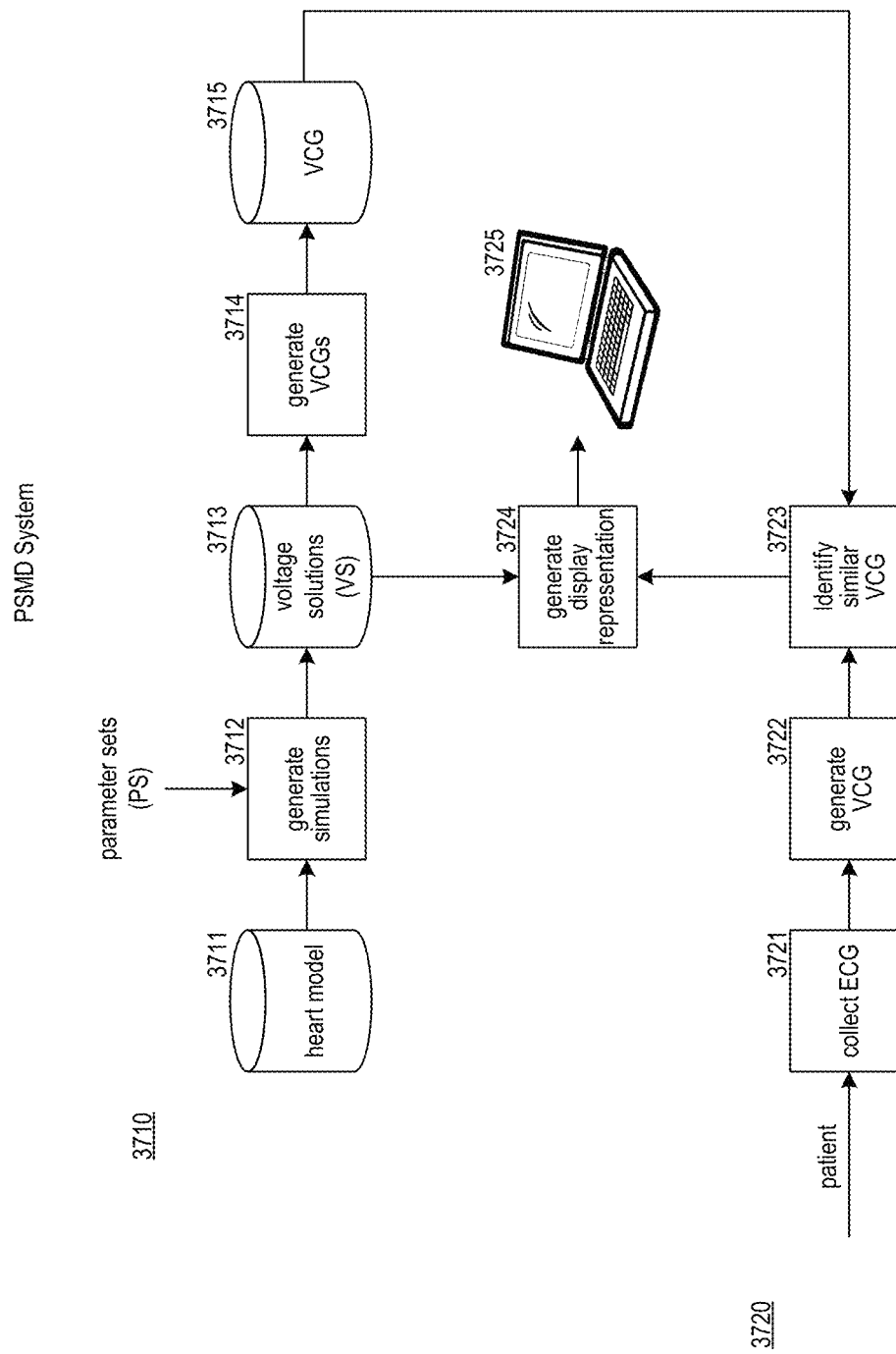
FIG. 37 is a block diagram that illustrates the overall processing of a patent-specific model display system in some embodiments.

FIG. 37 is a block diagram that illustrates the overall processing of a patent-specific model display system in some embodiments. Components 3710 (i.e., components 3711-15) are similar to components 111-115 of FIG. 1. Components 3720 include a collect ECG component 3721, a generate VCG component 3722, an identify similar VCG component 3723, a generate display representation component 3724, and a display device 3725. The collect ECG component receives an ECG for the patient whose heart is to be represented by the output of the PSMD system. The generate VCG component receives the patient's ECG and generates a VCG for the patient. The identify similar VCG component compares the patient VCG to the modeled VCGs of the VCG store to identify a modeled VCG that is similar to the patient VCG. Similar VCGs may be identified based on comparison of cycles of the VCGs. Thus, the identify similar VCG component may invoke an identify cycles component to identify the cycles of each VCG. The generate display representation component inputs the similar modeled VCG and generates a display representation of the patient's heart based on the voltage solutions from which the similar modeled VCG was derived. The generate display representation component then outputs the display representation to the display device.

Figure 38:
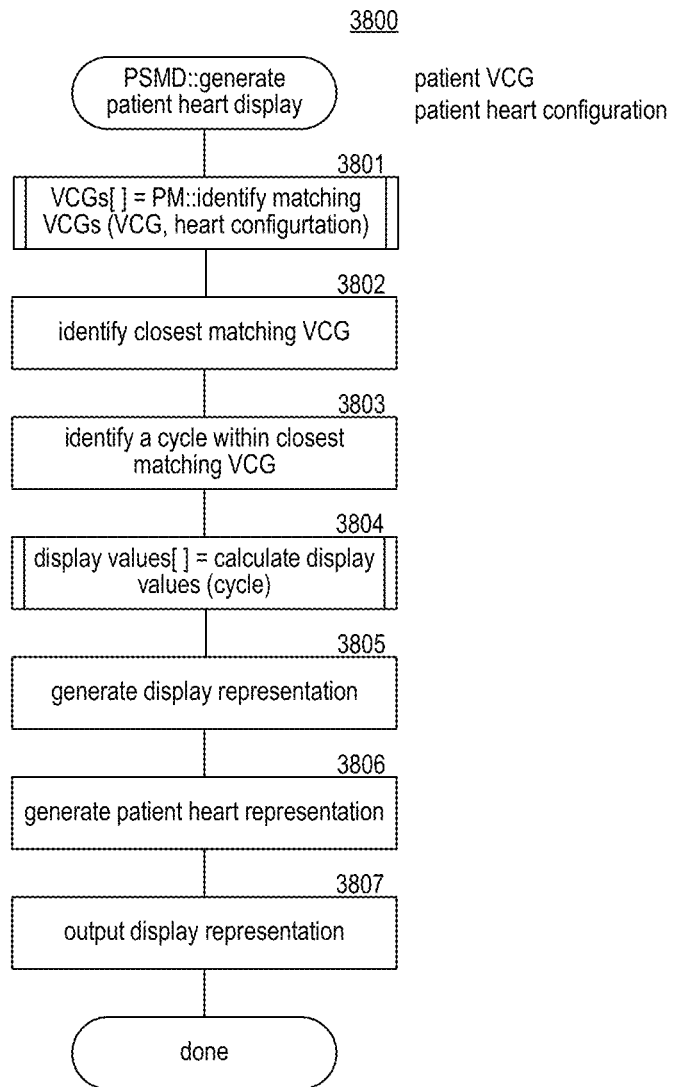
FIG. 38 is a flow diagram that illustrates the processing of a generate patient heart display component of the PSMD system in some embodiments.

FIG. 38 is a flow diagram that illustrates the processing of a generate patient heart display component of the PSMD system in some embodiments. The generate patient heart display component 3800 is provided a patient VCG and a patient heart configuration and generates an output representation of the patient's heart. In block 3801, the component invokes an identify matching VCGs component of the patient matching system passing an indication of the patient VCG and the patient heart configuration to identify one or more matching VCGs. In block 3802, the component identifies the closest matching of the VCGs. In block 3803, the component identifies a cycle within the closest matching VCG. In block 3804, the component invokes the calculate display values component passing an indication of the identified cycle to generate display values for map. In block 3805, the component generates the display representation by storing the display values in the map. In block 3805, the component display values in the map to represent an outline of the patient's heart based on anatomical parameters of that patient. In block 3807, the component outputs the map and completes.

Figure 39:
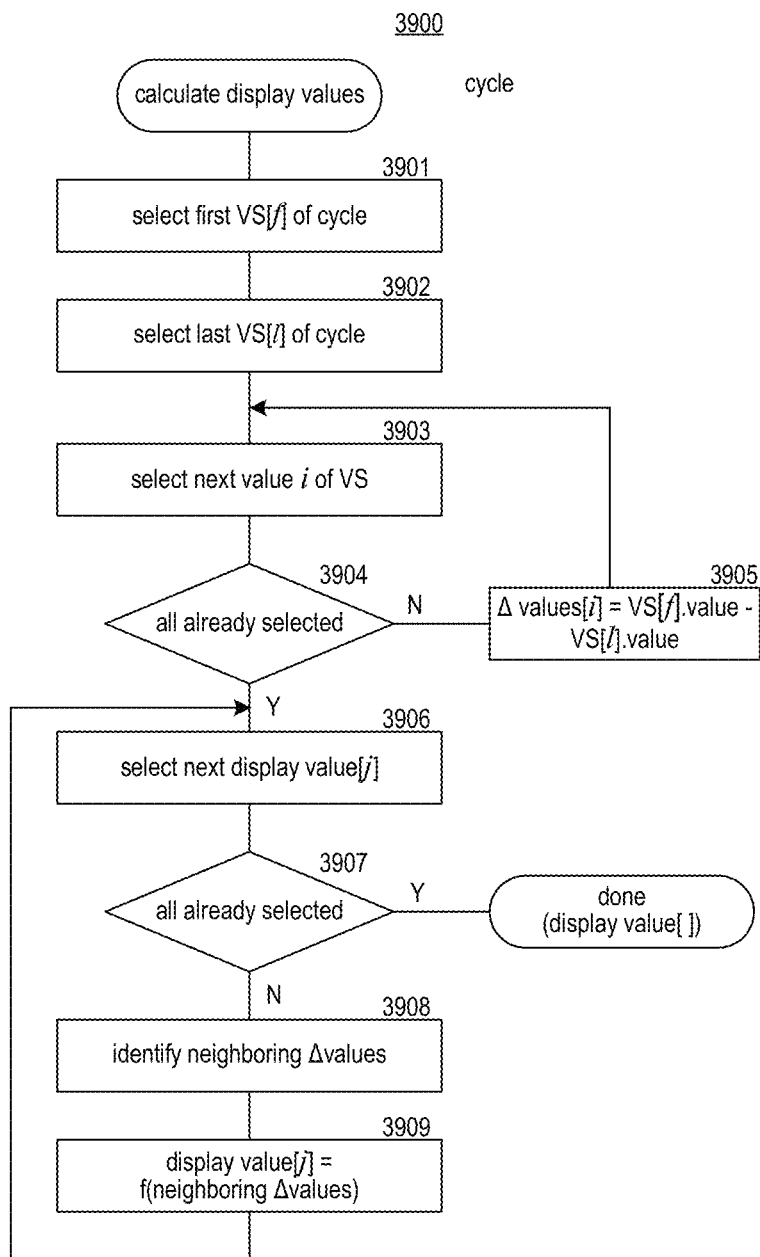
FIG. 39 is a flow diagram that illustrates the processing of a calculate display values component of the PSMD system in some embodiments.

FIG. 39 is a flow diagram that illustrates the processing of a calculate display values component of the PSMD system in some embodiments. The calculate display values component 3900 is passed an indication of a cycle and generates display values based on EM meshes of that cycle. In block 3901, the component selects the first voltage solution of the cycle. In block 3902, the component selects another voltage solution of the cycle such as the last voltage solution. In block 3903, the component selects the next value of a voltage solution. In decision block 3904, if all the values of already been selected, then the component continues at block 3906, else the component continues at block 3905. In block 3905, the component sets a delta value for the selected value to the difference between the value for the first voltage solution and the last voltage solution of the cycle. The delta value may alternatively be weight accumulation of the differences over a cycle. The component then loops to block 3903 to select the next value of the voltage solution. In block 3906, the component selects the next display value of the map. In decision block 3907, if all the display values have already been selected, then the component completes indicating the display values, else the component continues at block 3908. In block 3908, the component identifies neighboring delta values that are near the display value. In block 3910, the component sets the display value to a function of the neighboring delta values and then loops to block 3906 to select the next display value. The function may take the average of the neighboring delta values, a weighted average based on distance between the location of the voltage solution and the location and the patient heart that the display value represents, and so on.

Display of an Electromagnetic Force

Methods and systems for generating a visual representation of an electromagnetic force generated by an electromagnetic source within a body is provided. In some embodiments, an electromagnetic force display ("EFD") system generates a "surface representation" of the electromagnetic force from a sequence of vectors representing magnitude and direction of the electromagnetic force over time. For example, when the electromagnetic source is a heart, the sequence of vectors may be a vectorcardiogram. The vectors are relative to an origin, which may be located within the electromagnetic source. To generate the surface representation, the EFD system, for pairs of vectors adjacent in time, identifies a region based on the origin and the pair of vectors. For example, if a vector has the values (1.0, 2.0, 2.0) for its x, y, and z coordinates and the adjacent vector has values (1.1, 2.0, and 2.0), then the region is the area bounded by the triangle with the vertices at (0.0, 0.0, 0.0), (1.0, 2.0, 2.0), and (1.1, 2.0, and 2.0). The EFD system then displays a representation of each region to form the surface representation of the electromagnetic force. Since the regions will unlikely lie in one plane, the EFD system may provide shading or coloring to help illustrate that the regions lie in different planes. The EFD system may also display a representation of the electromagnetic source so that the surface representation visually emanates from the electromagnetic source. For example, the EFD system may display a heart that is based on the anatomical parameters of a patient from whom the VCG was collected. When the electromagnetic force has cycles, the regions for a cycle form a surface representation for that cycle. The EFD system may simultaneously display surface representations for multiple cycles. For example, when the electromagnetic source is a heart, the cycle may be based on an arrhythmia. The EFD system may also display the surface representation of each cycle in sequence (e.g., centered at the same location on the display) illustrate changes in the electromagnetic force over time. The EFD system may display each region of a surface representation in sequence to illustrate the times associated with the vectors. The EFD system may be used display either simulated VCGs or VCGs collected from patients.

Figure 40:
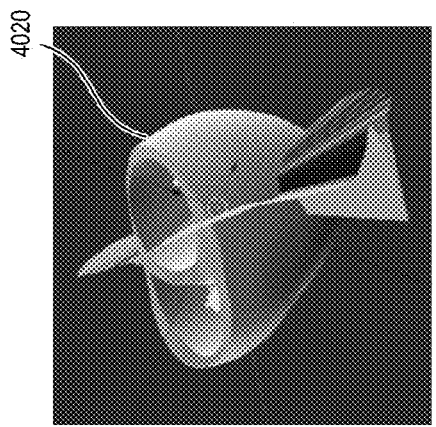
FIG. 40 illustrates various surface representations of vectorcardiograms.
Figure 40:
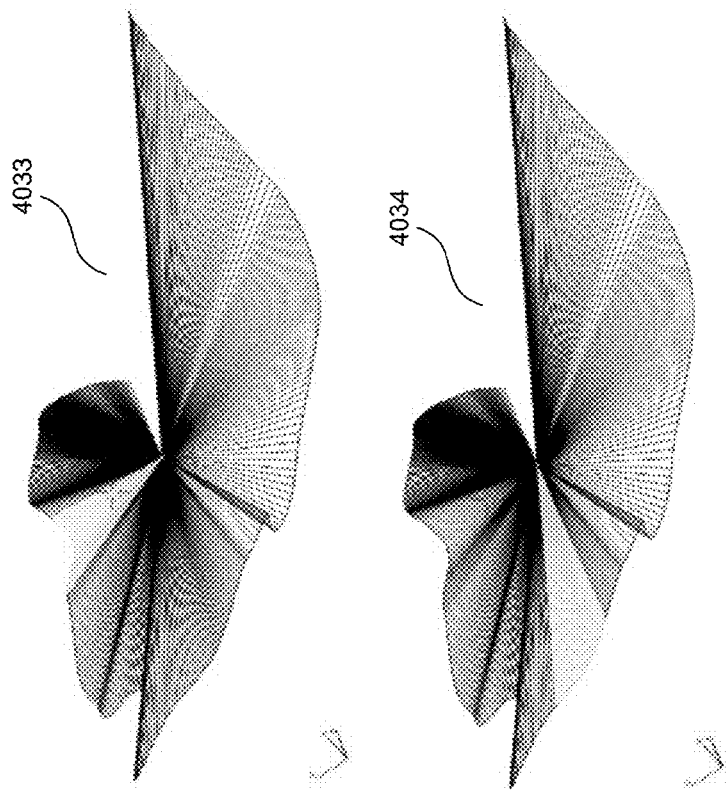
Figure 40:
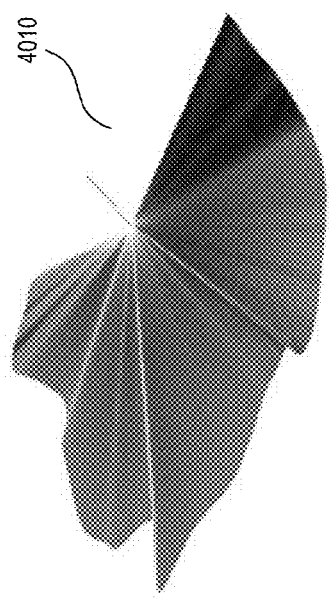
Figure 40:
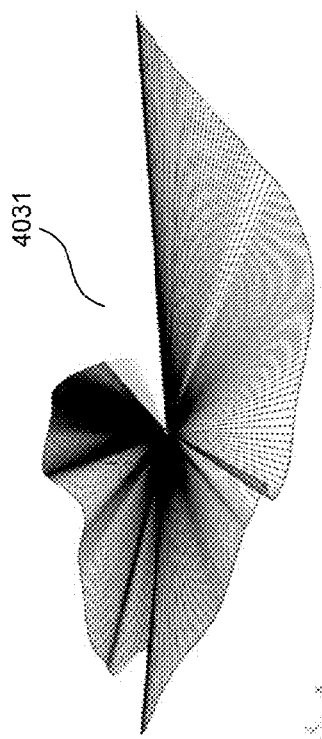
Figure 40:
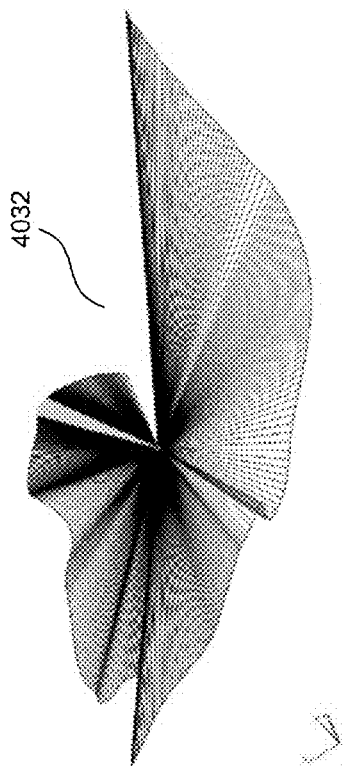

FIG. 40 illustrates various surface representations of vectorcardiograms. Image 4010 illustrates a display of a surface representation of a vectorcardiogram based on a perspective view. Image 4020 illustrates a display of a surface representation of vectorcardiogram shown as emanating from a heart. Images 4031-34 illustrate display of the surface representation over time to illustrate changes in the electromagnetic force.

In some embodiments, the EFD system may employ a variety of animation techniques to assist a user in analyzing a VCG. For example, the EFD system may animate the display of the surface representation by displaying each region in sequence with a timing that is the same as the actual timing of the VCG. If a cycle is 1000 ms, then EFD system would display the regions in sequence over 1000 ms. When displaying the surface representations for multiple cycles in sequence and the next region to display would overlap a region previously displayed, then the EFD system may first remove the region that would be overlapped and then display the next region. The EFD system may also allow the user to specify that only a portion of the surface representation for a cycle be displayed. For example, the user may specify to display a portion corresponding to 250 ms of the surface representation. In such a case, the EFD system may animate the display of the portion by removing the tail region when adding a head region. The EFD system may also allow the user to speed up or slow down the display of the surface representations.

Figure 41:
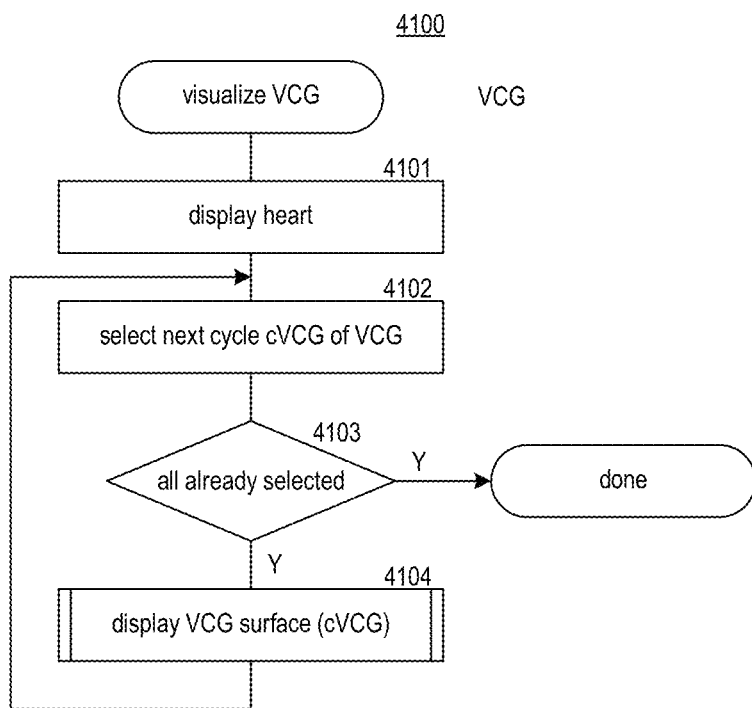
FIG. 41 is a flow diagram that illustrates the processing of a visualize VCG component of the EFD system in some embodiments.

FIG. 41 is a flow diagram that illustrates the processing of a visualize VCG component of the EFD system in some embodiments. The visualize VCG component 4100 is passed a VCG and generates a surface representation for each portion (e.g., cycle) of the VCG. In block 4101, the component displays a representation of a heart. In block 4102, the component selects the next cycle of the VCG. In decision block 4103, if all the cycles have already been selected, then the component completes, else the component continues at block 4104. In block 4104, the component invokes a display VCG surface representation component to display a surface representation for the selected cycle and then loops to block 4102 to select the next cycle.

Figure 42:
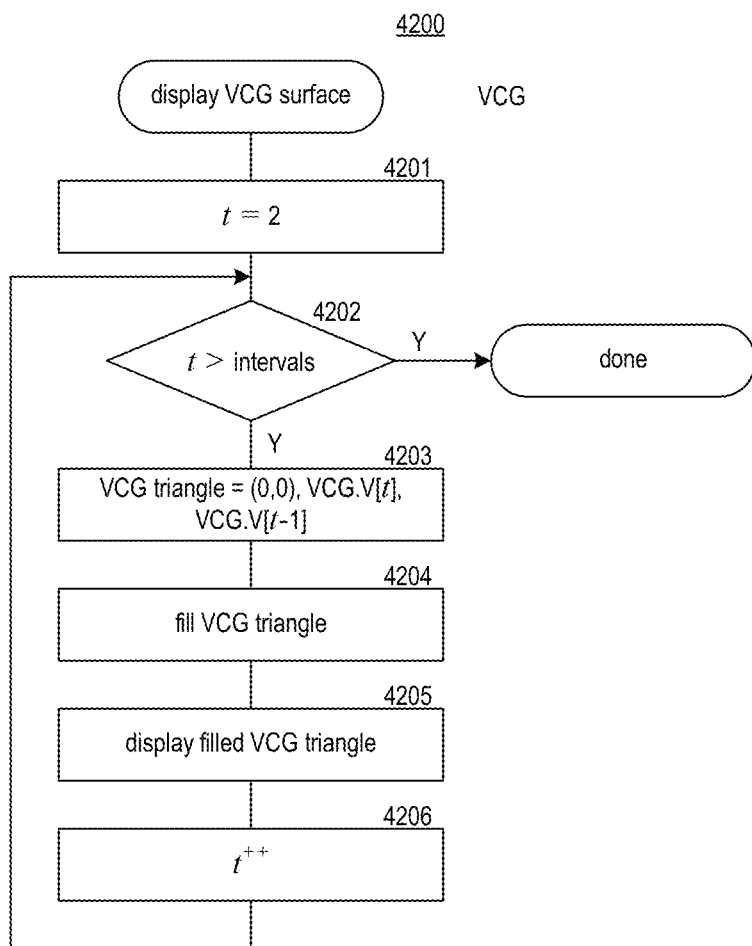
FIG. 42 is a flow diagram that illustrates the processing of a display VCG surface representation component of the EFD system in some embodiments.

FIG. 42 is a flow diagram that illustrates the processing of a display VCG surface representation component of the EFD system in some embodiments. The display VCG surface representation component 4200 is passed a vectorcardiogram and generates a surface display representation of the VCG. In block 4201, the component sets an index t to 2 for indexing through the time intervals of the VCG. In decision block 4002, if the index t is greater than the number of time intervals, then the component completes, else the component continues at block 4203. In block 4203, the component generates a VCG triangle based on the origin, the indexed interval t, and the prior interval t−1. In block 4204, the component fills the VCG triangle with a shading that may vary based on the plane of the triangle. In block 4205, the component displays the filled VCG triangle. In block 4206, the component increments the index t. In decision block 4207, if the index t is greater than the display span $t_{span}$+1, then the component continues at block 4208, else the component loops to block 4202. In block 4208, the component removes from the display the VCG triangle at the beginning of the currently displayed span and loops to block 4202.

The following paragraphs describe various embodiments of aspects of the MLMO system. An implementation of the MLMO system may employ any combination of the embodiments. The processing described below may be performed by a computing system with a processor that executes computer-executable instructions stored on a computer-readable storage medium that implements the MLMO system.

In some embodiments, a method performed by one or more computing systems is provided for generating a classifier for classifying electromagnetic data derived from an electromagnetic source within a body. The method accesses a computational model of the electromagnetic source, wherein the computational model is for modeling electromagnetic output of the electromagnetic source over time based on a source configuration of the electromagnetic source. For each of a plurality of source configurations, the method generates, using the computational model, a modeled electromagnetic output of the electromagnetic source for that source configuration. The method, for each modeled electromagnetic output, derives the electromagnetic data for the modeled electromagnetic output and generates a label for the derived electromagnetic data based on the source configuration for the modeled electromagnetic data. The method trains a classifier with the derived electromagnetic data and the labels as training data. In some embodiments, the modeled electromagnetic output for a source configuration includes, for each of a plurality of time intervals, an electromagnetic mesh with a modeled electromagnetic value for each of a plurality of locations of the electromagnetic source. In some embodiments, the derived electromagnetic data, for a time interval, is an equivalent source representation of the electromagnetic output. In some embodiments, the equivalent source representation is generated using principal component analysis. In some embodiments, the method further identifies cycles within the derived electromagnetic data for a modeled electromagnetic output. In some embodiments, the same label is generated for each cycle. In some embodiments, the method further identifies a sequence of cycles that are similar, wherein the same label is generated for each sequence. In some embodiments, the deriving of the electromagnetic data for a modeled electromagnetic output includes normalizing the modeled electromagnetic output on a per-cycle basis. In some embodiments, the classifier is a convolutional neural network. In some embodiments, the convolutional neural network inputs a one-dimensional image. In some embodiments, the classifier is a recurrent neural network, an autoencoder, a restricted Boltzmann machine, or other type of neural network. In some embodiments, the classifier is a support vector machine. In some embodiments, the classifier is Bayesian. In some embodiments, the electromagnetic source is a heart, a source configuration represents a source location and other properties of a heart disorder, the modeled electromagnetic output represents activation of the heart, and the electromagnetic data is based on body-surface measurements such as an electrocardiogram. In some embodiments, the heart disorder is selected from a set consisting of inappropriate sinus tachycardia ("IST"), ectopic atrial rhythm, junctional rhythm, ventricular escape rhythm, atrial fibrillation ("AF"), ventricular fibrillation ("VF"), focal atrial tachycardia ("focal AT"), atrial microreentry, ventricular tachycardia ("VT"), atrial flutter ("AFL"), premature ventricular complexes ("PVCs"), premature atrial complexes ("PACs"), atrioventricular nodal reentrant tachycardia ("AVNRT"), atrioventricular reentrant tachycardia ("AVRT"), permanent junctional reciprocating tachycardia ("PJRT"), and junctional tachycardia ("JT").

In some embodiments, a method performed by a computing system is provided for classifying electromagnetic output collected from a target that is an electromagnetic source within a body. The method accesses a classifier to generate a classification for electromagnetic output of an electromagnetic source. The classifier is trained using training data generated from modeled electromagnetic output for a plurality of source configurations of an electromagnetic source. The modeled electromagnetic output is generated using a computational model of the electromagnetic source that models the electromagnetic output of the electromagnetic source over time based on a source configuration. The method collects target electromagnetic output from the target. The method applies the classifier to the target electromagnetic output to generate a classification for the target. In some embodiments, the training data is generated by running, for each of the source configurations, a simulation that generates an electromagnetic mesh for each of a plurality of simulation intervals, each electromagnetic mesh having an electromagnetic value for a plurality of locations of the electromagnetic source. In some embodiments, the electromagnetic source is a heart, a source configuration represents a source location of a heart disorder, and the modeled electromagnetic output represents activation of the heart, and the classifier is trained using electromagnetic data derived from an electrocardiogram representation of the electromagnetic output.

In some embodiments, one or more computing systems are provided for generating a classifier for classifying electromagnetic output of an electromagnetic source. The one or more computing systems include one or more computer-readable storage mediums and one or more processors for executing the computer-executable instructions stored in the one or more computer-readable storage mediums. The one or more computer-readable storage mediums store a computational model of the electromagnetic source. The computational model models electromagnetic output of the electromagnetic source over time based on a source configuration of the electromagnetic source. The one or more computer-readable storage mediums store computer-executable instructions for controlling the one or more computing systems to, for each of a plurality of source configurations, generate training data from the electromagnetic output of the computational model that is based on the source configuration and train the classifier using the training data. In some embodiments, the computer-executable instructions that generate the training data for a source configuration further control the one or more computing systems to generate derived electromagnetic data from the electromagnetic output for the source configuration and generate a label for the electromagnetic data based on the source configuration.

In some embodiments, a method performed by a computing system generating a simulated anatomy of an electromagnetic source within a body is provided. The method accesses seed anatomies of the electromagnetic source. Each seed anatomy has a seed value for each of a plurality of anatomical parameters of the electromagnetic source. The method accesses a set of weights that includes a weight for each seed anatomy. For each of the anatomical parameters, the method generates a simulated value for that anatomical parameter by combining the seed values for that anatomical parameter, factoring in the weights of the seed anatomies. In some embodiments, the method validates the simulated anatomy based on comparison to values for anatomical parameters found in a population. In some embodiments, the anatomical parameters include dimensions of the electromagnetic source and wherein a simulated value for a dimension is validated when a patient in the population includes value for that dimension that is approximately the same as the simulated value. In some embodiments, the anatomical parameters of the seed anatomies are collected by scanning actual electromagnetic sources within bodies. In some embodiments, the electromagnetic source is a heart. In some embodiments, the method generates a simulated value for an anatomical parameter based on a weighted average of the seed values for that anatomical parameter. In some embodiments, the method further generates a plurality of simulated anatomies wherein each simulated anatomy is based on a different set of weights.

In some embodiments, a computing system for generating simulated anatomies of a heart is provided. The computing system comprises one or more computer-readable storage mediums storing seed anatomies of a heart. Each seed anatomy having a seed value for each of a plurality of anatomical parameters of a heart. The one or more computer-readable storage mediums also stores sets of weights that each includes a weight for each seed anatomy. The one or more computer-readable storage mediums store computer-executable instructions for controlling the computing system to, for each set of weights and for each of the anatomical parameters for that set of weights, generate a simulated value for that anatomical parameter by combining the seed values for that anatomical parameter, factoring in the weights of the seed anatomies. The computing system further comprises one or more processors for executing the computer-executable instructions stored in the one or more computer-readable storage mediums. In some embodiments, the instructions further control the computing system to validate each simulated anatomy based on comparison to values for anatomical parameters found in a population. In some embodiments, the anatomical parameters include thickness of walls of a heart and dimensions of a chamber of the heart. In some embodiments, a simulated value for a dimension is validated when a patient in the population includes value for that dimension that is approximately the same as the simulated value. In some embodiments, the seed anatomies represent extremes of hearts found in a population. In some embodiments, the anatomical parameters of the seed anatomies are collected by scanning hearts. In some embodiments, the generating of a simulated value for an anatomical parameter is based on a weighted average of the seed values for that anatomical parameter. In some embodiments, a method performed by a computing system for generating an arrhythmia model library for modeling a heart is provided. The method accesses simulated anatomies of anatomical parameters of the heart. The simulated anatomies are generated based on seed anatomies of anatomical parameters of the heart and sets of weights that include a weight for each seed anatomy. The method accesses configuration parameters that include one or more of torso anatomy, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, and other normal and pathophysiologic feature distributions within the heart, action potential dynamics for the heart, sets of conductivities for the heart, arrhythmia source locations within the heart, and so on. The method establishes source configurations that are each based on a simulated anatomy and a combination of electrophysiology parameters. For each of a plurality of the source configurations, the method generates a mesh based on the simulated anatomy of that source configuration, the mesh having vertices, and for each vertex of the mesh, generates model parameters of a computational model of the heart based on the combination of electrophysiology parameters of that source configuration. The computational model for modeling electromagnetic propagation at that vertex based on the electrophysiology parameters of that source configuration. In some embodiments, the method generates a simulated anatomy by accessing seed anatomies of a heart where each seed anatomy has a seed value for each of the anatomical parameters of the heart; accesses a set of weights that includes a weight for each seed anatomy; and for each of the anatomical parameters, generates a simulated value for that anatomical parameter by combining the seed values for that anatomical parameter, factoring in the weights of the seed anatomies. In some embodiments, the simulated anatomies are validated based on comparison to values for anatomical parameters found in a population. In some embodiments, the anatomical parameters of the seed anatomies are collected by scanning actual hearts. In some embodiments, for each of a plurality of source configurations, the method generates a modeled electromagnetic output of the heart for that source configuration using a computational model for the heart. In some embodiments, for each source configuration, the method generates training data for the modeled electromagnetic output that is based on that source configuration; and trains a classifier for classifying electromagnetic output of the heart using the training data.

In some embodiments, a computing system for generating a model library of models of an electromagnetic source within a body is provided. The computing system comprises one or more computer-readable storage mediums storing computer-executable and one or more processors for executing the computer-executable instructions stored in the one or more computer-readable storage mediums. The instructions control the computing system to generate simulated anatomies of anatomical parameters of the electromagnetic source from seed anatomies and generate source configurations that are each based on a simulated anatomy and a combination of configuration parameters. The instructions control the computing system to, for each of a plurality of the source configurations, generate a mesh based on the simulated anatomy of that source configuration, the mesh having vertices; and for each vertex of the mesh, generate model parameters of a computational model of the electromagnetic source based on the combination of configuration parameters of that source configuration. In some embodiments, the computational model for modeling electromagnetic propagation at a vertex is based on the configuration parameters of a source configuration. In some embodiments, the simulated anatomies are generated based on anatomical parameters of the seed anatomies and sets of weights that include a weight for each seed anatomy. In some embodiments, the electromagnetic source is a heart and the configuration parameters include one or more of torso anatomy, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, and other normal and pathophysiologic feature distributions within the heart, action potential dynamics for the heart, sets of conductivities for the heart, and arrhythmia source locations within the heart. In some embodiments, the simulated anatomies are validated based on comparison to values for anatomical parameters found in a population. In some embodiments, the anatomical parameters of the seed anatomies are collected by scanning actual electromagnetic sources. In some embodiments, the computer-executable instructions further control the computing system to, for each of a plurality of source configurations, generate a modeled electromagnetic output of the electromagnetic source for that source configuration using a computational model for the electromagnetic source. In some embodiments, computer-executable instructions further control the computing system to for each source configuration, generate training data for the modeled electromagnetic output that is based on that source configuration; and train a classifier for classifying electromagnetic output of the electromagnetic source using the training data.

In some embodiments, a method performed by a computing system for generating a model library of models of an electromagnetic source within a body is provided. The method accesses simulated anatomies of anatomical parameters of the electromagnetic source. The method generates source configurations that are each based on a simulated anatomy and a combination of configuration parameters. For each of a plurality of the source configurations, the method generates a model based on the simulated anatomy of that source configuration, the combination of configuration parameters of that source configuration, and a computational model of the electromagnetic source. In some embodiments, the generating of a model includes generating a mesh based on the simulated anatomy of that source configuration and, for each vertex of the mesh, generating model parameters of a computational model of the electromagnetic source based on the combination of configuration parameters of that source configuration. In some embodiments, the computational model is for modeling electromagnetic propagation at a vertex based on the configuration parameters of a source configuration. In some embodiments, the electromagnetic source is a heart and the models are arrhythmia models. In some embodiments, the method further generates the simulated anatomies based on anatomical parameters of seed anatomies and sets of weights that include a weight for each seed anatomy. In some embodiments, the electromagnetic source is a heart and the configuration parameters include one or more of a human torso, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, and other normal and pathophysiologic feature distributions within the heart, action potential dynamics for the heart, sets of conductivities for the heart, arrhythmia source locations within the heart, and so on.

In some embodiments, a method performed by a computing system for presenting weights for a simulated anatomy of a body part is provided. The method accesses seed anatomies of the body part. Each seed anatomy has a seed value for each of a plurality of anatomical parameters of the body part. For each of a plurality of seed anatomies of the body part, the method displays a seed representation of the body part based on seed values of anatomical parameters of that seed anatomy. The method accesses a set of weights that includes a weight for each seed anatomy. The method displays a simulated representation of the body part based on a simulated value for each anatomical parameter by, for each anatomical parameter, combining the seed values of the seed anatomies of that anatomical parameter, factoring in the weights of the seed anatomies. In some embodiments, the seed representations are displayed in a circular arrangement with the simulated representation displayed within the circular arrangement.

In some embodiments, the method further displays, in association with each displayed seed representation for a seed anatomy, an indication of the weight associated with that seed anatomy. In some embodiments, the method further displays a line between each displayed seed representation and the displayed simulated representation, wherein the displayed indication of the weight for a seed anatomy is displayed in association with the displayed line between the displayed seed representation for that seed anatomy and the displayed simulated representation. In some embodiments, the method further provides a user interface element for specifying the weight for each seed anatomy. In some embodiments, the method provides a user interface element for specifying a plurality of sets of weights, with each set including a weight for each seed anatomy. In some embodiments, the plurality of sets of weights are specified by providing a range of weights and an increment. In some embodiments, the body part is a heart. In some embodiments, the body part is a lung. In some embodiments, the body part is a torso surface.

In some embodiments, a computing system for presenting a simulated anatomy of a body part is provided. The computing system comprises one or more computer-readable storage mediums storing computer-executable instructions and one or more processors for executing the computer-executable instructions stored in the one or more computer-readable storage mediums. The instructions control the computing system to for each of a plurality of seed anatomies of the body part, display a seed representation of the body part based on seed values of anatomical parameters of that seed anatomy; and display a simulated representation of the body part based on a simulated anatomy with simulated values for anatomical parameters derived from a weighted combination of the seed values of the seed anatomies for the anatomical parameters. In some embodiments, the computer-executable instructions further control the computing system to generate the simulated anatomy by, for each anatomical parameter, generating a simulated value for that anatomical parameter by combining the seed values of the seed anatomies of that anatomical parameter, factoring in weights of the seed anatomies. In some embodiments, the seed representations are displayed in a circular arrangement with the simulated representation displayed within the circular arrangement. In some embodiments, the computer-executable instructions further control the computing system to display, in association with each displayed seed representation for a seed anatomy, an indication of a weight associated with that seed anatomy. In some embodiments, the computer-executable instructions further control the computing system to provide a user interface for specifying a plurality of sets of weights, with each set including a weight for each seed anatomy. In some embodiments, the plurality of sets of weights are specified by a range of weights and an increment.

In some embodiments, a method performed by a computing system for presenting a simulated anatomy of a heart is provided. For each of a plurality of seed anatomies of the heart, the method displays a seed representation of the heart based on seed values of anatomical parameters of that seed anatomy. The method displays a simulated representation of the heart based on a simulated anatomy derived, for each anatomical parameter, from a simulated value for that anatomical parameter generated from a weighted combination of the seed values of the seed anatomies for that anatomical parameter. In some embodiments, the seed representations are displayed in a circular arrangement with the simulated representation displayed within the circular (e.g., bullseye) arrangement. In some embodiments, the method further displays, in association with each displayed seed representation for a seed anatomy, an indication of a weight associated with that seed anatomy.

In some embodiments, a method performed by a computing system for converting a first polyhedral model to a second polyhedral model is provided. The first polyhedral model has a first polyhedral mesh with a volume containing first polyhedrons. Each vertex of the first polyhedrons has a model parameter. The method generates a representation of the surface of the first polyhedral model from the first polyhedrons. The method generates a second polyhedral mesh for the second polyhedral model by populating the volume with the surface with second polyhedrons that are different from the first polyhedrons. For each of a plurality of vertices of the second polyhedrons of the second polyhedral mesh, the method interpolates a model parameter for that vertex based on the parameters of vertices of the first polyhedrons that are proximate to that vertex. In some embodiments, the first polyhedrons are hexahedrons and the second polyhedrons are tetrahedrons. In some embodiments, the polyhedral meshes represent a body part. In some embodiments, the body part is a heart. In some embodiments, the first polyhedral mesh has an origin and further comprising, prior to interpolating the model parameters, mapping the second polyhedral mesh to the same origin. In some embodiments, each vertex of the first polyhedrons has multiple parameters and the interpolating interpolates each model parameter. In some embodiments, the first polyhedral model and the second polyhedral model represent computational models of an electromagnetic source within a body, and the method further generates a modeled electromagnetic output of the electromagnetic source based on the second polyhedral model using a problem solver adapted to operate on meshes with second polyhedrons. In some embodiments, the electromagnetic source is a heart, and the method further generates a vectorcardiogram from the modeled electromagnetic output. In some embodiments, the first polyhedral model and the second polyhedral model are geometric models (e.g., of cardiac or torso anatomy). In some embodiments, the first polyhedral model and the second polyhedral model represent models of an electromagnetic source within a body, and the method further converts a plurality of first polyhedral models representing different source configurations. In some embodiments, the electromagnetic source is a heart and a source configuration specifies one or more of a fiber architecture, torso anatomy, normal and abnormal cardiac anatomy, normal and abnormal cardiac tissue, scar, fibrosis, inflammation, edema, accessory pathways, congenital heart disease, malignancy, sites of prior ablation, sites of prior surgery, sites of external radiation therapy, pacing leads, implantable cardioverter-defibrillator leads, cardiac resynchronization therapy leads, pacemaker pulse generator location, implantable cardioverter-defibrillator pulse generator location, subcutaneous defibrillator lead location, subcutaneous defibrillator pulse generator location, leadless pacemaker location, other implanted hardware (e.g., right or left ventricular assist devices), external defibrillation electrodes, surface ECG leads, surface mapping leads, a mapping vest, and other normal and pathophysiologic feature distributions within the heart, action potential dynamics, conductivities, arrhythmia source location or locations, and so on.

In some embodiments, a computing system for converting a first polyhedral model of a body part to a second polyhedral model of the body part is provided. The computing system comprises one or more computer-readable storage mediums storing computer-executable instructions and one or more processors for executing the computer-executable instructions stored in the one or more computer-readable storage mediums. The instructions for controlling the computing system to generate a representation of the surface of the first polyhedral model. The first polyhedral model has a first polyhedral mesh based on a first polyhedron. The instructions for controlling the computing system to generate a second polyhedral mesh for the second polyhedral model by populating the volume with the surface based on a second polyhedron that is different from the first polyhedron. The instructions for controlling the computing system to for each of a plurality of vertices of second polyhedrons of the second polyhedral mesh, interpolate a model parameter for that vertex based on the parameters of vertices of first polyhedrons of the first polyhedral mesh that are proximate to that vertex. In some embodiments, the first polyhedron is a hexahedron and the second polyhedron is a tetrahedron. In some embodiments, the first polyhedral mesh has an origin and wherein the computer-executable instructions further control the computing system to, prior to interpolating the model parameters, map the second polyhedral mesh to the same origin. In some embodiments, the first polyhedral model and the second polyhedral model represent computational models of the heart and wherein the computer-executable instructions further control the computing system to generate a modeled electromagnetic output of the electromagnetic heart based on the second polyhedral model using a problem solver adapted to operate on meshes with second polyhedrons. In some embodiments, the computer-executable instructions further control the computing system to generate a vectorcardiogram from the modeled electromagnetic output. In some embodiments, the first polyhedral model and the second polyhedral model are geometric models (e.g., of cardiac or torso anatomy).

In some embodiments, a method performed by a computing system for converting a first polyhedral model to a second model is provided. The first polyhedral model has a first polyhedral mesh with a volume containing first polyhedrons. Each vertex of the first polyhedrons has a model parameter. The method generates a representation of the surface of the first polyhedral model from the first polyhedrons. For each of a plurality of points of a second model, the method interpolates a model parameter for that point based on the parameters of vertices of the first polyhedrons that are considered proximate to that vertex. In some embodiments, the second model is a second polyhedral model and the points are vertices of the second polyhedral model. In some embodiments, the second model is represented by regularly spaced grid points and the points are grid points.

In some embodiments, a method performed by a computing device for generating derived electromagnetic data for an electromagnetic source within a body is provided. The method accesses modeled electromagnetic output for a first model of the electromagnetic source over time. The first model is based on a first source configuration specifying a first anatomy. The modeled electromagnetic output is generated using a computational model of the electromagnetic source. The computational model is for generating modeled electromagnetic output of the electromagnetic source over time based on a model based on a source configuration. The method accesses a second model of the electromagnetic source based on a second source configuration specifying a second anatomy. The method generates derived electromagnetic data for the second model of the electromagnetic source based on the modeled electromagnetic output for the first model of the electromagnetic source, factoring in differences between the first anatomy and the second anatomy. In some embodiments, the electromagnetic source is a heart and the derived electromagnetic data is a cardiogram. In some embodiments, the cardiogram is a vectorcardiogram. In some embodiments, the cardiogram is an electrocardiogram. In some embodiments, the modeled electromagnetic output for a model includes, for each of a plurality of time intervals, an electromagnetic mesh with a modeled electromagnetic value for each of a plurality of vertices of the electromagnetic mesh. In some embodiments, the modeled electromagnetic output is a collection of voltage solutions.

In some embodiments, a computing system for generating a cardiogram for a heart is provided. The computing system comprises one or more computer-readable storage mediums storing a modeled electromagnetic output for a first arrhythmia model of the heart over time. The first arrhythmia model is based on a first anatomy. The modeled electromagnetic output is generated using a computational model of a heart, the computational model for generating modeled electromagnetic output of the heart over time based on an arrhythmia model. The one or more computer-readable storage mediums store a second arrhythmia model based on a second anatomy. The one or more computer-readable storage mediums store computer-executable instructions for controlling the computing system to generate a cardiogram for the second arrhythmia model based on the modeled electromagnetic output for the first arrhythmia model, factoring in differences between the first anatomy and the second anatomy. The computing system comprising one or more processors for executing the computer-executable instructions stored in the one or more computer-readable storage mediums. In some embodiments, the cardiogram is a vectorcardiogram. In some embodiments, the cardiogram is an electrocardiogram. In some embodiments, the modeled electromagnetic output for an arrhythmia model includes, for each of a plurality of time intervals, an electromagnetic mesh with a modeled electromagnetic value for each of a plurality of vertices of the electromagnetic mesh. In some embodiments, the modeled electromagnetic output is a collection of voltage solutions.

In some embodiments, a method performed by a computing system for bootstrapping the generating of modeled electromagnetic output of an electromagnetic source within a body is provided. The method accesses first modeled electromagnetic output for a first model with a first source configuration of the electromagnetic source at first simulation intervals. The first modeled electromagnetic output is generated using a computational model of the electromagnetic source. The method initializes second modeled electromagnetic output for a second model with a second source configuration of the electromagnetic source to a first modeled electromagnetic output for one of the first simulation intervals. For each of a plurality of second simulation intervals, the method generates using the computational model second modeled electromagnetic output for the second model of the electromagnetic source based on the initialized second modeled electromagnetic output. In some embodiments, the electromagnetic source is a heart and the second source configuration is different from the first source configuration based on scar or fibrosis or pro-arrhythmic substrate location within the heart. In some embodiments, the electromagnetic source is a heart and the first model and the second model are arrhythmia models. In some embodiments, the modeled electromagnetic output for a model includes, for each of a plurality of time intervals, an electromagnetic mesh with a modeled electromagnetic value for each of a plurality of vertices of the electromagnetic mesh. In some embodiments, the method further, for each of a plurality of the first simulation intervals, generates using the computational model the first modeled electromagnetic output for the first model. In some embodiments, the initializing initializes the second modeled electromagnetic output to the first modeled electromagnetic output for a first simulation interval after the first modeled electromagnetic output for the first simulation intervals has stabilized. In some embodiments, the electromagnetic source is a heart and the first modeled electromagnetic output has stabilized into a rhythm.

In some embodiments, a computing system for bootstrapping the generating of modeled electromagnetic output of a heart is provided. The computing system comprises one or more computer-readable storage mediums storing a first modeled electromagnetic output for a first arrhythmia model of the heart at first simulation intervals, the first modeled electromagnetic output generated using a computational model of a heart. The one or more computer-readable storage mediums also store computer-executable instructions for controlling the computing system to initialize second modeled electromagnetic output for a second arrhythmia model of the heart to a first modeled electromagnetic output for one of the first simulation intervals; and simulate using the computational model second modeled electromagnetic output for the second arrhythmia model based on the initialized second modeled electromagnetic output. The computing system also comprises one or more processors for executing the computer-executable instructions stored in the one or more computer-readable storage mediums. In some embodiments, the first arrhythmia model and the second arrhythmia model are based on different scar or fibrosis or pro-arrhythmic substrate locations within the heart. In some embodiments, the modeled electromagnetic output for an arrhythmia model includes, for each of a plurality of time intervals, an electromagnetic mesh with a modeled electromagnetic value for each of a plurality of vertices of the electromagnetic mesh. In some embodiments, the computer-executable instructions further control the computing system to, for each of a plurality of the first simulation intervals, generate using the computational model the first modeled electromagnetic output for the first arrhythmia model. In some embodiments, the computer-executable instructions that initialize control the computing system to initialize the second modeled electromagnetic output to the first modeled electromagnetic output for a first simulation interval after the first modeled electromagnetic output for the first simulation intervals has stabilized. In some embodiments, the first modeled electromagnetic output has stabilized into a rhythm.

In some embodiments, a method performed by a computing system for identifying derived electromagnetic data that matches patient electromagnetic data collected from a patient is provided. The electromagnetic data represents electromagnetic output an electromagnetic source within a body. The method, for each of a plurality of model source configurations of the electromagnetic source, accesses a mapping of that model source configuration to derived electromagnetic data that is derived based on that model source configuration. The method accesses a patient source configuration representing a source configuration for the electromagnetic source within the patient. The method identifies model source configurations that match the patient source configuration. The method identifies, from the derived electromagnetic data to which the identified model source configurations are mapped, derived electromagnetic data that matches the patient electromagnetic data. In some embodiments, the derived electromagnetic data is derived from modeled electromagnetic output generated based on a model source configuration using a computational model of the electromagnetic source. In some embodiments, the modeled electromagnetic data for a model source configuration includes, for each of a plurality of time intervals, an electromagnetic mesh with a modeled electromagnetic value for each of a plurality of locations of the electromagnetic source. In some embodiments, the method further, when an identified model source configuration has a value an anatomical parameter that does not match the value of that anatomical parameter of the patient source configuration, generates adjusted derived electromagnetic data based on the modeled electromagnetic output for that model source configuration and difference in the value. In some embodiments, a source configuration includes configuration parameters including anatomical parameters and electrophysiology parameters. In some embodiments, the electromagnetic source is a heart and the configuration parameters include a scar or fibrosis or pro-arrhythmic substrate location within the heart, an action potential for the heart, a conductivity for the heart, and an arrhythmia location. In some embodiments, the electromagnetic source is a heart and the anatomical parameters include dimensions of chambers of the heart, wall thicknesses of the heart, and orientation of the heart. In some embodiments, the electromagnetic source is a heart and derived electromagnetic data is a cardiogram. In some embodiments, a model source configuration includes a disorder parameter relating to an attribute of the electromagnetic source such that derived electromagnetic data for the model source configuration is based on that attribute. In some embodiments, the electromagnetic source is a heart and the attribute is based on an arrhythmia. In some embodiments, the identifying of derived electromagnetic data that matches the patient electromagnetic data is based on a Pearson correlation coefficient, a root-mean-squared error, and so on. In some embodiments, the identifying of derived electromagnetic data that matches the patient electromagnetic data is based on root-mean-squared error. In some embodiments, a source configuration includes configuration parameters, the model source configurations include a value for each configuration parameter, and the patient source configuration includes a value for only a proper subset of the configuration parameters. In some embodiments, the derived electromagnetic data is based on a model orientation of the electromagnetic source and further comprising when a patient orientation of the electromagnetic source of the patient is different from the model orientation, the identifying of the derived electromagnetic data factors in the difference between the model orientation and the patient orientation. In some embodiments, the electromagnetic source is a heart and the electromagnetic data is a vectorcardiogram and wherein the identifying of the derived electromagnetic data includes generating a rotation matrix based on the difference between the model orientation and the patient orientation and rotating a vectorcardiogram based on the rotation matrix.

In some embodiments, a method performed by a computing system for generating a classification for a patient based on patient electromagnetic data representing electromagnetic output of an electromagnetic source within the patient is provided. The method, for each of a plurality of clusters (e.g., groups) of model source configurations of the electromagnetic source, accesses a classifier for that cluster that is trained based on the model source configurations of that cluster to generate a classification for derived electromagnetic data. The method accesses a patient source configuration representing a source configuration for the electromagnetic source within the patient. The method identifies a cluster whose model source configurations matches the patient source configuration. The method applies the classifier for the identified cluster to the patient electromagnetic data to generate a classification for the patient. In some embodiments, the derived electromagnetic data is derived from modeled electromagnetic output generated based on a model source configuration using a computational model of the electromagnetic source. In some embodiments, a source configuration includes configuration parameters including anatomical parameters and electrophysiology parameters. In some embodiments, the electromagnetic source is a heart and the configuration parameters include a scar or fibrosis or pro-arrhythmic substrate location within the heart, an action potential for the heart, and a conductivity for the heart. In some embodiments, the electromagnetic source is a heart and the anatomical parameters include dimensions of chambers of the heart and wall thicknesses of the heart. In some embodiments, the electromagnetic source is a heart and derived electromagnetic data is a cardiogram. In some embodiments, the cardiogram is a vectorcardiogram. In some embodiments, a model source configuration matches the patient source configuration based on a cosine similarity. In some embodiments, the method further generates clusters of model source configurations; and for each of the clusters, for each of the model configuration sources of that cluster, generates a simulated electromagnetic output of the electromagnetic source based on that model configuration source; and generates derived electromagnetic data for that model source configuration from the simulated electromagnetic output based on that model source configuration. In some embodiments, a source configuration includes configuration parameters, the model source configurations include a value for each configuration parameter, and the patient source configuration includes a value for only a proper subset of the configuration parameters. In some embodiments, the derived electromagnetic data is based on a model orientation of the electromagnetic source, and the method further, when a patient orientation of the electromagnetic source of the patient is different from the model orientation, adjusts the patient electromagnetic data based on the difference between the model orientation and the patient orientation. In some embodiments, the electromagnetic source is a heart and the classification is based on source location of an arrhythmia.

In some embodiments, a computing system for identifying a model cardiogram that matches a patient cardiogram collected from a patient is provided. The computing system comprises one or more computer-readable storage mediums storing: for each of a plurality of model source configurations of a heart, a modeled cardiogram for that model source configuration; a patient source configuration representing the patient's heart; and computer-executable instructions that, when executed control, the computing system to: identify model source configurations that match the patient source configuration; and identify, from the modeled cardiograms for the identified model source configurations, those modeled cardiograms that match the patient cardiogram. The computing system includes one or more processor for executing the computer-executable instructions stored in the one or more computer-readable storage mediums. In some embodiments, a modeled cardiogram is generated from modeled electromagnetic output of a heart with a model source configuration using a computational model of the heart. In some embodiments, a cardiogram is adjusted based on differences in values of an anatomical parameter for a model source configuration and the patient source configuration. In some embodiments, the model source configurations include a scar or fibrosis or pro-arrhythmic substrate location within the heart, an action potential for the heart, a conductivity for the heart, and an arrhythmia location. In some embodiments, the model source configurations include dimensions of chambers of the heart, wall thicknesses of the heart, and orientation of the heart. In some embodiments, a source configuration includes configuration parameters, the model source configurations include a value for each configuration parameter, and the patient source configuration includes a value for only a proper subset of the configuration parameters. In some embodiments, modeled cardiograms are based on a model orientation of a heart and when a patient orientation of the heart is different from the model orientation, the identifying of modeled cardiograms factors in the difference between the model orientation and the patient orientation.

In some embodiments, a method performed by one or more computing systems for generating a patient classifier for classifying derived electromagnetic data derived from electromagnetic output of an electromagnetic source within a body is provided. The method accesses a model classifier for generating a classification for electromagnetic output of an electromagnetic source. The model classifier has model classifier weights learned based on training data that includes modeled derived electromagnetic data and model classifications. The modeled derived electromagnetic data is derived from modeled electromagnetic output generated using a computational model of the electromagnetic source that models the electromagnetic output of the electromagnetic source over time based on a source configuration. The method accesses patient training data that includes, for each of a plurality of patients, patient derived electromagnetic data and a patient classification for that patient. The method initializes patient classifier weights of the patient classifier based on the model classifier weights. The method trains the patient classifier with the patient training data and with the initialized patient classifier weights. In some embodiments, the classifier is a convolutional neural network. In some embodiments, the convolutional neural network inputs a one-dimensional image. In some embodiments, the model classifier is trained using training data that includes modeled derived electromagnetic data derived from modeled electromagnetic output generated based on source configurations that are identified as being similar to source configurations of the patients. In some embodiments, the electromagnetic source is a heart, a source configuration represents anatomical parameters and electrophysiology parameters of the heart, the modeled electromagnetic output represents activation of the heart, and the derived electromagnetic data is based on body-surface measurements. In some embodiments, a electrophysiology parameter is based on a heart disorder that is selected from a group consisting of but not limited to sinus rhythm, inappropriate sinus tachycardia, ectopic atrial rhythm, junctional rhythm, ventricular escape rhythm, atrial fibrillation, ventricular fibrillation, focal atrial tachycardia, atrial microreentry, ventricular tachycardia, atrial flutter, premature ventricular complexes, premature atrial complexes, atrioventricular nodal reentrant tachycardia, atrioventricular reentrant tachycardia, permanent junctional reciprocating tachycardia, and junctional tachycardia. In some embodiments, the electromagnetic data is a cardiogram. In some embodiments, the classification is a source location. In some embodiments, the patient derived electromagnetic data for a patient is derived from patient electromagnetic output of the electromagnetic source of that patient. In some embodiments, the method further receives target patient derived electromagnetic data for a target patient and applies the patient classifier to the target patient derived electromagnetic data to generate a classification for the target patient.

In some embodiments, a method performed by one or more computing systems for classifying patient derived electromagnetic data for a target patient is provided. The patient derived electromagnetic data is derived from patient electromagnetic output of an electromagnetic source within the patient's body. The method accesses a patient classifier to generate a classification for patient derived electromagnetic data of the electromagnetic source. The classifier is trained using weights of a model classifier and patient training data, the model classifier trained using modeled derived electromagnetic data and model classifications. The modeled derived electromagnetic data is generated from modeled electromagnetic output. The modeled electromagnetic output is generated for a plurality of source configurations using a computational model of the electromagnetic source. The patient training data includes patient derived electromagnetic data and patient classifications. The method receives the patient derived electromagnetic data for the target patient and applies the patient classifier to the received patient derived electromagnetic data to generate a patient classification for the target patient. In some embodiments, the electromagnetic source is a heart, a source configuration represents anatomical parameters and electrophysiology parameters of the heart, the modeled electromagnetic output represents activation of the heart, and the derived electromagnetic data is based on body-surface measurements.

In some embodiments, a computing system for generating a patient classifier for classifying a cardiogram is provided. The computing system comprises one or more computer-readable storage mediums storing computer-executable instructions and one or more processors for executing the computer-executable instructions stored in the one or more computer-readable storage mediums. The instructions control the computing system to initialize patient classifier weights of the patient classifier to model classifier weights of a model classifier. The model classifier is trained based on modeled cardiograms generated based on a computational model of the heart applied to model heart configurations. The instructions control the computing system to train the patient classifier with the patient training data and with the initialized patient classifier weights, the patient training data including, for each of a plurality of patients, a patient cardiogram and a patient classification for that patient. In some embodiments, the model classifier and the patient classifier are convolutional neural networks. In some embodiments, the convolutional neural networks input a one-dimensional image. In some embodiments, the model classifier and the patient classifier are neural networks. In some embodiments, the model classifier is trained using modeled cardiograms generated based on model heart configurations that are similar to patient heart configurations of the patients. In some embodiments, the computer-executable instructions further control the computing system to, for each of a plurality of clusters of similar patients, train a cluster patient classifier based on patient training data that includes cardiograms and patient classifications for the patients in that cluster. In some embodiments, the computer-executable instructions further control the computing system to identify similar patients based on comparison of patient heart configurations of the patients.

In some embodiments, the computer-executable instructions further control the computing system to identify similar patients based on comparison of cardiograms of the patients. In some embodiments, the computer-executable instructions further control the computing system to identify a cluster of similar patients that are similar to a target patient and apply the cluster patient classifier for that identified cluster to a target patient cardiogram of the target patient to generate a target patient classification for the target patient.

In some embodiments, a method performed by a computing system for generating a classification for a target patient based on a target cardiogram of the target patient is provided. The method generates a patient classifier based on patient training data that includes cardiograms of patients and based on a transference from a model classifier generated based on model training data that includes modeled cardiograms. The modeled cardiograms are generated based on a computational model of the heart and model heart configurations. The method applies the patient classifier to the target cardiogram to generate a target classification for the target patient.

In some embodiments, a method performed by one or more computing systems for generating a patient-specific model classifier for classifying derived electromagnetic data derived from electromagnetic output of an electromagnetic source within a body is provided. The method identifies models that are similar to a target patient. For each model that is identified, the method applies a computational model of the electromagnetic source to generate modeled electromagnetic output of the electromagnetic source based on model source configuration for that model; derives modeled derived electromagnetic data from the generated modeled electromagnetic output for that model; and generates a label for that model. The method trains the patient-specific model classifier with the modeled derived electromagnetic data and the generated labels as training data. In some embodiments, the classifier is a convolutional neural network that inputs a one-dimensional image. In some embodiments, the similarity between a model and the target patient is based on source configurations. In some embodiments, the similarity between a model and the target patient is based on derived electromagnetic data. In some embodiments, the electromagnetic source is a heart, a source configuration represents anatomical parameters and electrophysiology parameters of the heart, the modeled electromagnetic output represents activation of the heart, and the derived electromagnetic data is based on body-surface measurements. In some embodiments, the electromagnetic data is a cardiogram. In some embodiments, the label represents a source location for a disorder of the electromagnetic source. In some embodiments, the training is based on a transference from a model classifier generated based on model training data that includes modeled derived electromagnetic data, the modeled derived electromagnetic data generated based on a computational model of the electromagnetic source and model source configurations. In some embodiments, the method further, for each of a plurality of clusters of similar target patients, trains a cluster-specific model classifier based on derived electromagnetic data for models that are similar to the target patients of that cluster. In some embodiments, the method further identifies a cluster whose target patients are similar to another target patient and applies the cluster-specific model classifier for that identified cluster to the target patient derived electromagnetic data of the other target patient to generate a target patient label for the other target patient. In some embodiments, the method further identifies the cluster of target patients based on comparison of patient source configurations of target patients. In some embodiments, the method further identifies the cluster of target patients based on comparison of patient derived electromagnetic data of the target patients.

In some embodiments, a computing system for generating a patient-specific model classifier for classifying a cardiogram of a target patient is provided. The computing system comprises one or more computer-readable storage mediums storing computer-executable instructions and one or more processors for executing the computer-executable instructions stored in the one or more computer-readable storage mediums. The instructions control the computing system to identify models that are similar to the target patient; and train the patient-specific model classifier based on training data that includes modeled cardiograms and model classifications of the identified models. The modeled cardiograms are generated using a computational model of the heart based on model heart configurations of the identified models. In some embodiments, the model classifications represent a source location for a heart disorder. In some embodiments, the training of the patient-specific model classifier is based on a transference from a model classifier generated based on model training data that includes modeled cardiograms. In some embodiments, the computer-executable instructions further control the computer system to, for each of a plurality of clusters of similar target patients, train a cluster-specific model classifier based on training data that includes modeled cardiograms and model classification of models that are similar to the target patients of that cluster. In some embodiments, the computer-executable instructions further control the computer system to identify a cluster whose target patients who are similar to another target patient and apply the cluster-specific model classifier for that identified cluster to a target patient cardiogram of the other target patient to generate a target patient classification for the other target patient. In some embodiments, the computer-executable instructions control the computer system to identify the clusters of similar target patients based on comparison of patient heart configurations of target patients. In some embodiments, the computer-executable instructions control the computer system to identify the clusters of similar target patients based on comparison of patient cardiograms of the target patients.

In some embodiments, a method performed by a computing system for generating a representation of an electromagnetic source is provided. The method identifies modeled derived electromagnetic data that matches patient derived electromagnetic data of a patient. The modeled derived electromagnetic data is derived from modeled electromagnetic output of the electromagnetic source generated using a computational model of the electromagnetic source. The modeled electromagnetic output has, for each of a plurality of time intervals, an electromagnetic value for locations of the electromagnetic source. The method identifies cycle within the modeled electromagnetic output from which the matching modeled derived electromagnetic data was derived. For each of a plurality of display locations of the electromagnetic source, the method generates a display electromagnetic value for that display location based on the electromagnetic values of the modeled electromagnetic output of the identified cycle. The method generates a display representation of the electromagnetic source that includes, for each of the plurality of display locations, a visual representation of the display electromagnetic value for that display location. In some embodiments, the display representation has geometry based on anatomical parameters of the electromagnetic source of the patient. In some embodiments, the visual representation of a display electromagnetic value is a shading based on magnitude of the display electromagnetic value. In some embodiments, the visual representation of a display electromagnetic value is a color selected based on magnitude of the display electromagnetic value. In some embodiments, the visual representation of a display electromagnetic value is an intensity of a color based on magnitude of the display electromagnetic value. In some embodiments, the display electromagnetic value is based on a difference between the electromagnetic value at the start of the cycle and the electromagnetic value at the end of the cycle. In some embodiments, the method further, for each of a plurality of display intervals of the identified cycle, generates and outputs a display representation for that display interval. In some embodiments, the display representations are output in sequence to illustrate activations of the electromagnetic source over time. In some embodiments, when multiple instances of derived electromagnetic data match the patient derived electromagnetic data, the generating of the display electromagnetic value for a display location is based on a combination of the electromagnetic values of the modeled electromagnetic output from which the matching instances of the modeled derived electromagnetic data were derived. In some embodiments, the combination is an average that is weighted based on closeness of the match. In some embodiments, the electromagnetic source is a heart.

In some embodiments, a method performed by a computing system for generating a representation of a heart is provided. The method identifies a modeled cardiogram that is similar to a patient cardiogram of a patient. For each of a plurality of display locations of the heart, the method generates a display electromagnetic value for that display location based on an electromagnetic value of modeled electromagnetic output of a heart from which the modeled cardiogram is derived. The modeled electromagnetic output is generated using a computational model of the heart. The method generates a display representation of the heart that includes, for each of the plurality of display locations, a visual representation of the display electromagnetic value for that display location. In some embodiments, the display representation has geometry based on anatomical parameters of the heart of the patient. In some embodiments, the visual representation of a display electromagnetic value is an intensity of a color based on magnitude of the display electromagnetic value. In some embodiments, the displayed electromagnetic value is based on a difference between the electromagnetic value at the start of a model cycle within the modeled electromagnetic output and the electromagnetic value at the end of the model cycle. In some embodiments, the model cycle is selected based on similarity to a patient cycle within the cardiogram. In some embodiments, the method further, for each of a plurality of display intervals of the modeled electromagnetic output, generates and outputs a display representation for that display interval. In some embodiments, the display representations are output in sequence to illustrate activations of the electromagnetic source over time.

In some embodiments, a computing system for displaying a representation of electrical activation of a heart of a patient is provided. The computing system comprises one or more computer-readable storage mediums storing computer-executable instructions and one or more processors for executing the computer-executable instructions stored in the one or more computer-readable storage mediums. The instructions control the computing system to identify a modeled cardiogram that is similar to a patient cardiogram of the patient. The instructions control the computing system to generate a display representation of the heart that includes, for each of a plurality of display locations of the heart, a visual representation of a display value for that display location. The display values are based on modeled electromagnetic output of a heart from which the modeled cardiogram is derived. The modeled electromagnetic output is generated using a computational model of the heart. The instructions control the computing system to display the display representation. In some embodiments, the display representation has geometry based on anatomical parameters of the heart of the patient.

In some embodiments, a method performed by a computing system for generating a surface representation of an electromagnetic force generated by an electromagnetic source within a body is provided. The method accesses a sequence of vectors representing magnitude and direction of the electromagnetic force over time. The vectors are relative to an origin. For each pair of adjacent vectors, the method identifies a region based on the origin and the pair of vectors; generates a region representation of the region; and displays the generated region representation of the region. In some embodiments, the method displays a representation of the electromagnetic source so that the displayed region representations visually emanate from the electromagnetic source. In some embodiments, the origin is within the electromagnetic source. In some embodiments, the electromagnetic source is a heart and the sequence of vectors is a vectorcardiogram.

In some embodiments, the electromagnetic force has cycles and the region representations for a cycle form the surface representation for that cycle, and the method further simultaneously displays surface representations for multiple cycles. In some embodiments, the generated region representations of the regions are displayed in sequence to illustrate changes in the electromagnetic force over time.

In some embodiments, a computing system for displaying a representation of vectorcardiogram is provided. The computing system comprises one or more computer-readable storage mediums storing computer-executable instructions and one or more processors for executing the computer-executable instructions stored in the one or more computer-readable storage mediums. The instructions for controlling the computing system to generate a surface representation of a portion of the vectorcardiogram where the surface representation is bounded by points representing x, y, and z values of vectors of the portion of the vectorcardiogram; and display the generated surface representation. In some embodiments, the computer-executable instructions further control the computing system to display a representation of the heart from which the vectorcardiogram is derived so that the displayed surface representation visually emanates from the displayed representation of the heart. In some embodiments, the vectors are relative to an origin that is within the heart. In some embodiments, the vectorcardiogram has cycles and wherein the computer-executable instructions further control the computing system to simultaneously display the surface representations for multiple cycles. In some embodiments, the generated surface representation is incrementally displayed to illustrate changes in the vectorcardiogram over time. In some embodiments, the surface representation is displayed on a region-by-region basis.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims. In some embodiments, the MLMO system can be employed to classify electromagnetic output of an electromagnetic source based on different types of classifications. For example, the classifications may include location of a heart disorder (e.g., rotor location), scar or fibrosis or pro-arrhythmic substrate location, heart geometry (e.g., ventricle orientation), and so on. To generate the training data, the MLMO system labels the training data with the classification type that the classifier is to generate. Accordingly, the invention is not limited except as by the appended claims.

The invention claimed is:

1. One or more computing systems for bootstrapping generation of modeled electromagnetic output of a heart, the one or more computing systems comprising:
one or more computer-readable storage mediums storing:
a first modeled electromagnetic output for a first arrhythmia model of the heart at first simulation intervals, the first modeled electromagnetic output generated by simulating electrical activity of a heart based on first initialization values of the first modeled electromagnetic output; and
computer-executable instructions for controlling the one or more computing systems to:
initialize second modeled electromagnetic output for a second arrhythmia model of the heart to second initialization values of a first modeled electromagnetic output for one of the first simulation intervals, the second initialization values being different from the first initialization values; and
simulate second modeled electromagnetic output for the second arrhythmia model based on the initialized second modeled electromagnetic output; and
one or more processors for executing the computer-executable instructions stored in the one or more computer-readable storage mediums.

2. The one or more computing systems of claim 1 wherein the first arrhythmia model and the second arrhythmia model are based on different scar locations within the heart.

3. The one or more computing systems of claim 1 wherein the first arrhythmia model and the second arrhythmia model are based on different fibrosis locations within the heart.

4. The one or more computing systems of claim 1 wherein the first arrhythmia model and the second arrhythmia model are based on different pro-arrhythmic substrate locations within the heart.

5. The one or more computing systems of claim 1 wherein the modeled electromagnetic output for an arrhythmia model includes an electromagnetic mesh with a modeled electromagnetic value for each of a plurality of vertices of the electromagnetic mesh.

6. The one or more computing systems of claim 1 wherein the computer-executable instructions further control the one or more computing systems to, for each of a plurality of the first simulation intervals, generate by simulating electrical activity of a heart the first modeled electromagnetic output for the first arrhythmia model.

7. A method performed by one or more computing systems for bootstrapping a simulation, the method comprising:
accessing first simulation output for a first simulation, the first simulation based on first simulation parameters and having first simulation output for each of a plurality of first simulation intervals, the first simulation output being initialized to an initial first simulation output;
initializing second simulation output for a second simulation based on the first simulation output of a first simulation interval, the second simulation based on second simulation parameters, the second simulation output not being initialized to the initial first simulation output; and
for each of a plurality of second simulation intervals, calculating second simulated output for that second simulation interval based on the second simulated output of a prior second simulation interval wherein the first of the second simulation intervals is based on the initialized second simulation output.

8. The method of claim 7 wherein the first simulation output and the second simulation output are represented by values associated with vertices of a three-dimensional mesh.

9. The method of claim 7 further comprising, for each of a plurality of the first simulation intervals, calculating first simulated output for that first simulation interval based on the first simulated output of a prior first simulation interval.

10. The method of claim 7 wherein the initializing initializes the second simulation output to a first simulation output generated after the first simulation has stabilized.

11. A method performed by one or more computing systems for bootstrapping a simulation, the method comprising:
accessing first simulation output for a first simulation, the first simulation based on first simulation parameters and having first simulation output for each of a plurality of first simulation intervals;
initializing second simulation output for a second simulation based on the first simulation output of a first simulation interval, the second simulation based on second simulation parameters; and
for each of a plurality of second simulation intervals, calculating second simulated output for that second simulation interval based on the second simulated output of a prior second simulation interval wherein the first of the second simulation intervals is based on the initialized second simulation output
wherein the first simulation and the second simulation simulate electromagnetic output of an electromagnetic source.

12. The method of claim 11 wherein the electromagnetic source is a heart and the second simulation parameters are different from the first simulation parameters based on fibrosis location within the heart.

13. The method of claim 11 wherein the electromagnetic source is a heart and the second simulation parameters are different from the first simulation parameters based on pro-arrhythmic substrate location within the heart.

14. The method of claim 11 wherein the electromagnetic source is a heart and the first simulation and the second simulation simulate a simulated arrhythmia.

15. The method of claim 14 wherein the initializing initializes the second simulation output to a first simulation output after the simulated arrhythmia of the first simulation has stabilized.

16. One or more computing systems for bootstrapping a simulation, the one or more computing systems comprising:
one or more computer-readable storage mediums that store:
first simulation output for a first simulation interval of a first simulation, the first simulation being initialized to initial first simulation output; and
computer-executable instructions for controlling the one or more computing systems to:
initialize second simulation output for a second simulation based on the first simulation output of a first simulation interval, the second simulation output not being initialized to the initial first simulation output; and
for each of a plurality of second simulation intervals, calculate second simulated output for that second simulation interval based on the second simulated output of a prior second simulation interval wherein the first of the second simulation intervals is based on the second simulation output initialized based on the first simulation output; and one or more processors for controlling the one or more computing systems to execute one or more of the computer-executable instructions.

17. The one or more computing systems of claim 16 wherein the first simulation output and the second simulation output are represented by values associated with vertices of a three-dimensional mesh.

18. The one or more computing systems of claim 16 wherein the computer-executable instructions further control the one or more computing systems to, for each of a plurality of the first simulation intervals, calculate first simulated output for that first simulation interval based on the first simulated output of a prior first simulation interval.

19. The one or more computing systems of claim 16 wherein the computer-executable instructions that initialize the second simulation output initialize the second simulation output to a first simulation output generated after the first simulation has stabilized.

20. The one or more computing systems of claim 16 wherein the first simulation is based on first simulation parameters and the second simulation is based on second simulation parameters that are different from the first simulation parameters.

21. One or more computing systems for bootstrapping a simulation, the one or more computing systems comprising:
one or more computer-readable storage mediums that store:
first simulation output for a first simulation interval of a first simulation; and
computer-executable instructions for controlling the one or more computing systems to:
initialize second simulation output for a second simulation based on the first simulation output of a first simulation interval; and
for each of a plurality of second simulation intervals, calculate second simulated output for that second simulation interval based on the second simulated output of a prior second simulation interval wherein the first of the second simulation intervals is based on the second simulation output initialized based on the first simulation output;
wherein the first simulation and the second simulation simulate electromagnetic output of an electromagnetic source; and
one or more processors for controlling the one or more computing systems to execute one or more of the computer-executable instructions.

22. The one or more computing systems of claim 21 wherein the first simulation is based on first simulation parameters and the second simulation is based on second simulation parameters that are different from the first simulation parameters and wherein the electromagnetic source is a heart and the second simulation parameters are different from the first simulation parameters based on fibrosis location within the heart.

23. The one or more computing systems of claim 21 wherein the first simulation is based on first simulation parameters and the second simulation is based on second simulation parameters that are different from the first simulation parameters and wherein the electromagnetic source is a heart and the second simulation parameters are different from the first simulation parameters based on pro-arrhythmic substrate location within the heart.

24. The one or more computing systems of claim 21 wherein the electromagnetic source is a heart and the first simulation and the second simulation simulates a simulated arrhythmia.

25. The one or more computing systems of claim 24 wherein the computer-executable instructions that initialize the second simulation output of the second simulation interval initialize the second simulation output to a first simulation output after the simulated arrhythmia of the first simulation has stabilized.

* * * * *